(12) United States Patent
Kriesel et al.

(10) Patent No.: US 7,993,304 B2
(45) Date of Patent: Aug. 9, 2011

(54) FLUID DISPENSING APPARATUS

(75) Inventors: Marshall S. Kriesel, Saint Paul, MN (US); Joshua W. Kriesel, San Francisco, CA (US)

(73) Assignee: BioQuiddity, Inc., San Francisco, CA (US)

( * ) Notice: Subject to any disclaimer, the term of this patent is extended or adjusted under 35 U.S.C. 154(b) by 271 days.

(21) Appl. No.: 11/725,220

(22) Filed: Mar. 14, 2007

(65) Prior Publication Data
US 2007/0219501 A1    Sep. 20, 2007

Related U.S. Application Data

(60) Provisional application No. 60/783,019, filed on Mar. 15, 2006.

(51) Int. Cl.
| | |
|---|---|
| A61M 5/20 | (2006.01) |
| A61M 37/00 | (2006.01) |
| A61M 5/00 | (2006.01) |
| A61M 5/14 | (2006.01) |
| A61K 9/22 | (2006.01) |

(52) U.S. Cl. ........ 604/134; 604/131; 604/246; 604/247; 604/256; 604/890.1

(58) Field of Classification Search .................. 604/131, 604/134–136, 151, 153, 207, 211, 246–248, 604/256, 260, 890.1, 891.1
See application file for complete search history.

(56) References Cited

U.S. PATENT DOCUMENTS

| | | | |
|---|---|---|---|
| 2,236,084 A | 3/1941 | Brown | |
| RE27,155 E | 7/1971 | Hansen | |
| 3,731,681 A | 5/1973 | Blackshear et al. | |
| 3,884,228 A | 5/1975 | Hahn | |
| 4,381,006 A | 4/1983 | Genese | |
| 4,525,165 A | 6/1985 | Fischell | |
| 4,557,728 A | 12/1985 | Sealfon et al. | |
| 4,608,042 A | 8/1986 | Vanderveen et al. | |
| 4,681,566 A | 7/1987 | Fenton, Jr. et al. | |
| 4,755,172 A | 7/1988 | Baldwin | |
| 4,772,263 A | 9/1988 | Dorman et al. | |
| 4,850,807 A | 7/1989 | Frantz | |
| 4,863,429 A | 9/1989 | Baldwin | |
| 5,007,556 A | 4/1991 | Lover | |
| 5,014,750 A | 5/1991 | Winchell et al. | |
| 5,098,377 A | 3/1992 | Borsanyi et al. | |
| 5,100,389 A | 3/1992 | Vaillancourt | |
| 5,176,641 A | 1/1993 | Idriss | |
| 5,205,820 A | 4/1993 | Kriesel | |
| 5,226,551 A | 7/1993 | Robbins, III | |
| 5,236,418 A | 8/1993 | Kriesel | |
| 5,290,259 A | 3/1994 | Fischer | |
| 5,306,257 A | 4/1994 | Zdeb | |
| 5,314,405 A | 5/1994 | Kriesel et al. | |
| 5,333,761 A | 8/1994 | Davis et al. | |
| 5,336,188 A | 8/1994 | Kriesel | |

(Continued)

*Primary Examiner* — Nicholas D Lucchesi
*Assistant Examiner* — Victoria P Campbell
(74) *Attorney, Agent, or Firm* — James E. Brunton

(57) ABSTRACT

A compact fluid dispenser for use in controllably dispensing fluid medicaments, such as antibiotics, blood clotting agents, analgesics, and like medicinal agents from collapsible containers at a uniform rate. The dispenser includes a novel stored energy source that is provided in the form of a compressible-expandable member that functions to continuously and uniformly expel fluid from the apparatus reservoir. The apparatus further includes a novel fluid flow control assembly that precisely controls the flow of the medicament solutions from the apparatus reservoir to the patient.

7 Claims, 79 Drawing Sheets

U.S. PATENT DOCUMENTS

| | | |
|---|---|---|
| 5,346,476 A | 9/1994 | Elson |
| 5,380,287 A | 1/1995 | Kikuchi et al. |
| 5,411,480 A | 5/1995 | Kriesel |
| 5,419,771 A | 5/1995 | Kriesel |
| 5,484,410 A | 1/1996 | Kriesel |
| 5,499,968 A | 3/1996 | Milijasevic et al. |
| 5,514,090 A | 5/1996 | Kriesel et al. |
| 5,545,139 A | 8/1996 | Kriesel |
| 5,573,129 A * | 11/1996 | Nagata et al. ................. 215/382 |
| 5,620,420 A | 4/1997 | Kriesel |
| 5,632,315 A | 5/1997 | Rose |
| 5,632,406 A | 5/1997 | Robbins, III |
| 5,693,018 A | 12/1997 | Kriesel et al. |
| 5,693,019 A | 12/1997 | Kriesel |
| 5,720,729 A | 2/1998 | Kriesel |
| 5,721,382 A | 2/1998 | Kriesel et al. |
| 5,735,818 A | 4/1998 | Kriesel et al. |
| 5,741,242 A | 4/1998 | Kriesel |
| 5,743,879 A | 4/1998 | Kriesel |
| 5,766,149 A | 6/1998 | Kriesel et al. |
| 5,779,676 A | 7/1998 | Kriesel et al. |
| 5,807,323 A | 9/1998 | Kriesel et al. |
| 5,836,484 A | 11/1998 | Gerber |
| 5,858,005 A | 1/1999 | Kriesel |
| 5,885,250 A | 3/1999 | Kriesel et al. |
| 5,897,530 A | 4/1999 | Jackson |
| 5,921,962 A | 7/1999 | Kriesel et al. |
| 5,925,017 A | 7/1999 | Kriesel et al. |
| 5,957,891 A | 9/1999 | Kriesel et al. |
| 5,993,425 A | 11/1999 | Kriesel |
| 6,010,482 A | 1/2000 | Kriesel et al. |
| 6,027,472 A | 2/2000 | Kriesel et al. |
| 6,030,363 A | 2/2000 | Kriesel |
| 6,045,533 A | 4/2000 | Kriesel et al. |
| 6,063,059 A | 5/2000 | Kriesel |
| 6,068,613 A | 5/2000 | Kriesel et al. |
| 6,068,614 A | 5/2000 | Kimber et al. |
| 6,086,561 A | 7/2000 | Kriesel et al. |
| 6,090,071 A | 7/2000 | Kriesel |
| 6,095,491 A | 8/2000 | Kriesel |
| 6,126,637 A | 10/2000 | Kriesel et al. |
| 6,126,642 A | 10/2000 | Kriesel et al. |
| 6,152,898 A | 11/2000 | Olsen |
| 6,159,180 A | 12/2000 | Kriesel et al. |
| 6,176,845 B1 | 1/2001 | Kriesel et al. |
| 6,183,441 B1 | 2/2001 | Kriesel et al. |
| 6,190,359 B1 | 2/2001 | Heruth |
| 6,210,368 B1 | 4/2001 | Rogers |
| 6,236,624 B1 | 5/2001 | Kriesel et al. |
| 6,245,041 B1 | 6/2001 | Kriesel |
| 6,258,062 B1 | 7/2001 | Thielen et al. |
| 6,270,481 B1 | 8/2001 | Mason et al. |
| 6,273,133 B1 | 8/2001 | Williamson et al. |
| 6,277,095 B1 | 8/2001 | Kriesel et al. |
| 6,293,159 B1 | 9/2001 | Kriesel et al. |
| 6,319,235 B1 | 11/2001 | Yoshino |
| 6,355,019 B1 | 3/2002 | Kriesel et al. |
| 6,391,006 B1 | 5/2002 | Kriesel et al. |
| 6,394,980 B2 | 5/2002 | Kriesel et al. |
| 6,398,760 B1 | 6/2002 | Danby |
| 6,416,495 B1 * | 7/2002 | Kriesel et al. ................. 604/132 |
| 6,485,461 B1 | 11/2002 | Mason et al. |
| 6,537,249 B2 | 3/2003 | Kriesel et al. |
| 6,542,350 B1 | 4/2003 | Rogers |
| 6,569,125 B2 | 5/2003 | Jepson et al. |
| 6,645,175 B2 | 11/2003 | Kriesel et al. |
| 6,669,668 B1 | 12/2003 | Kleeman et al. |
| 6,679,304 B1 * | 1/2004 | Vacca ........................... 141/313 |
| 7,029,455 B2 | 4/2006 | Flaherty |
| 7,108,151 B2 * | 9/2006 | Higuchi ........................ 220/666 |
| 2001/0054627 A1 * | 12/2001 | Lin et al. .................... 222/386.5 |
| 2005/0033233 A1 * | 2/2005 | Kriesel ........................ 604/133 |
| 2005/0038387 A1 * | 2/2005 | Kriesel et al. ................ 604/133 |
| 2006/0030819 A1 | 2/2006 | Young et al. |

* cited by examiner

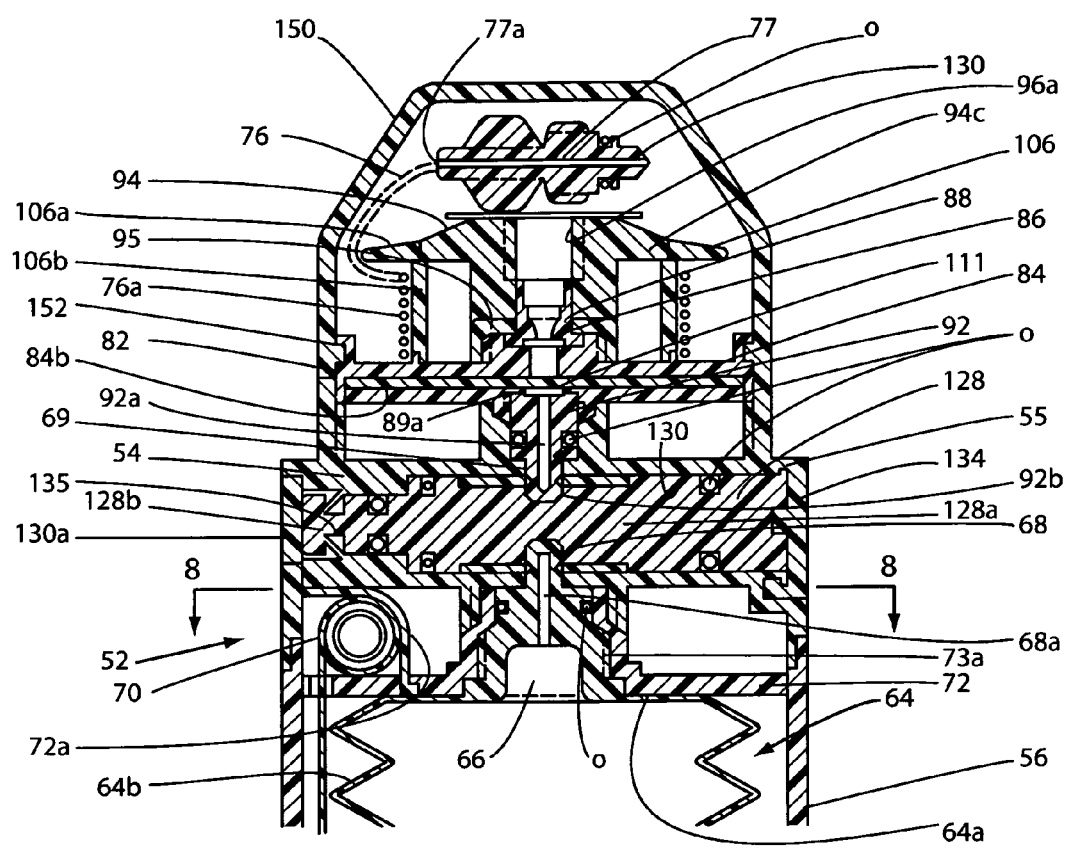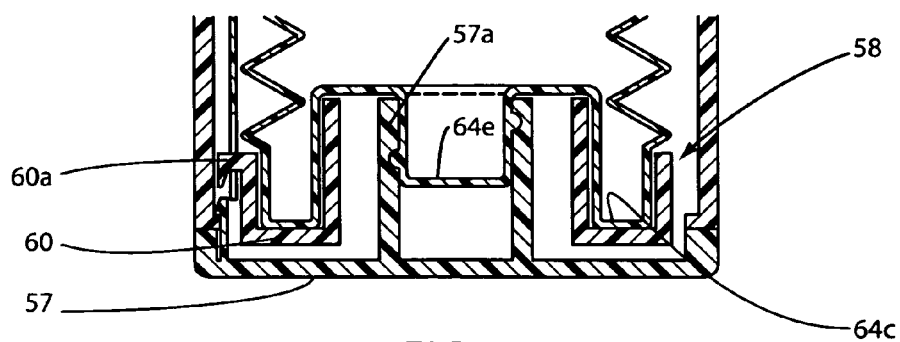
FIG. 3

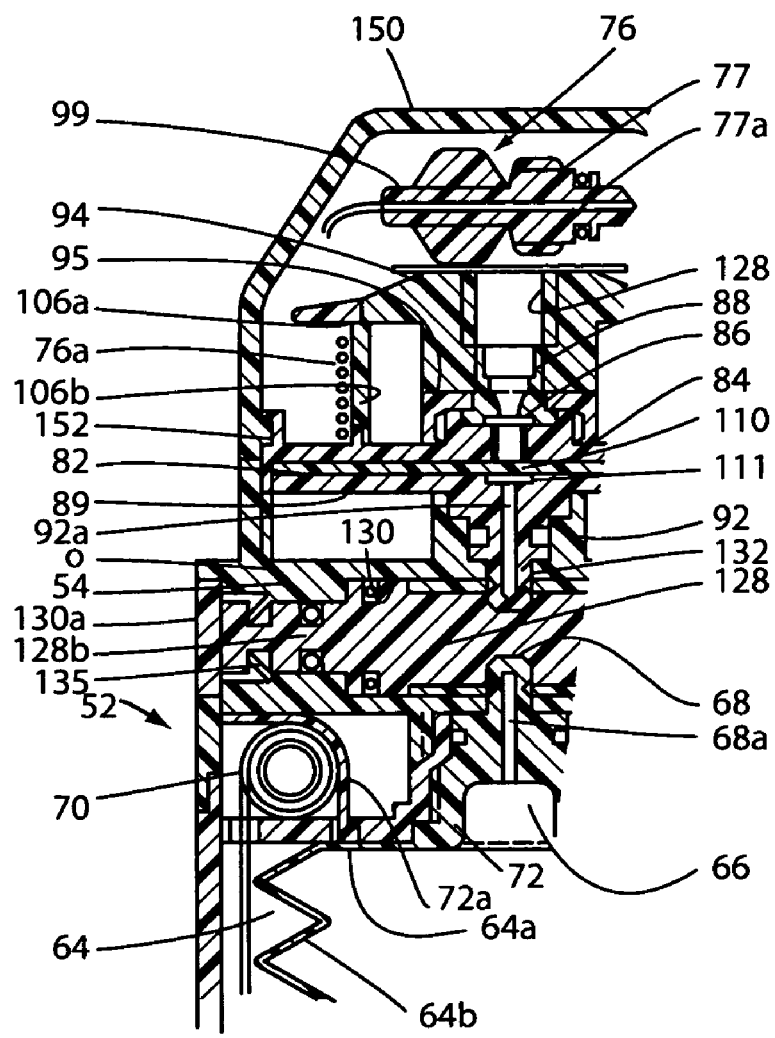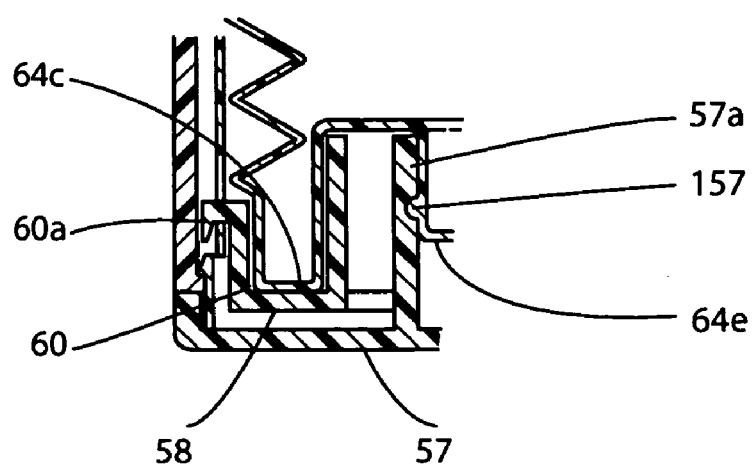
FIG. 4A

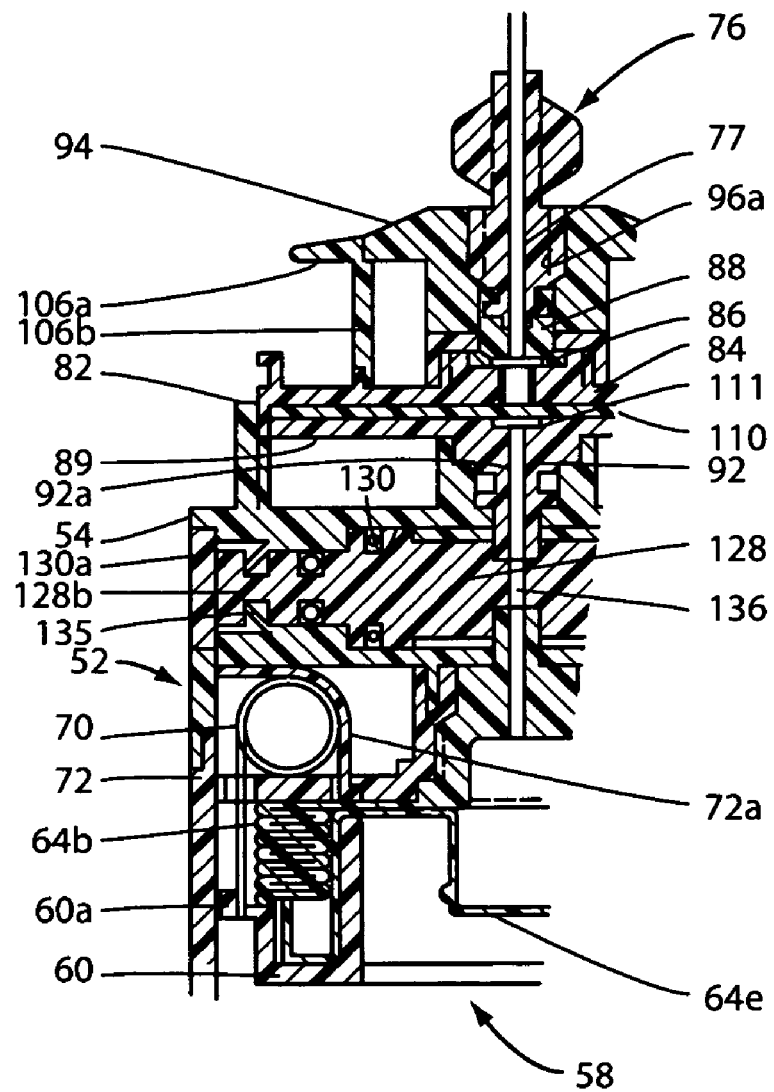
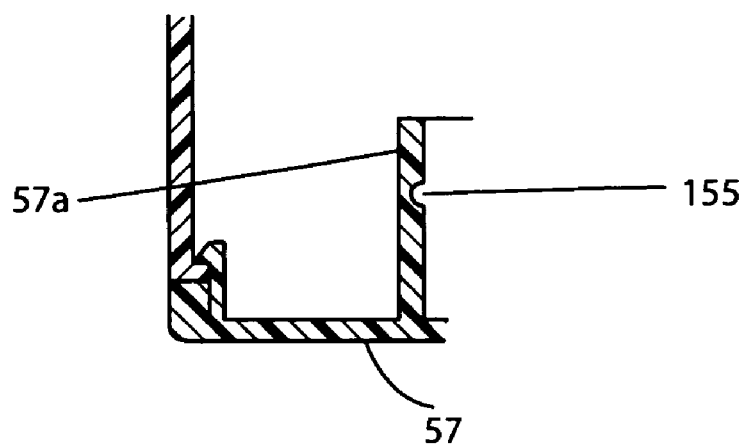
FIG. 4B

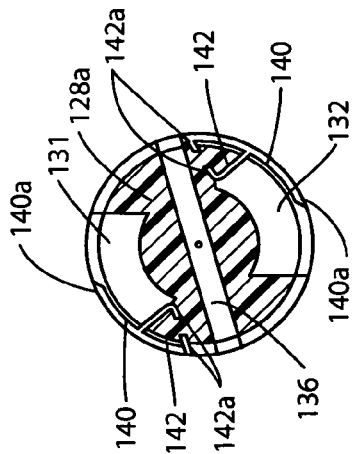
FIG. 41
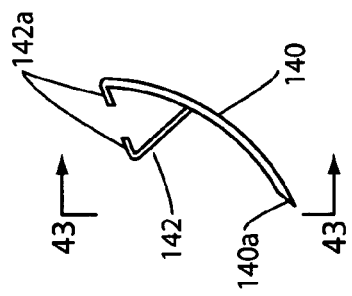
FIG. 42
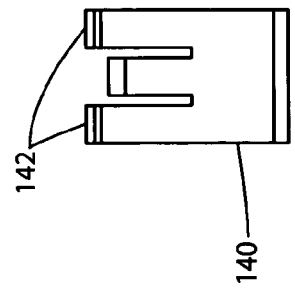
FIG. 43
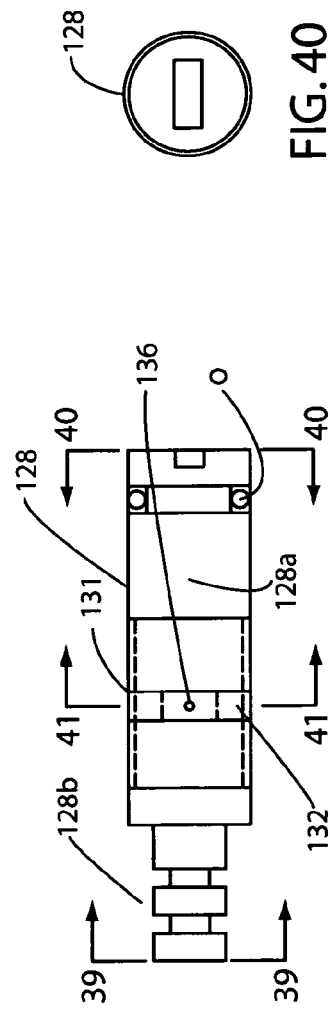
FIG. 38
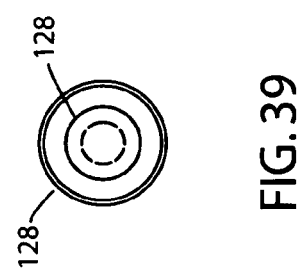
FIG. 40
FIG. 39

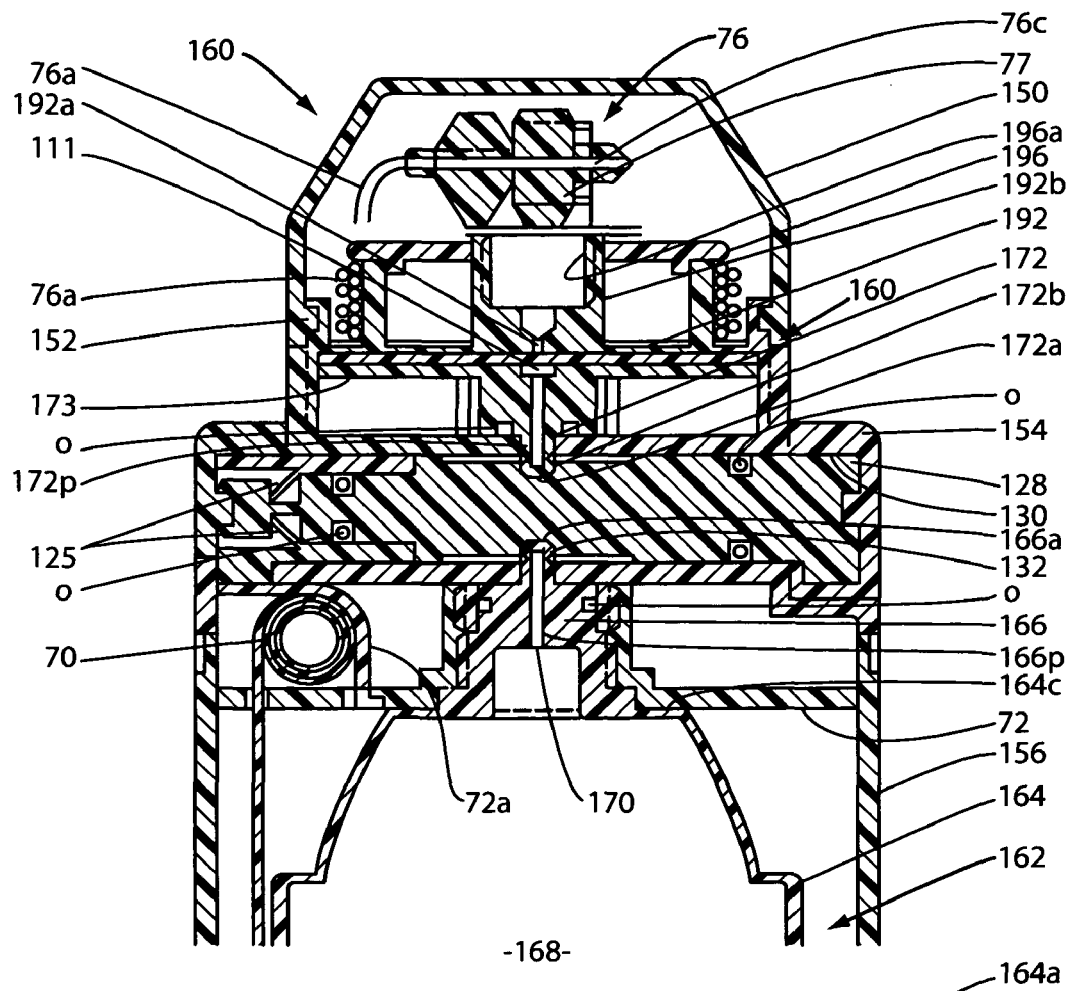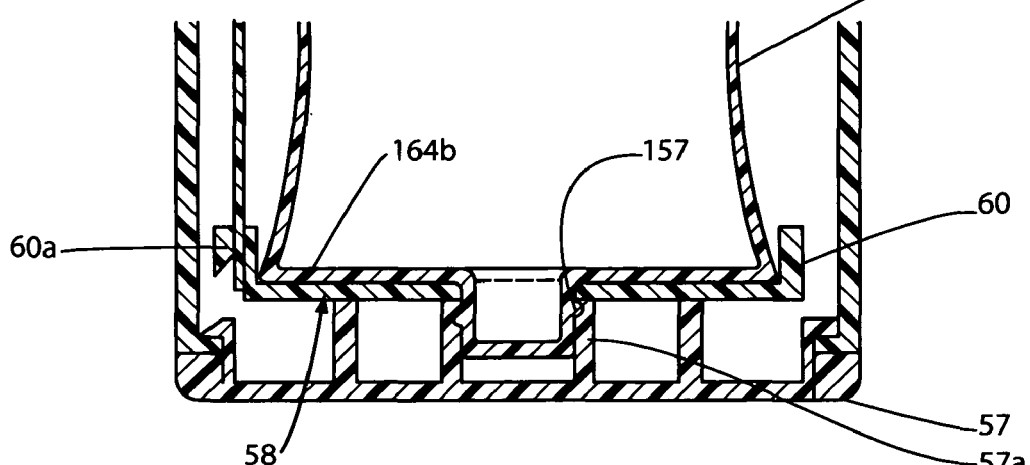
FIG. 52

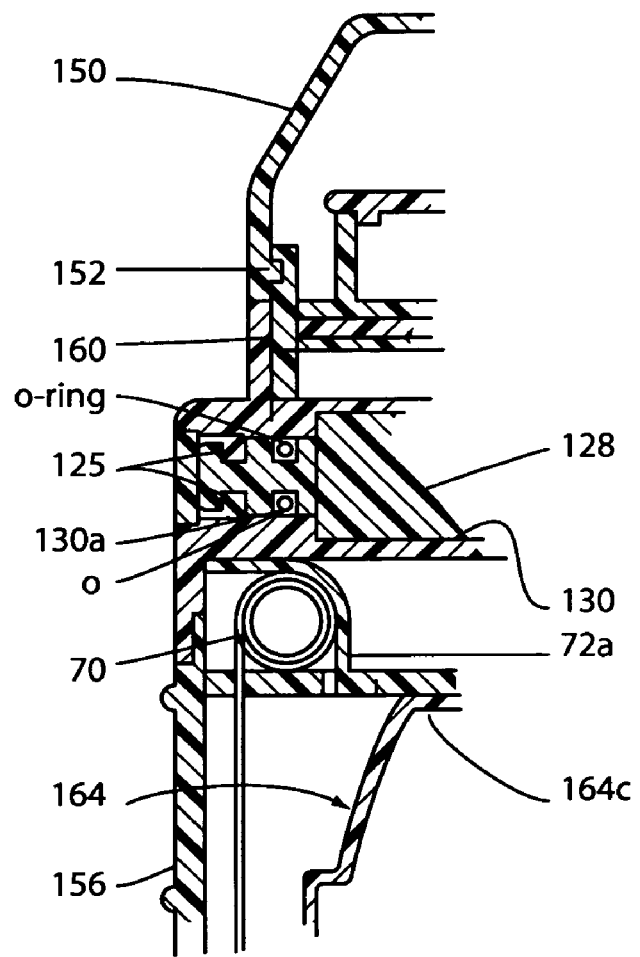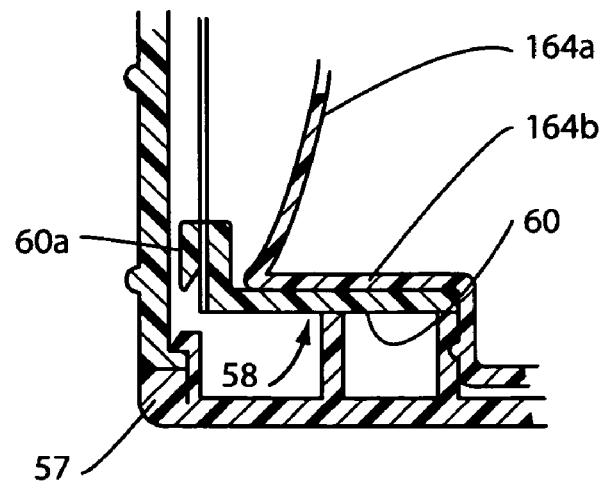
FIG. 53A

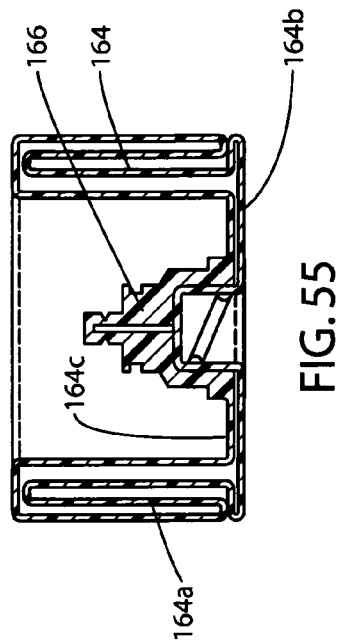
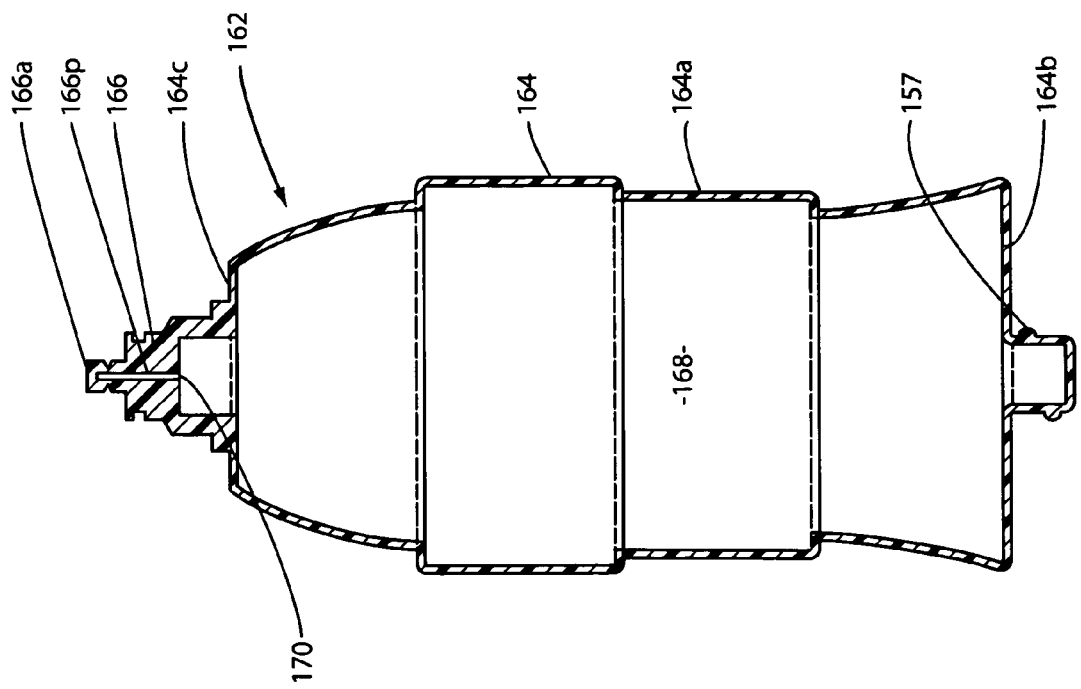
FIG. 55
FIG. 54

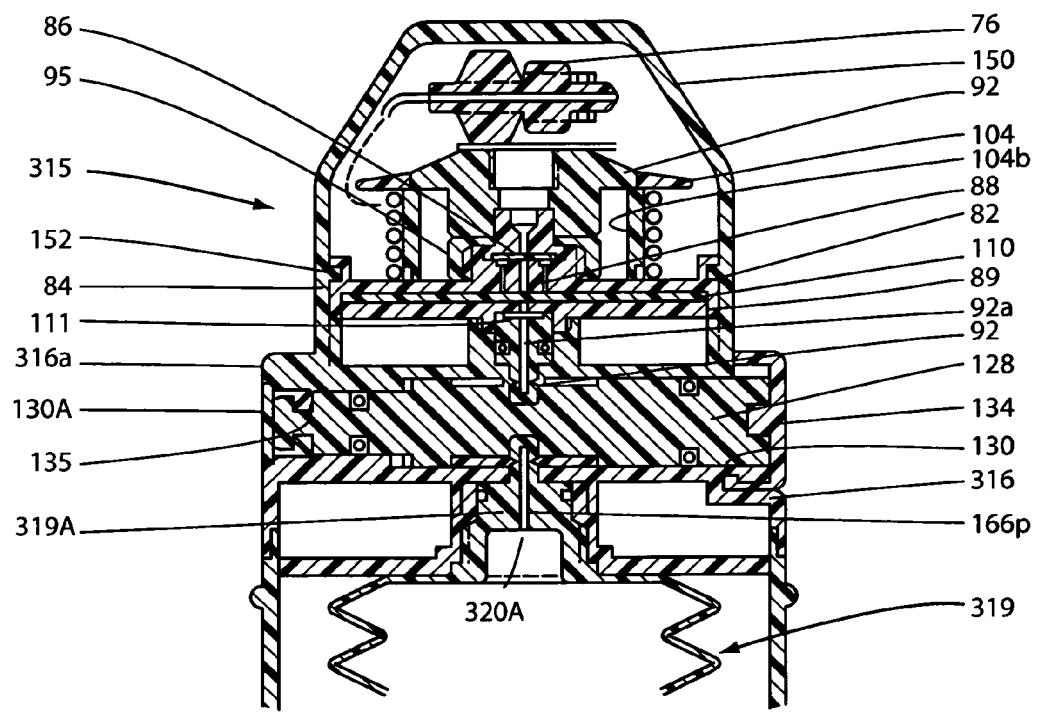
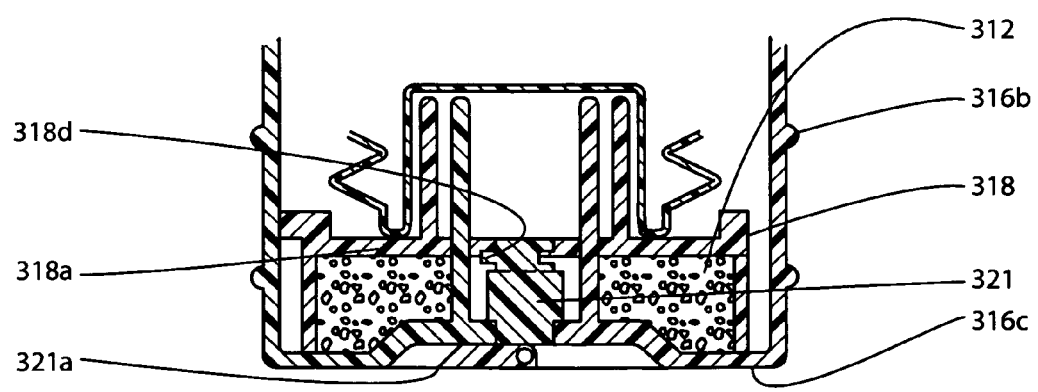
FIG.67A

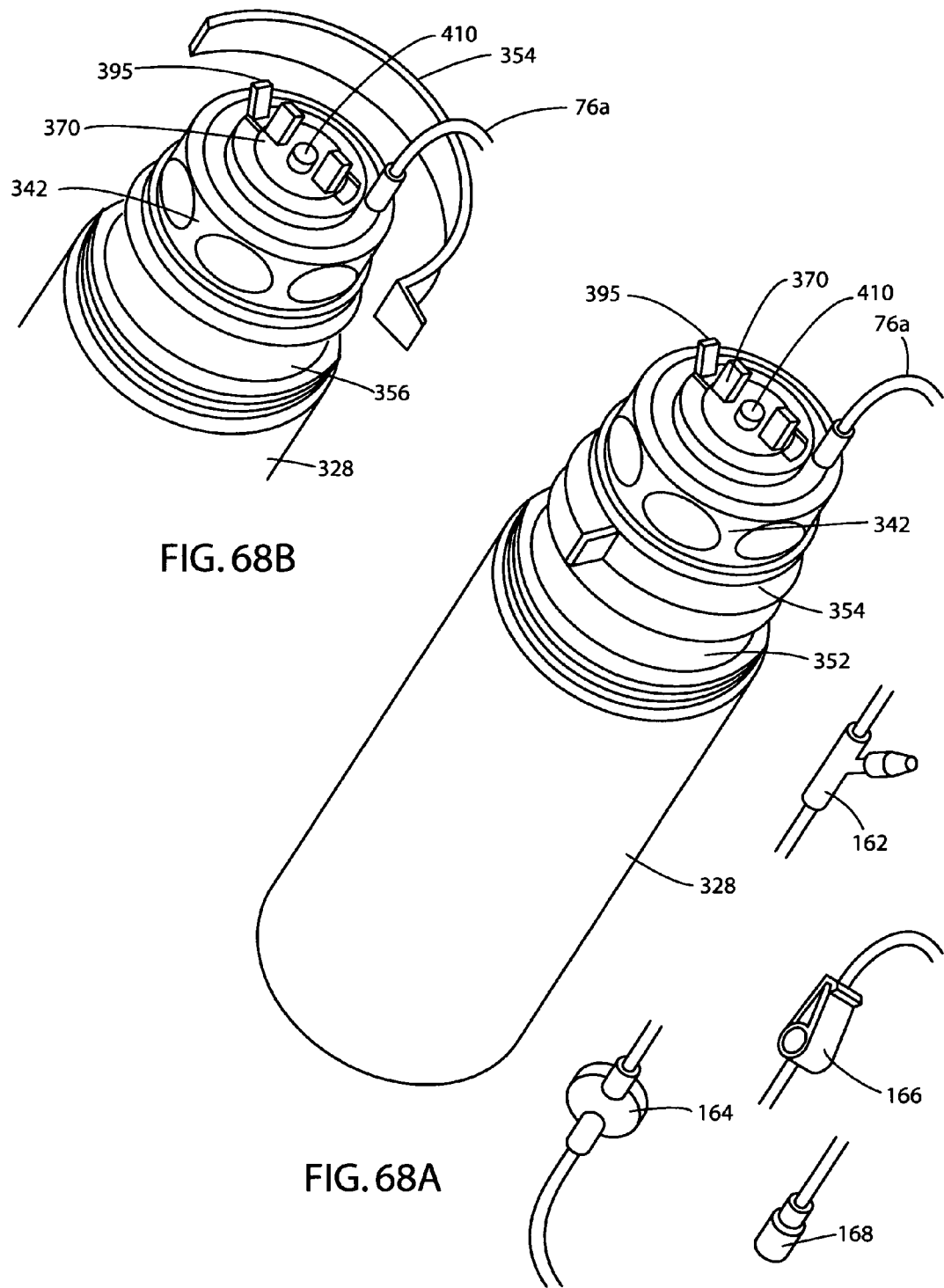

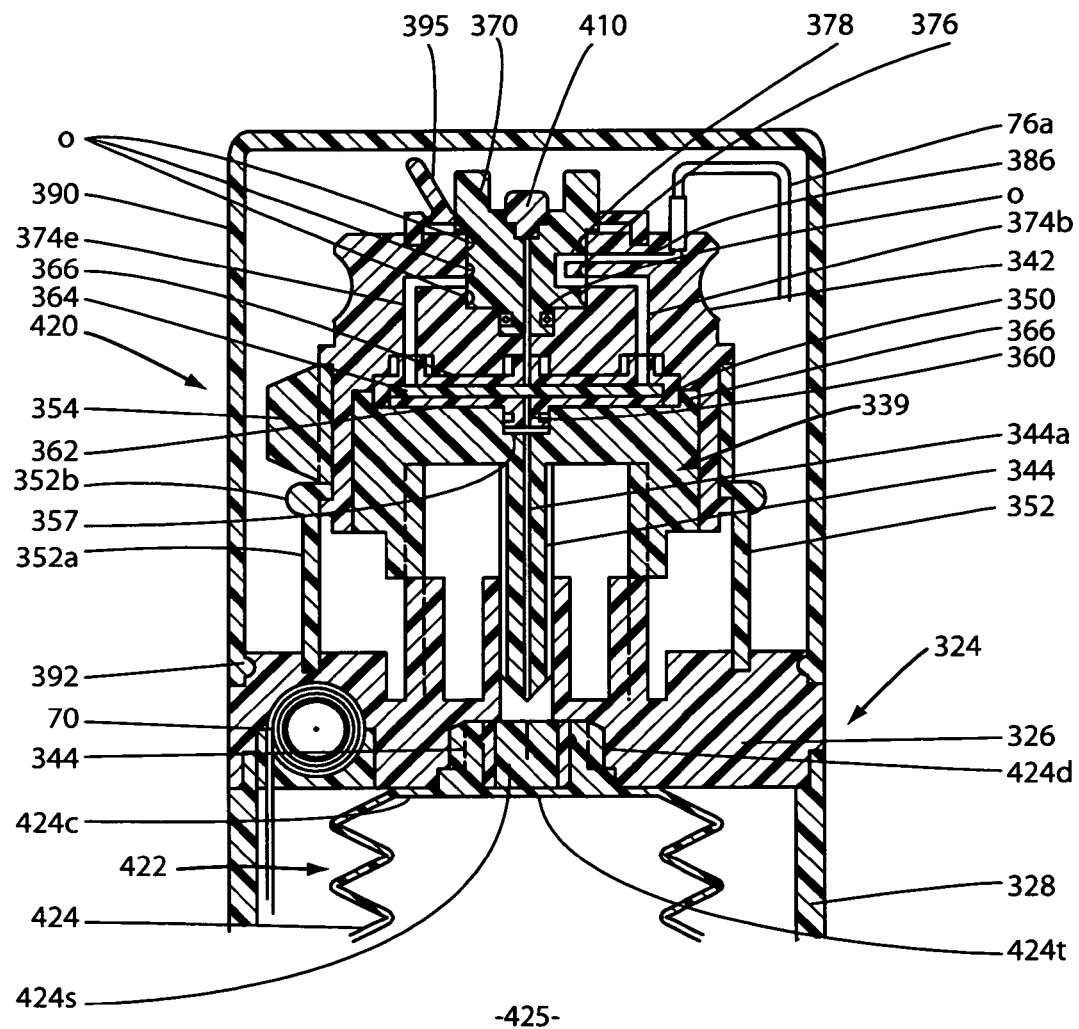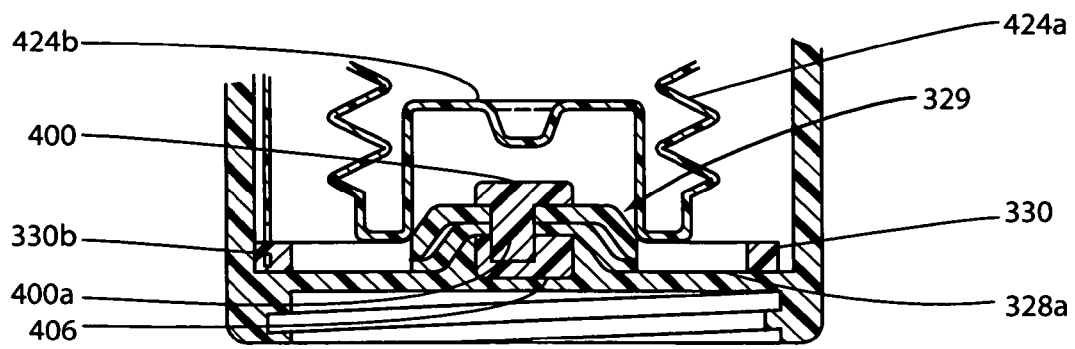
FIG. 70

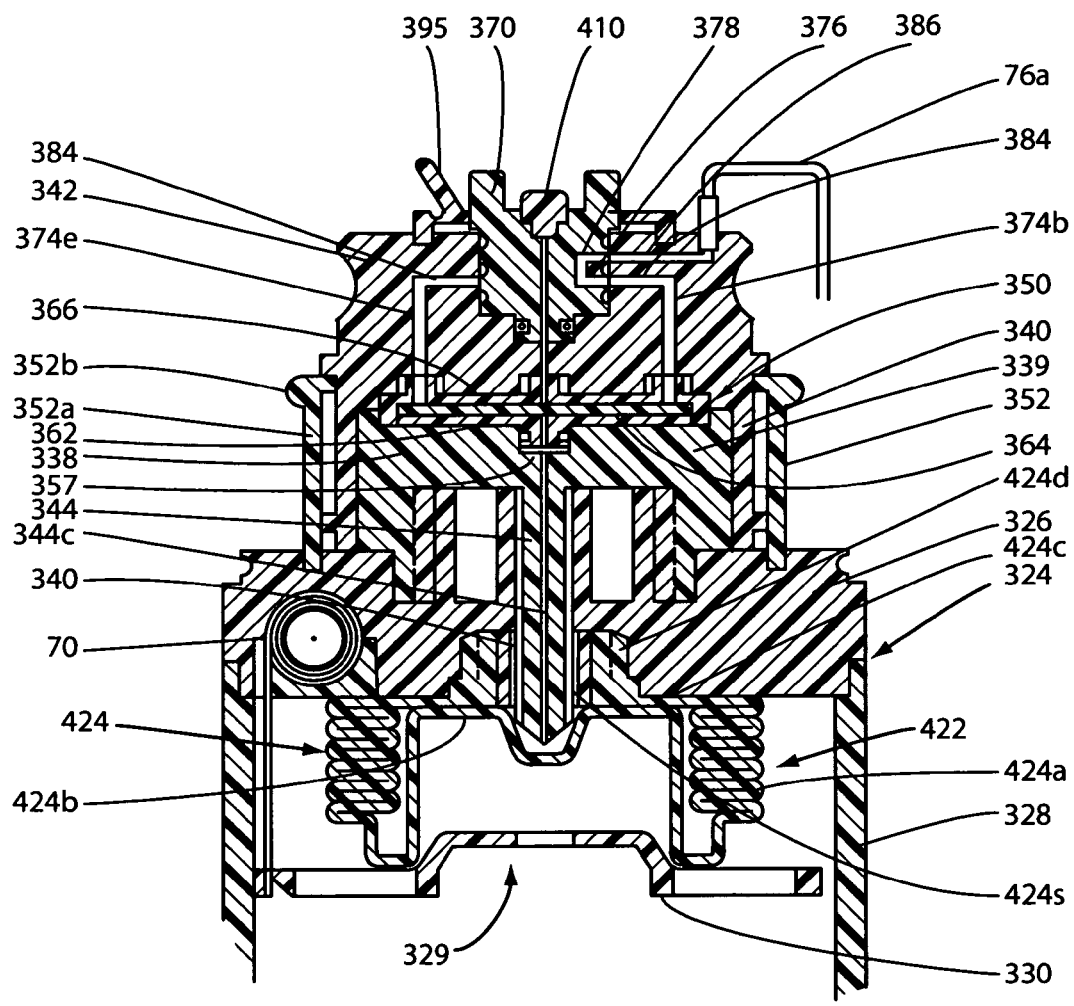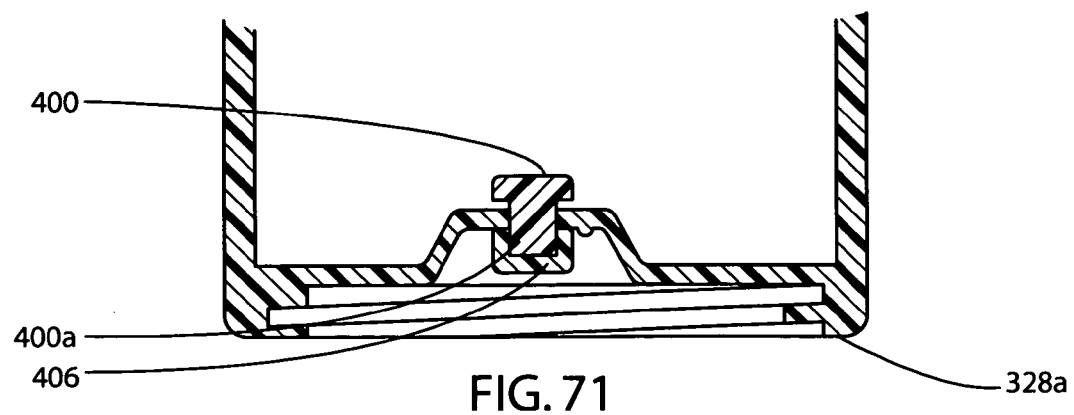
FIG. 71

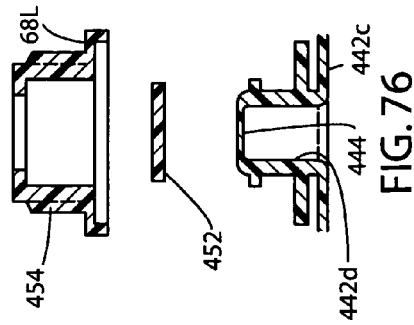
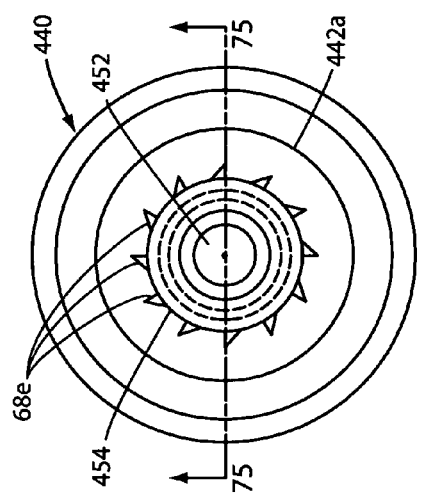
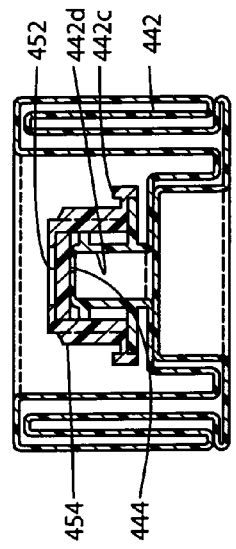
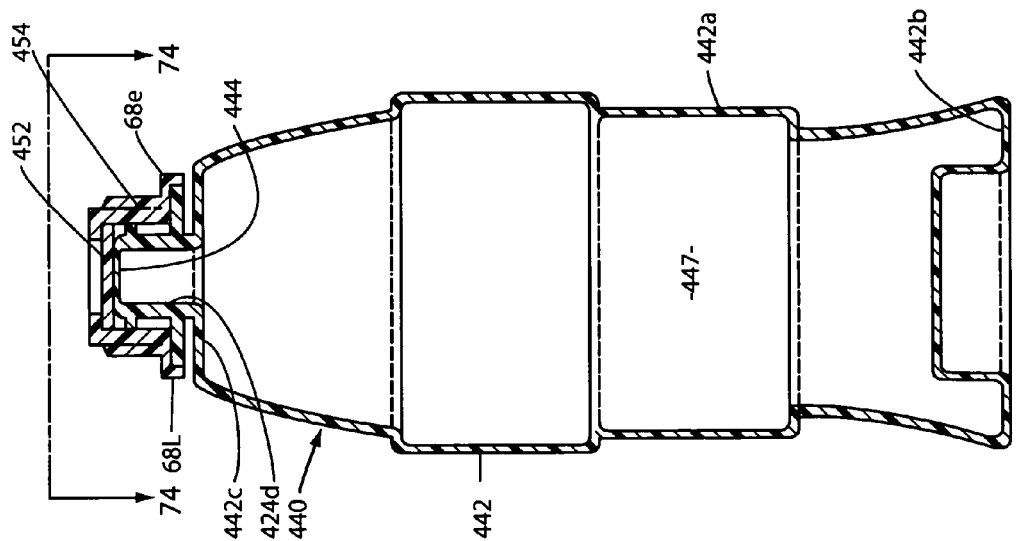
FIG. 76
FIG. 74
FIG. 77
FIG. 75

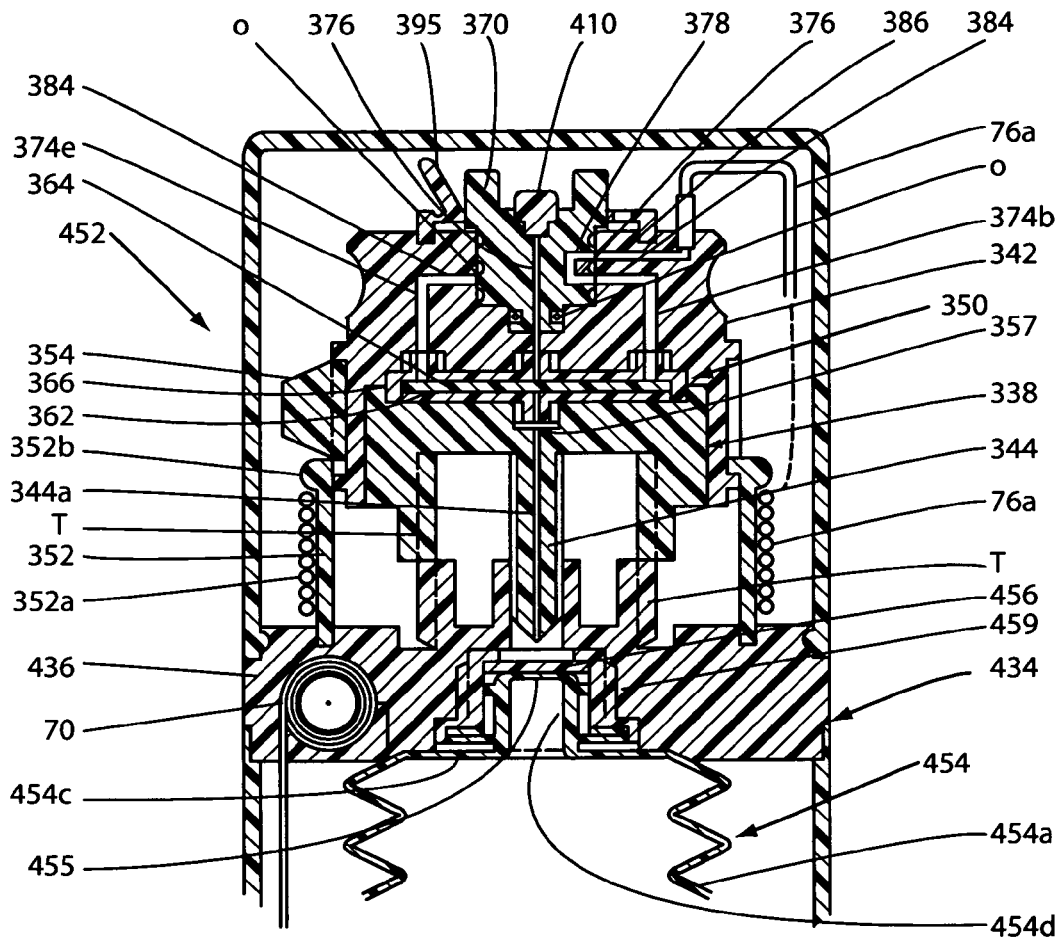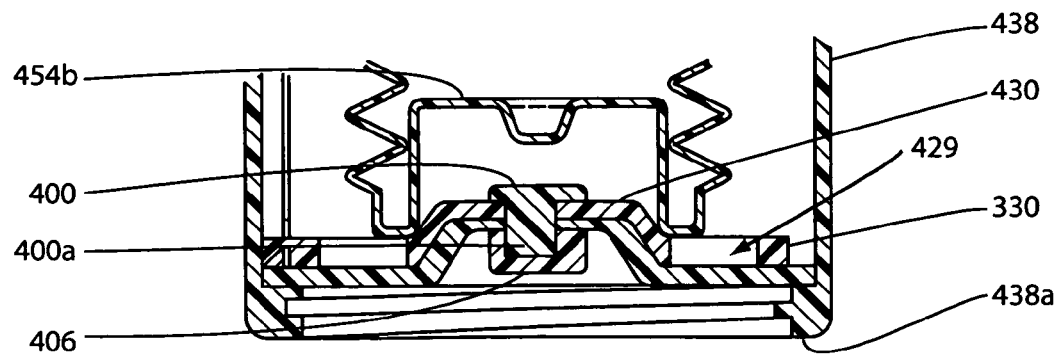
FIG. 78

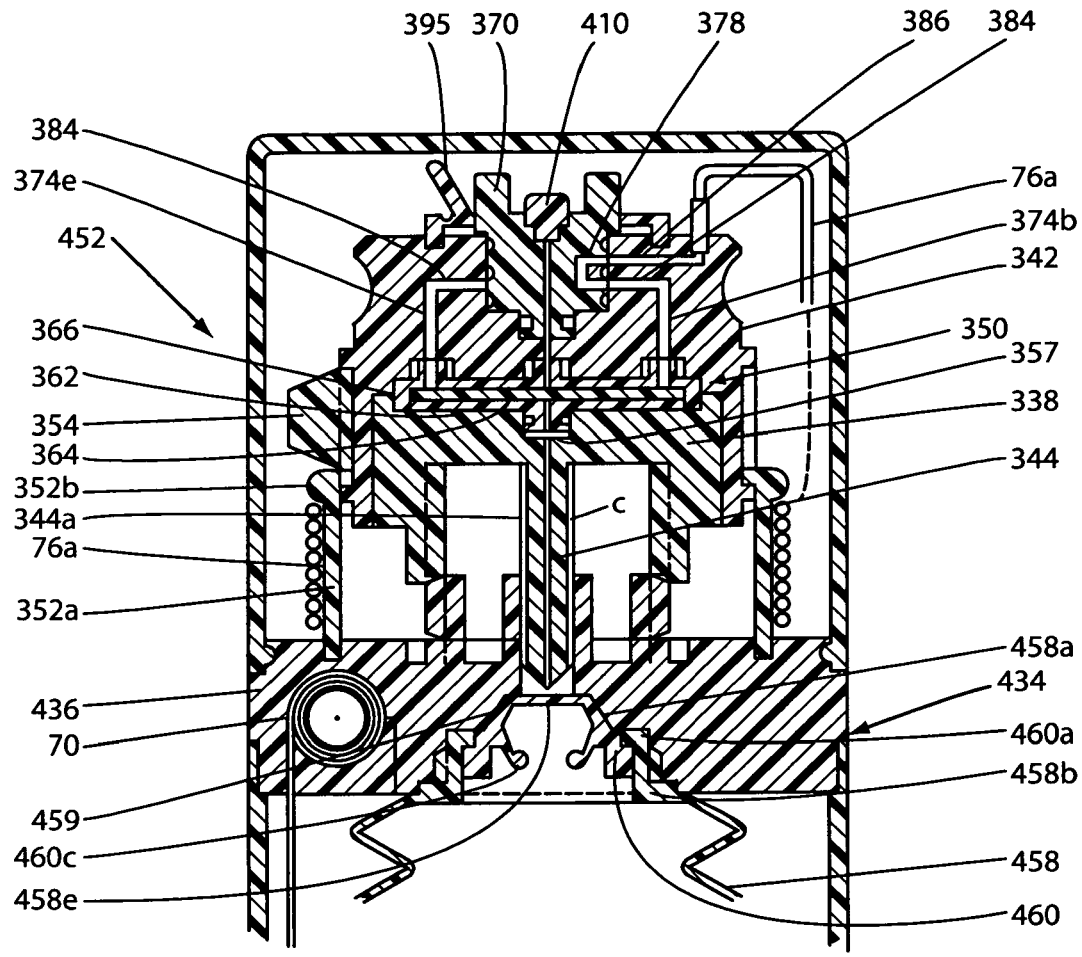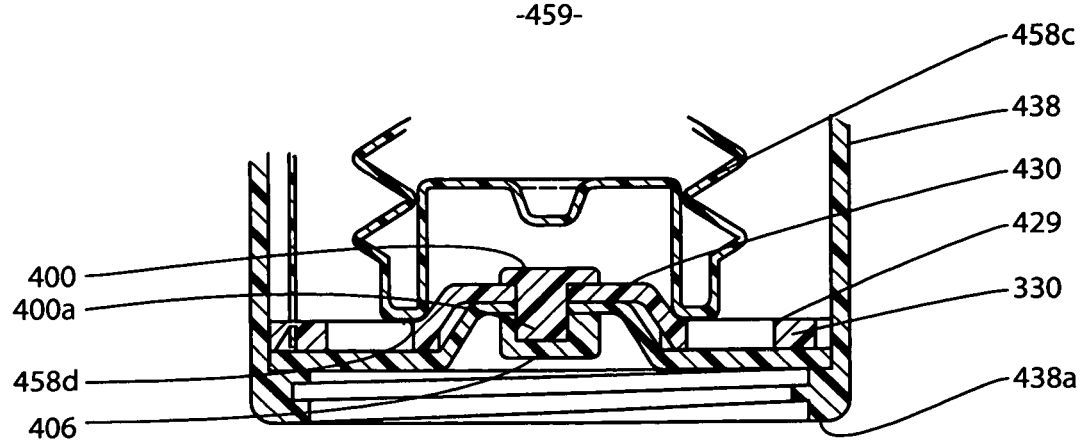
FIG. 82A

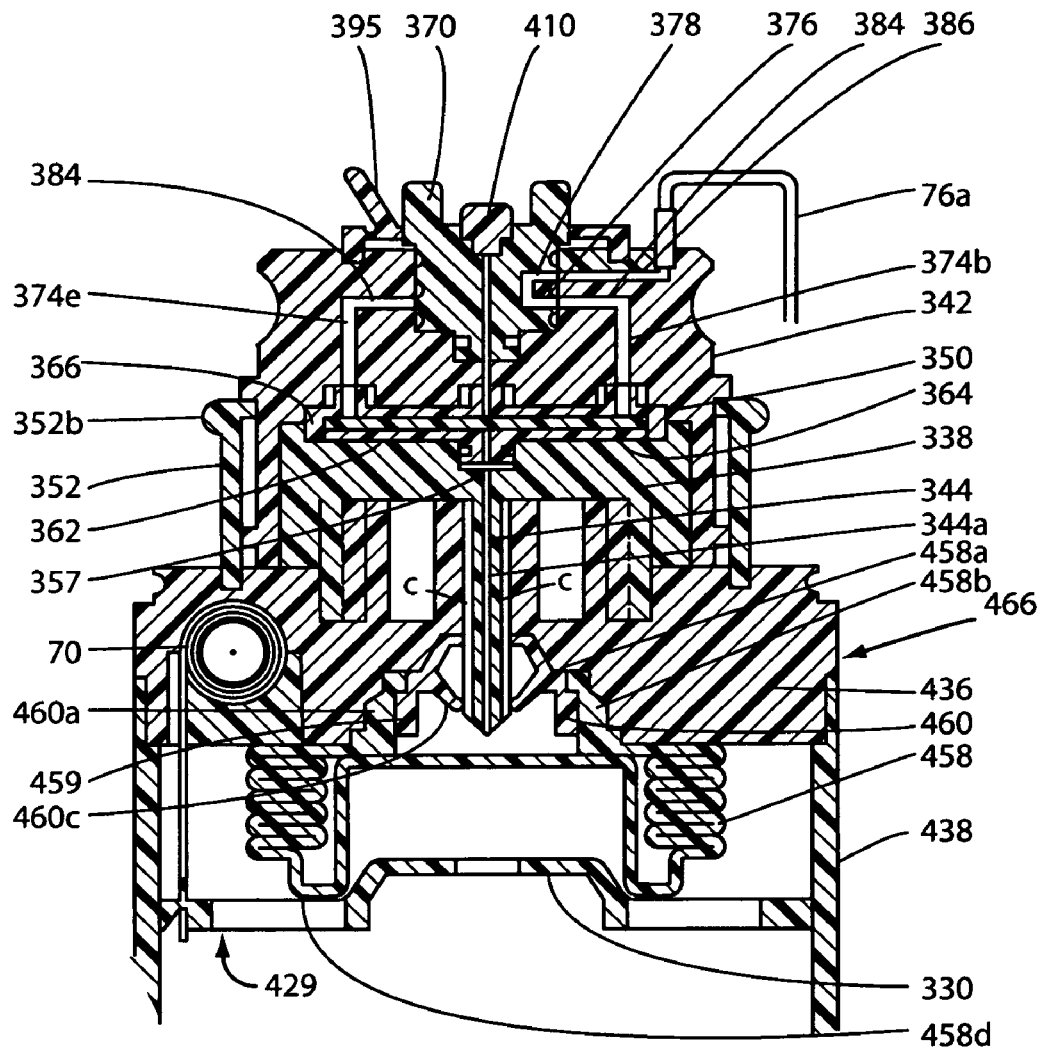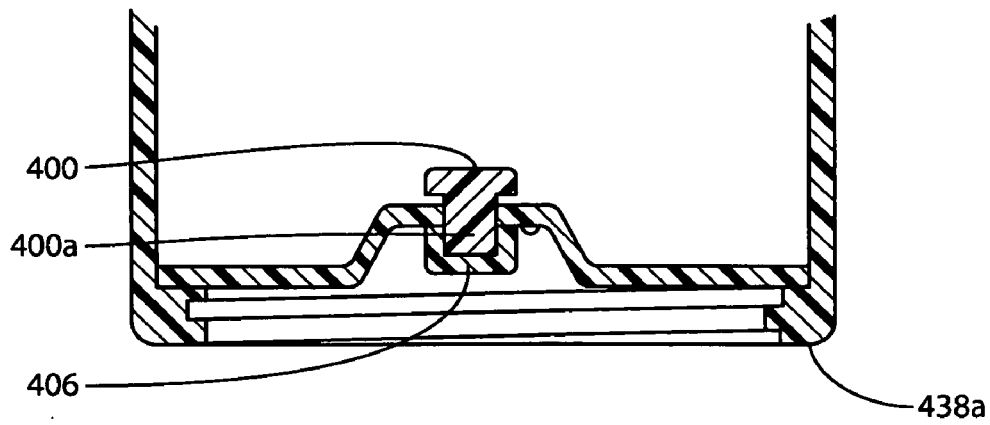
FIG. 82B

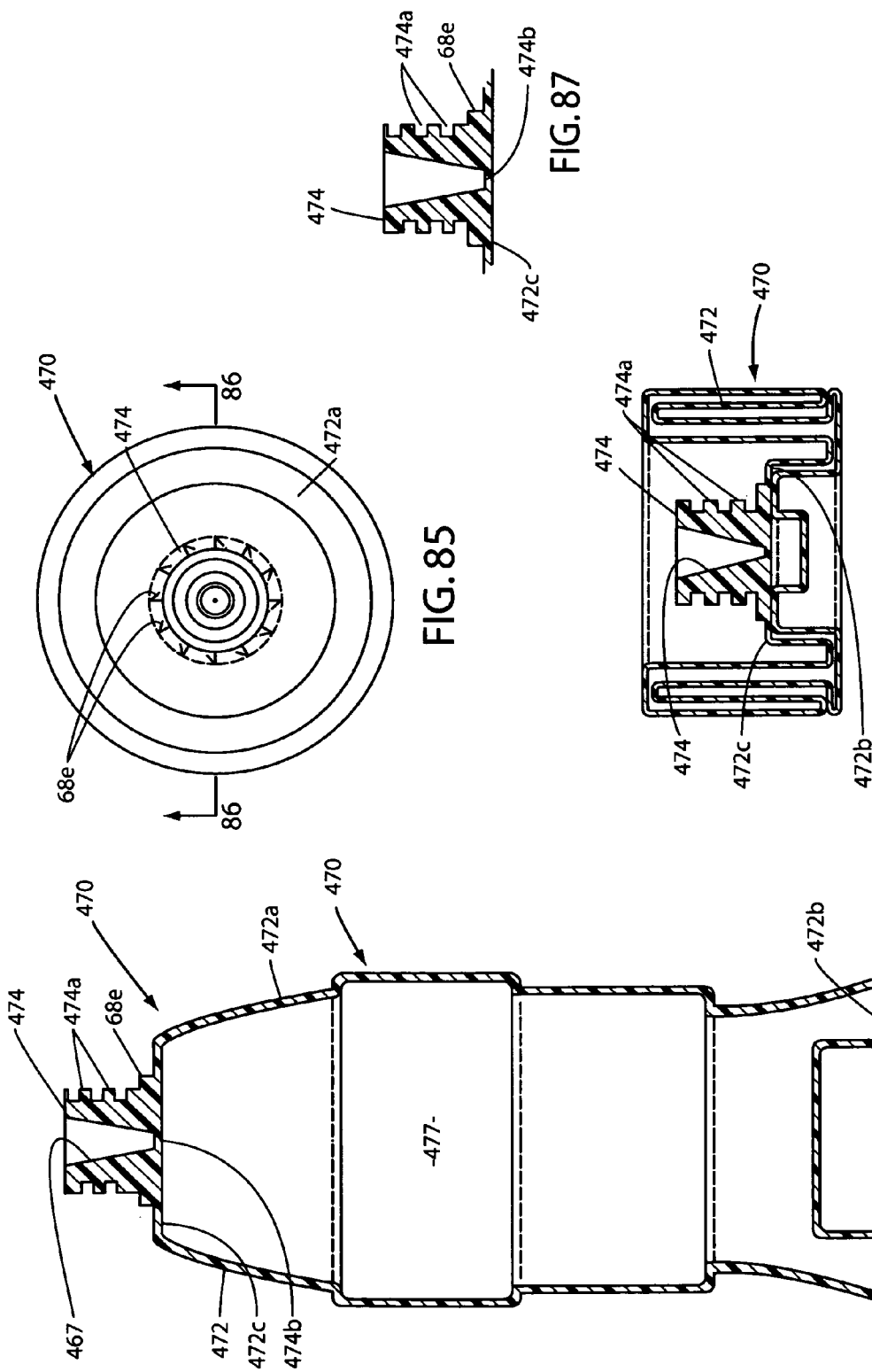

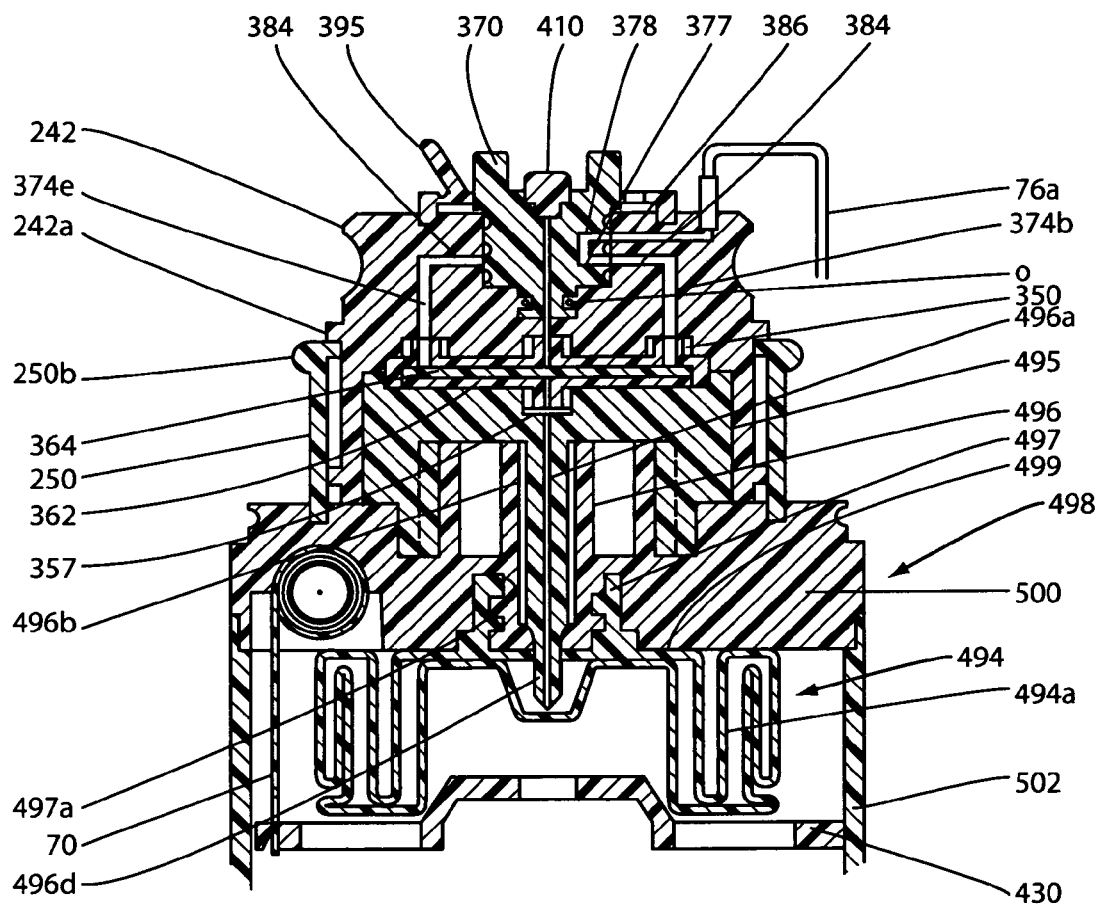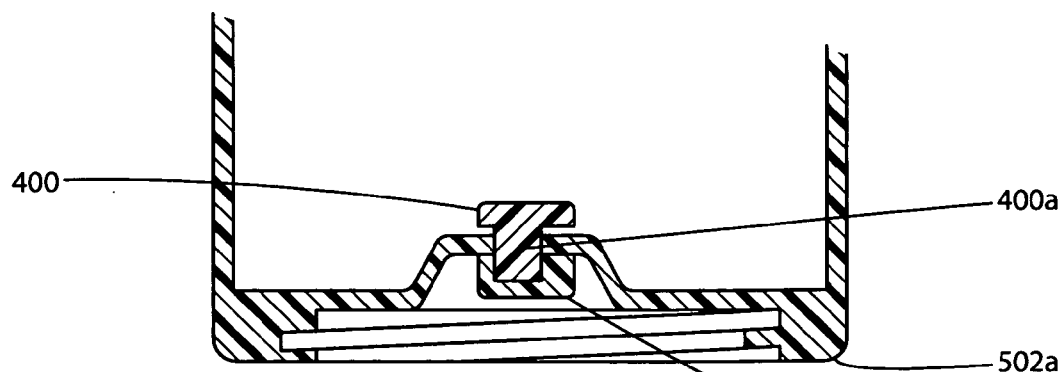
FIG. 90

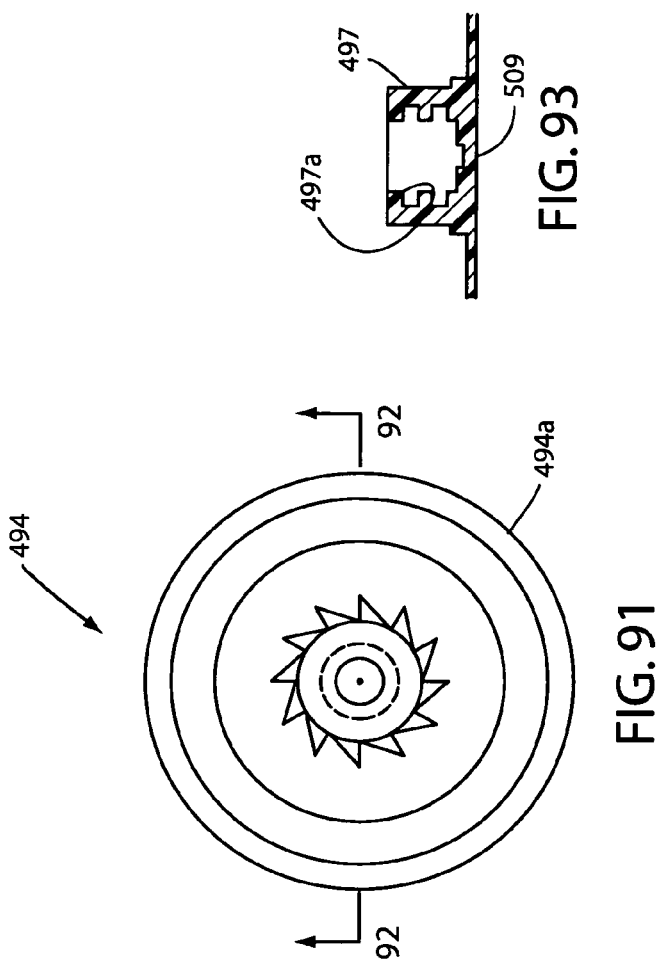
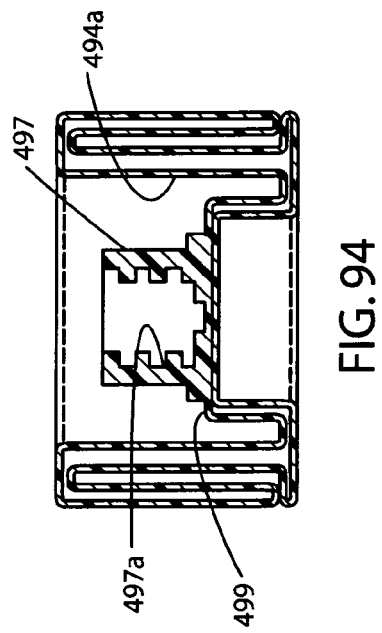
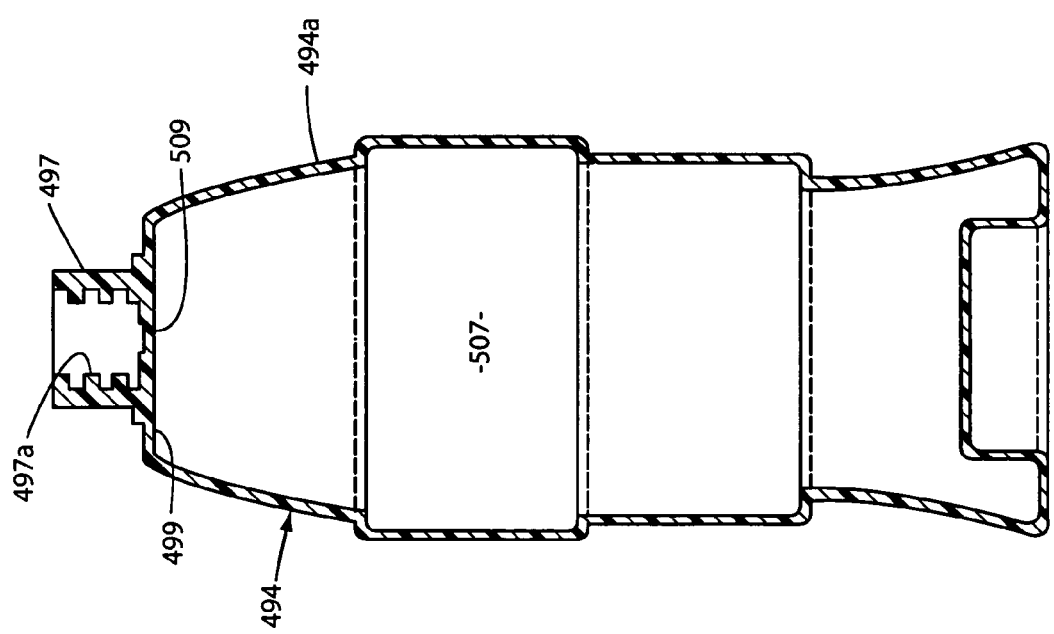

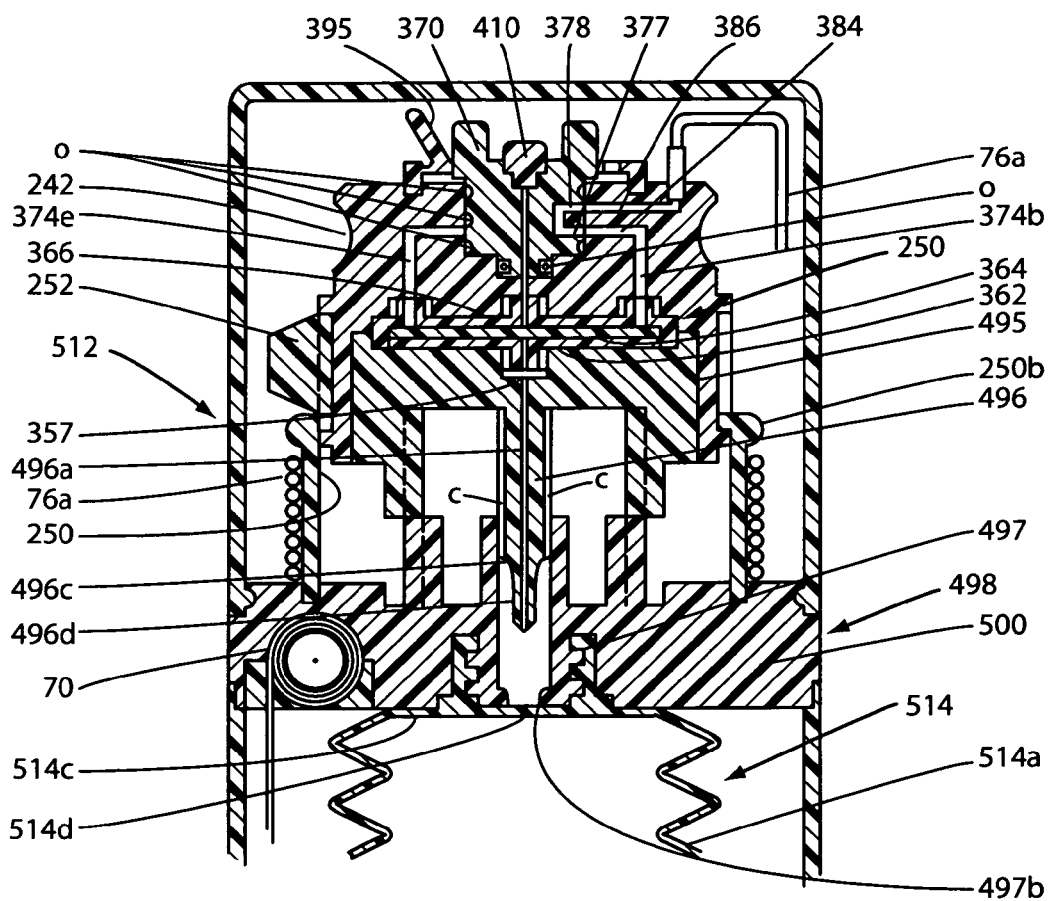
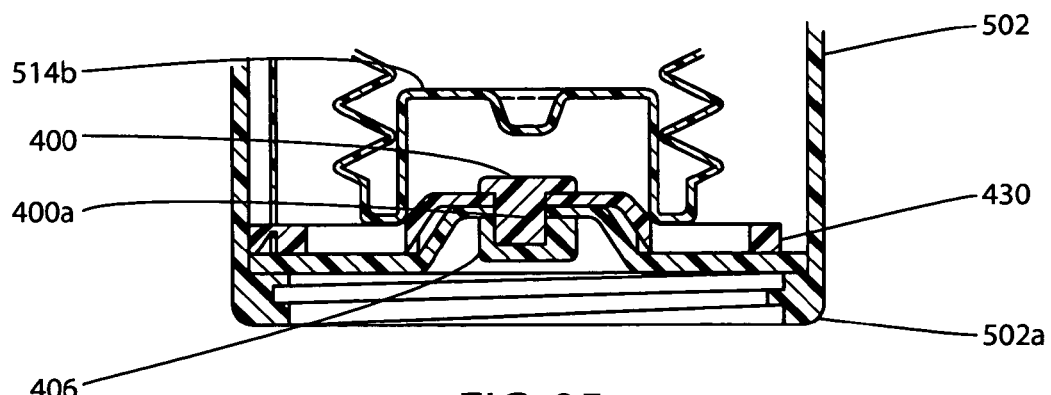
FIG. 95

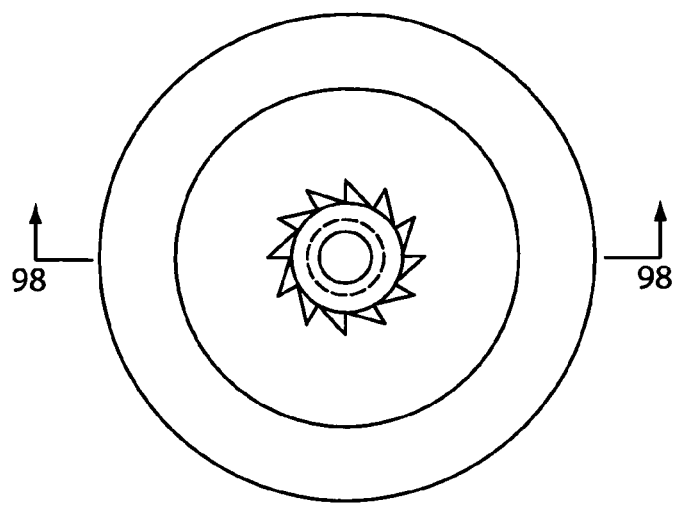
FIG. 97
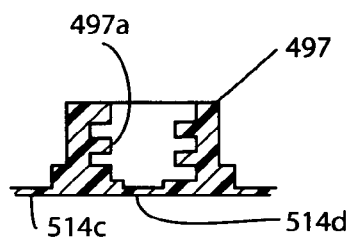
FIG. 99
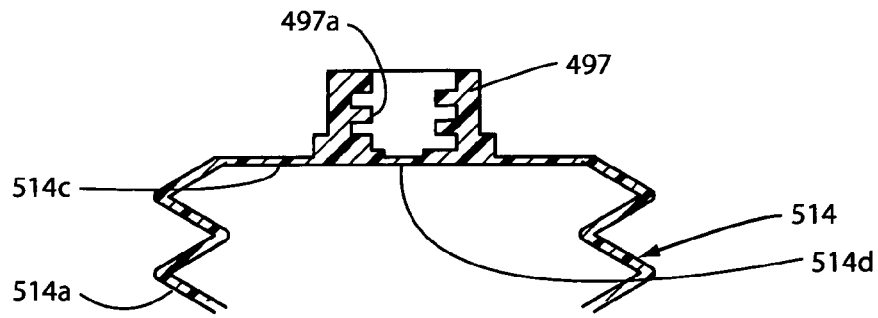
-517-
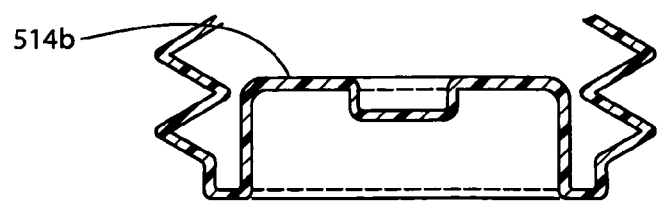
FIG. 98

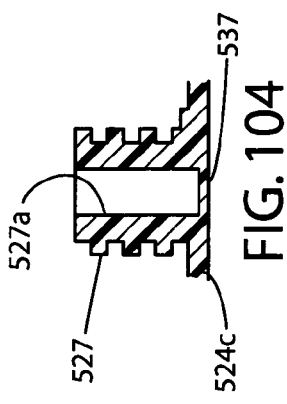
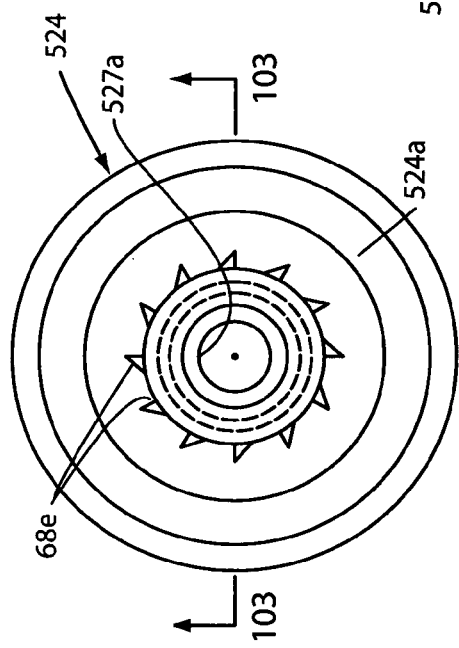
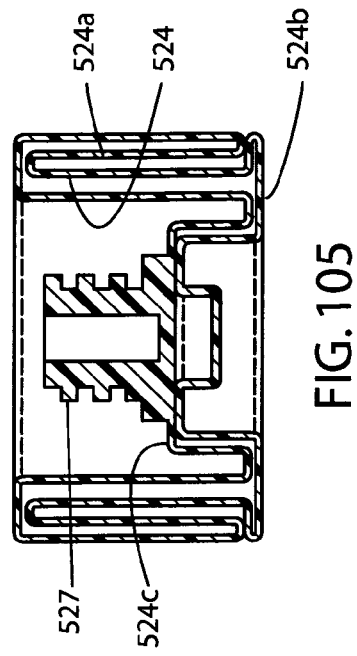
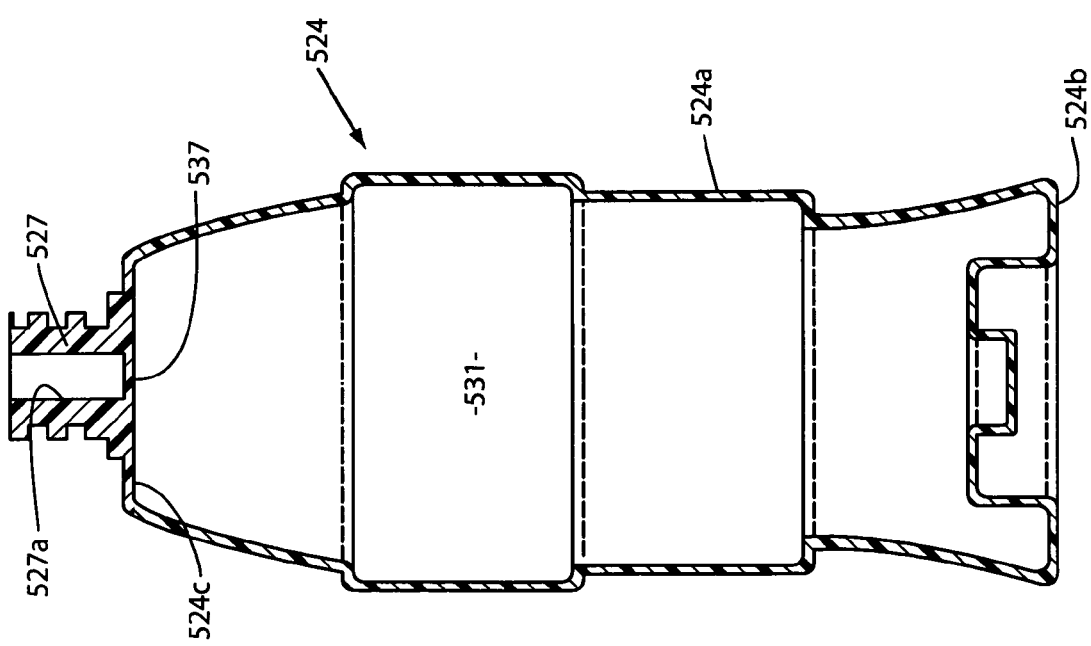

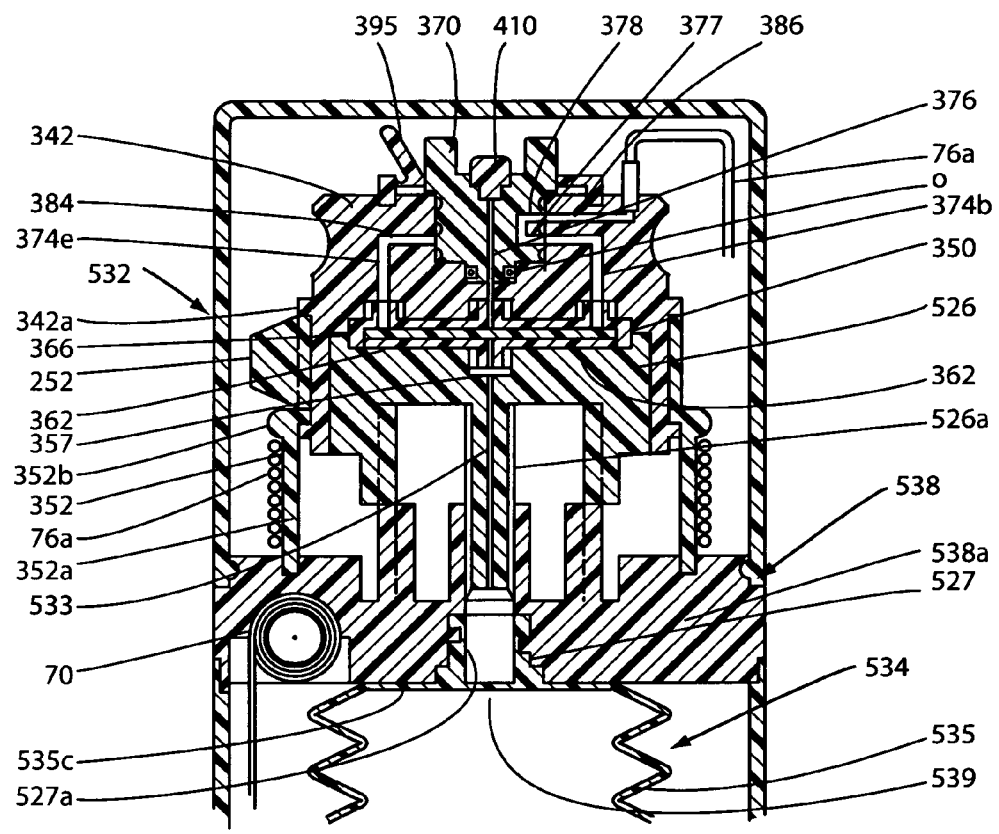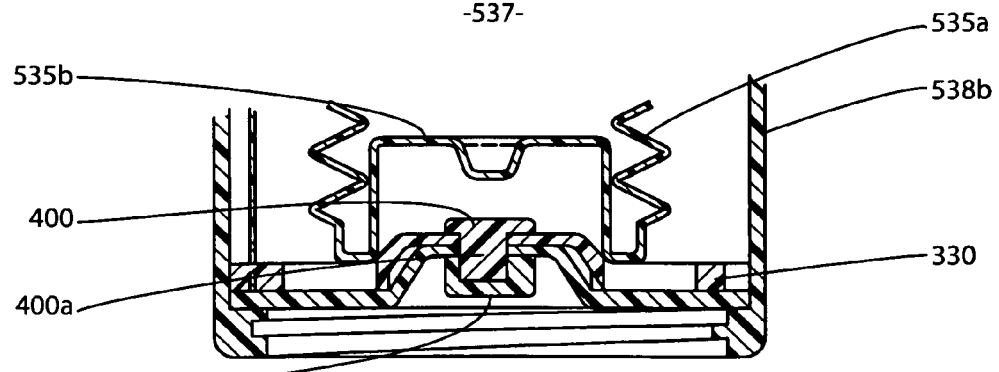
FIG. 106

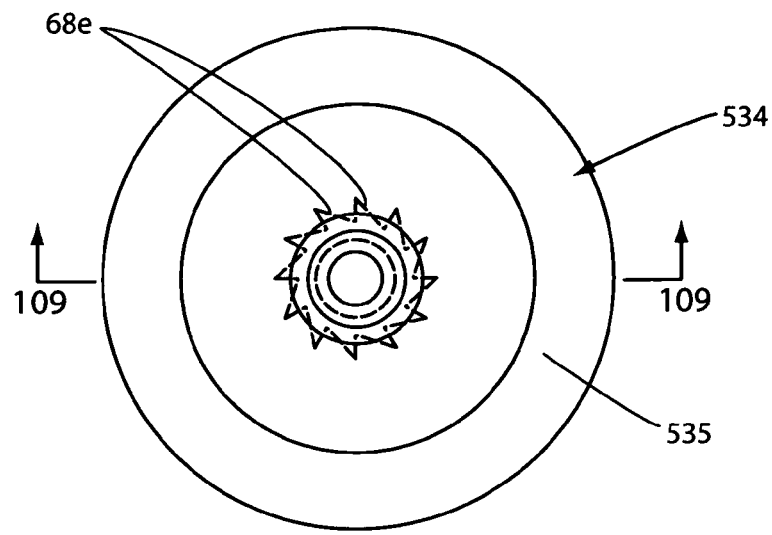
FIG. 108
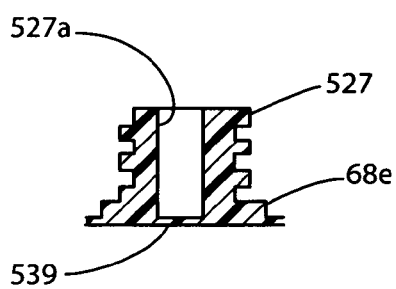
FIG. 110
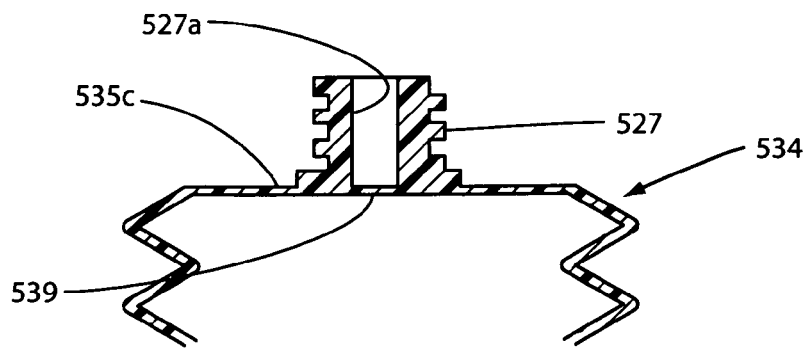
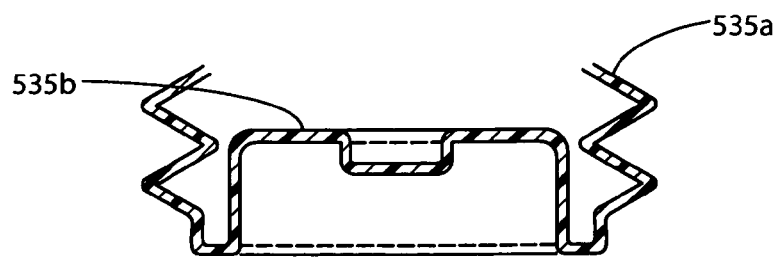
FIG. 109

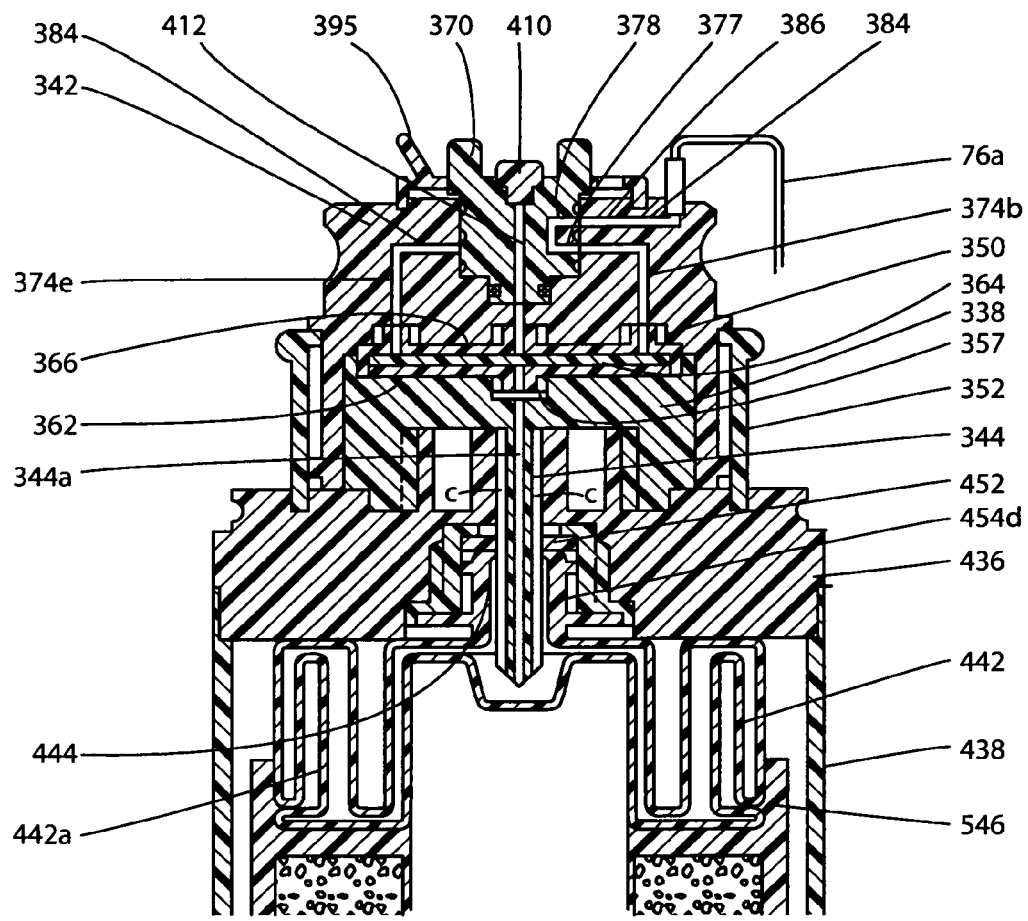
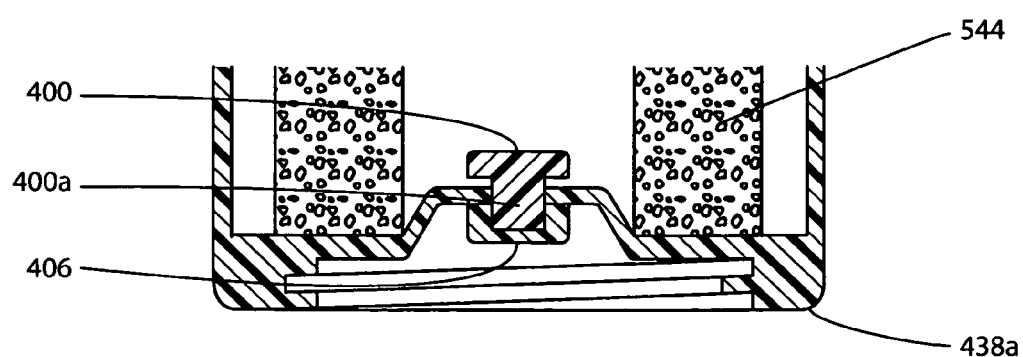
FIG. 112

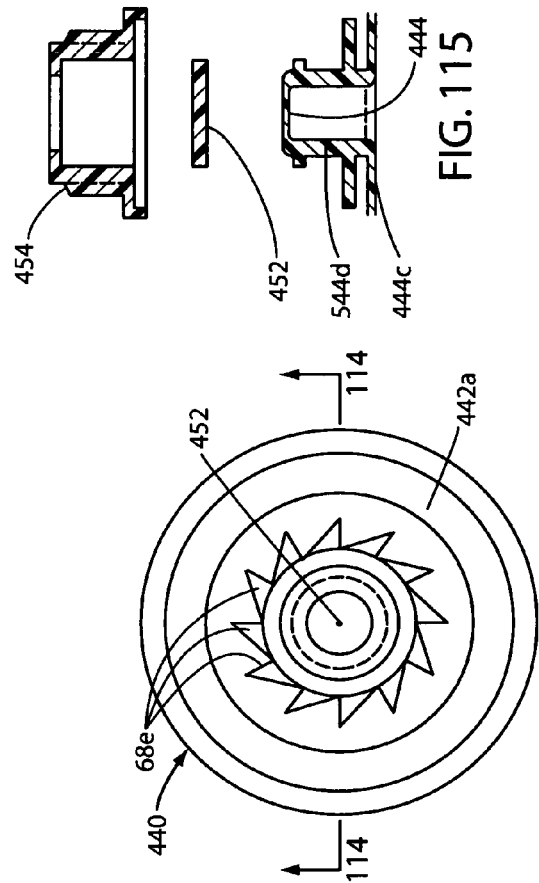
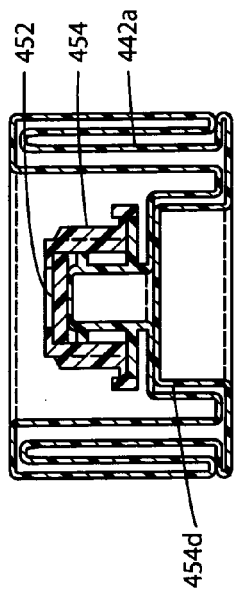
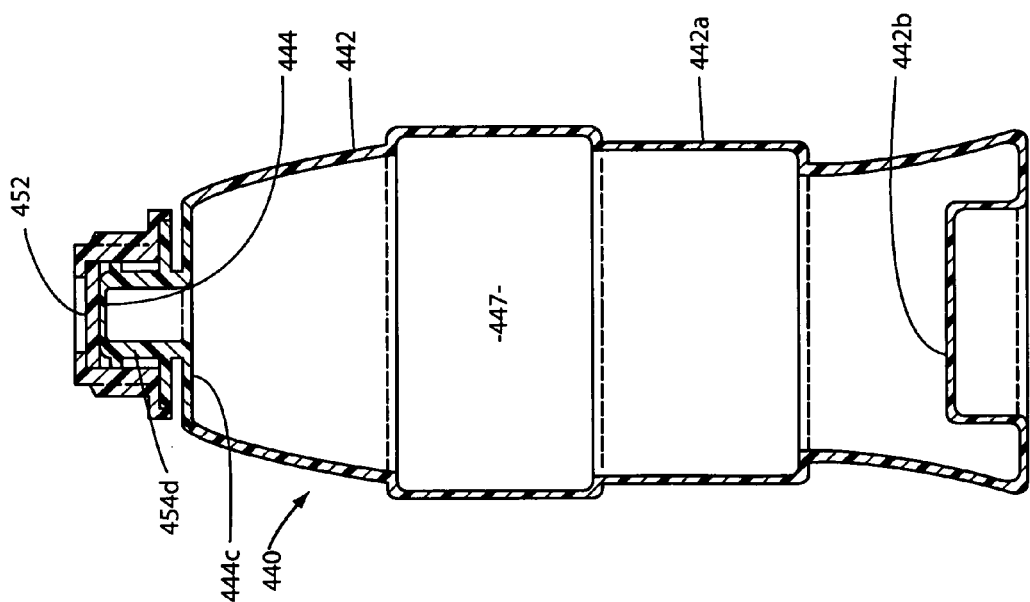

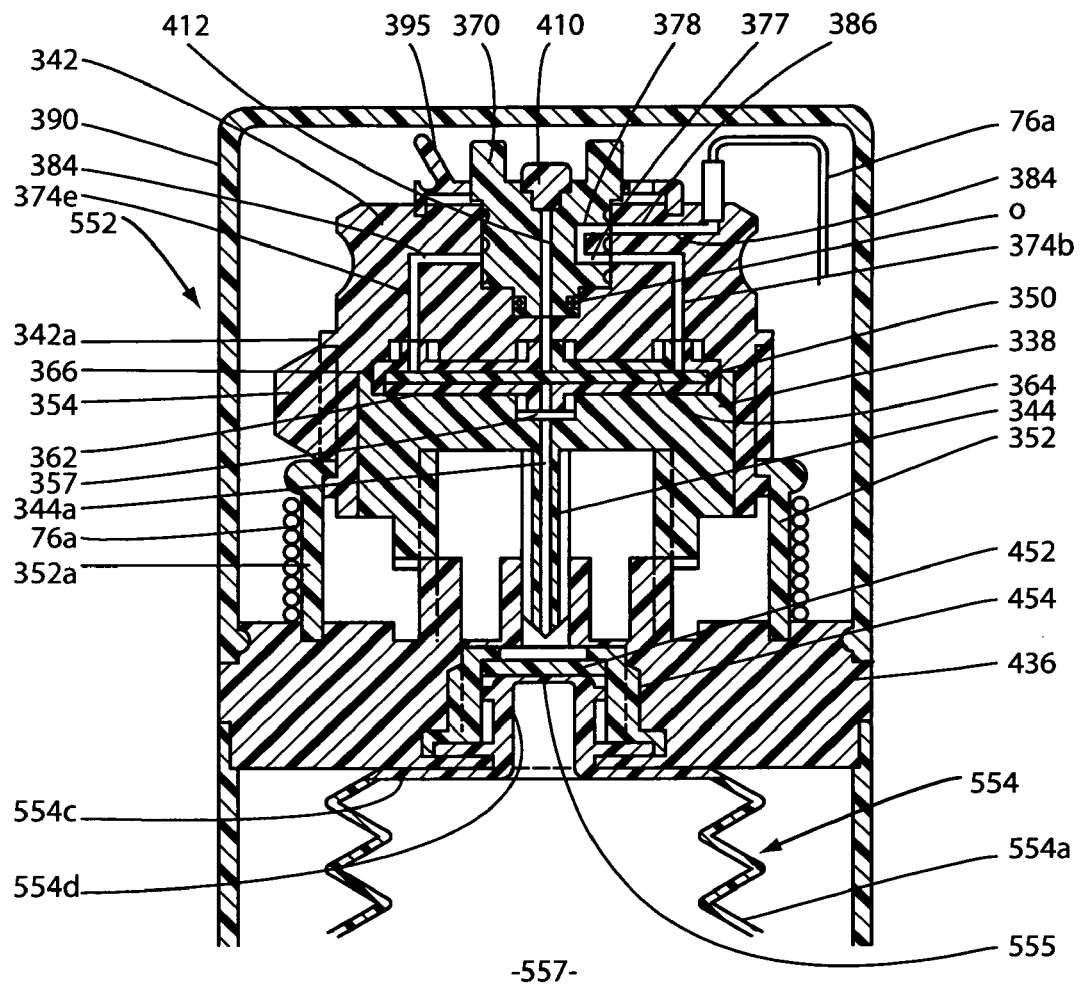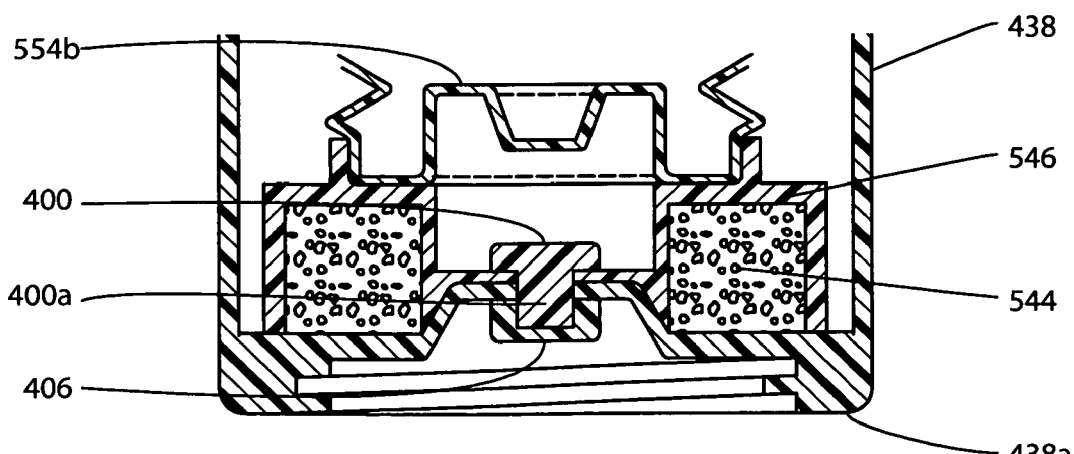
FIG. 117

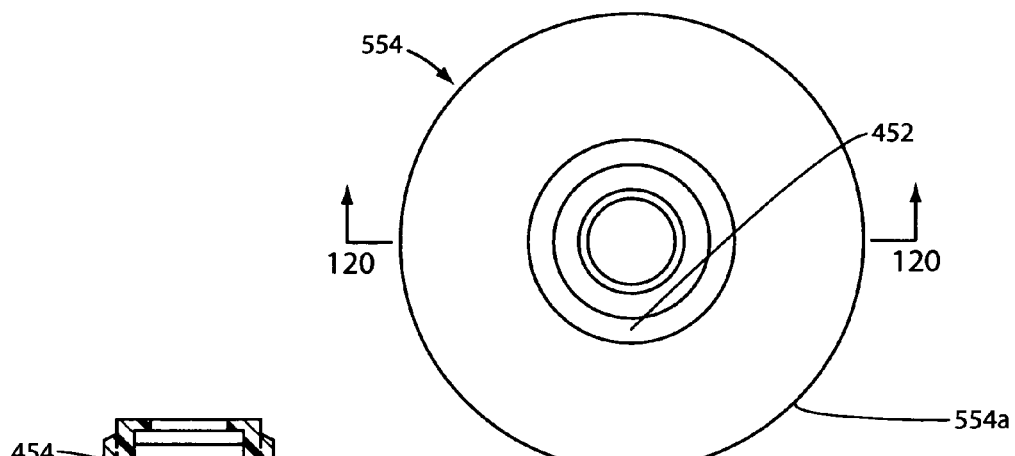
FIG. 119
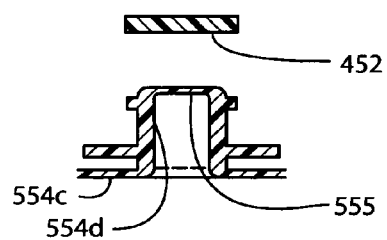
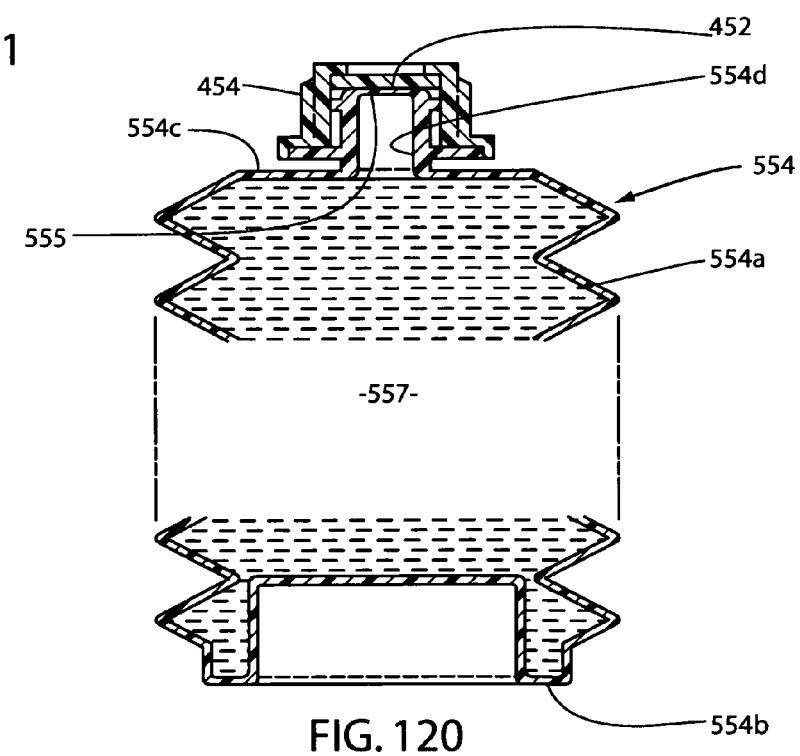
FIG. 121
FIG. 120

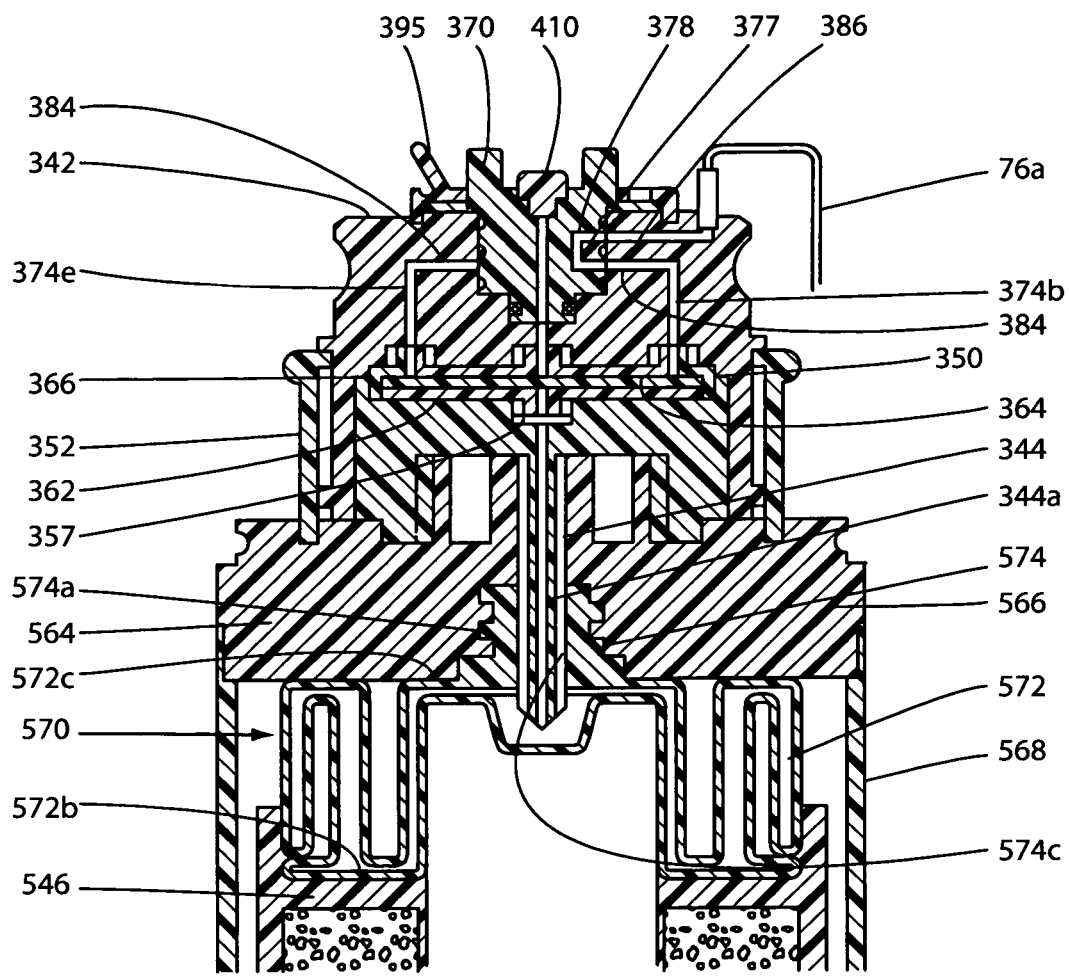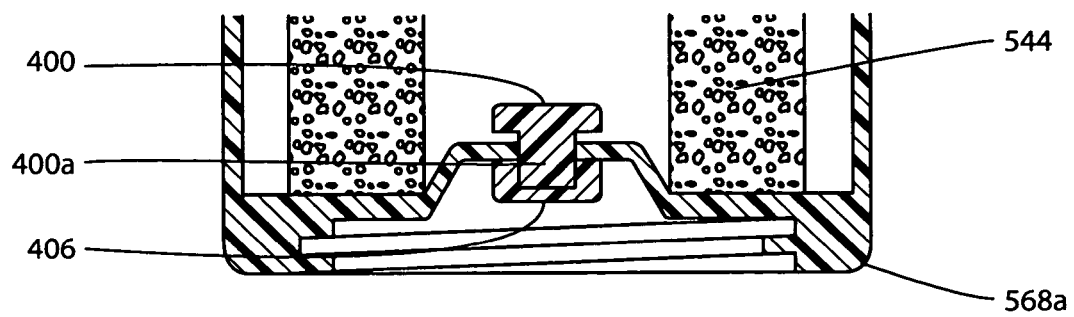
FIG. 123

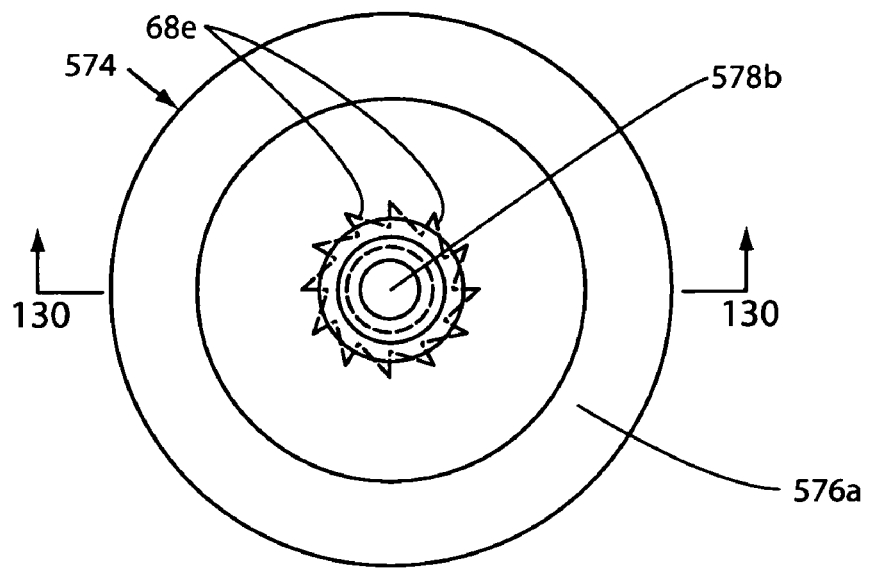
FIG. 129
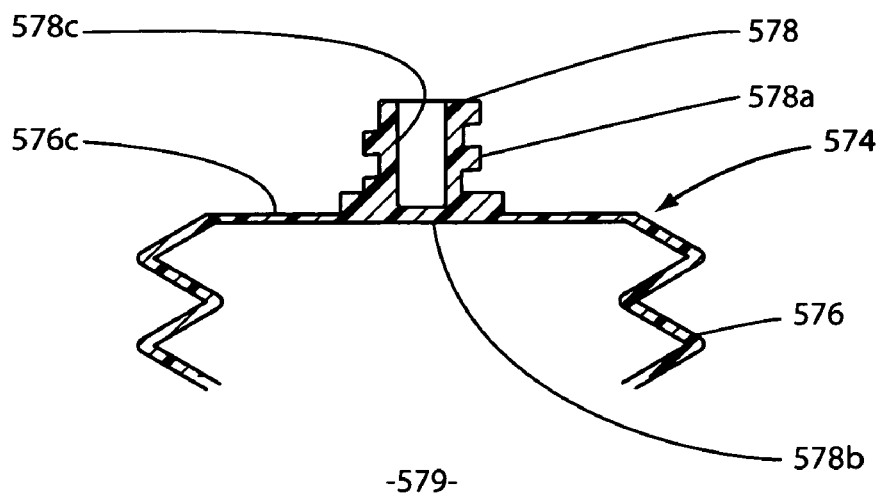
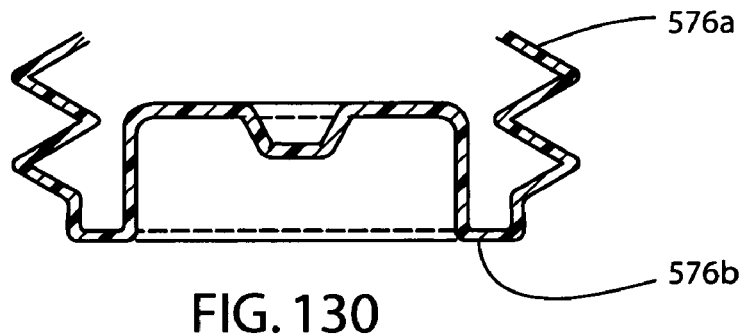
FIG. 130

FLUID DISPENSING APPARATUS

This is a Non-Provisional Application claiming the benefit of co-pending Provisional Application No. 60/783,019 filed Mar. 15, 2006.

FIELD OF THE INVENTION

The present invention relates generally to fluid dispensing apparatus. More particularly, the invention concerns medicament dispensers for dispensing medicinal fluids to ambulatory patients.

DISCUSSION OF THE PRIOR ART

A number of different types of medicament dispensers for dispensing medicaments to ambulatory patients have been suggested in the past. Many of the devices or apparatus seek either to improve or to replace the traditional gravity flow and hypodermic syringe methods which have been the standard for delivery of liquid medicaments for many years.

The prior art gravity flow methods typically involve the use of intravenous administration sets and the familiar flexible solution bag suspended above the patient. Such gravametric methods are cumbersome, imprecise and require bed confinement of the patient. Periodic monitoring of the apparatus by the nurse or doctor is required to detect malfunctions of the infusion apparatus. Accordingly, the prior art devices or apparatus are not well suited for use in those instances where the patient must be transported to a remote facility for treatment.

With regard to the prior art, one of the most versatile and unique fluid delivery apparatus developed in recent years is that developed by one of the present inventors and described in U.S. Pat. No. 5,205,820. The components of this novel fluid delivery apparatus generally include: a base assembly, an elastomeric membrane serving as a stored energy means, fluid flow channels for filling and delivery, flow control means, a cover, and an ullage which comprises a part of the base assembly.

Another prior art patent issued to one of the present applicants, namely U.S. Pat. No. 5,743,879, discloses an injectable medicament dispenser for use in controllably dispensing fluid medicaments such as insulin, anti-infectives, analgesics, oncolylotics, cardiac drugs biopharmaceuticals, and the like from a pre-filled container at a uniform rate. The dispenser, which is quite dissimilar in construction and operation from that of the present invention, includes a stored energy source in the form of a compressively deformable, polymeric, elastomeric member that provides the force necessary to controllably discharge the medicament from a pre-filled container, which is housed within the body of the apparatus. After having been deformed, the polymeric, elastomeric member will return to its starting configuration in a highly predictable manner.

SUMMARY OF THE INVENTION

By way of brief summary, one form of the dispensing apparatus of the present invention for dispensing medicaments to a patient comprises a supporting structure; a carriage assembly interconnected with the supporting structure for movement between a first position and a second position; a pre-filled collapsible container carried by the carriage assembly, the collapsible container having accessing means for accessing the reservoir comprising a frangible member in the form of a pierceable member or shearable member. The apparatus also includes guide means connected to the supporting structure for guiding travel of the carriage assembly between the first position and said second positions; a stored energy source operably associated with the carriage assembly for moving the carriage assembly between the first and second positions; and an administration set, including an administration line interconnected with the outlet port of the collapsible reservoir.

With the forgoing in mind, it is an object of the present invention to provide a compact fluid dispenser for use in controllably dispensing fluid medicaments to ambulatory patients, such as, antibiotics, blood clotting agents, analgesics, KVO, artificial blood substitutes, resuscitation fluids, internal nutritional solutions, biologics, and like beneficial agents from pre-filled or field-filled containers at a uniform rate.

Another object of the invention is to provide a small, compact pre-filled fluid dispenser that is aseptically filled and sealed at the time of manufacture.

Another object of the invention is to provide an apparatus that is of simple construction that can be used in the field with a minimum amount of training.

Another object of the invention is to provide a dispenser in which a stored energy source is provided in the form of a compressible, expandable or retractable member of novel construction that provides the force necessary to continuously and uniformly expel fluid from the apparatus reservoir.

Another object of the invention is to provide a dispenser of the class described which includes a fluid flow control assembly that precisely controls the flow of the medicament solution to the patient. Uniquely, the container is formed as a unitary structure that includes a collapsible side wall and a pierceable closure wall that isolates the beneficial agents contained within the container reservoir from external contaminants.

Another object of the invention is to provide a dispenser that includes precise variable flow rate selection.

Another object of the invention is to provide a fluid dispenser of simple construction, which embodies an integrally formed, collapsible, pre-filled drug container that contains the beneficial agents to be delivered to the patient.

Another object of the invention is to provide a fluid dispenser of the class described which is compact, lightweight, is easy for ambulatory patients to use, is fully disposable, transportable and is extremely reliable in operation.

Another object of the invention is to provide a fluid dispenser as described in the preceding paragraphs that is easy and inexpensive to manufacture in large quantities.

BRIEF DESCRIPTION OF THE DRAWINGS

FIG. 3 is an enlarged, longitudinal, cross-sectional view of the fluid dispensing apparatus illustrated in FIG. 1.

FIG. 4A is an enlarged, fragmentary, longitudinal, cross-sectional view of the left-hand portion of the apparatus shown in FIG. 3.

FIG. 4B is a fragmentary, longitudinal, cross-sectional view similar to FIG. 4A, but showing the various components of the apparatus as they appear following delivery to the patient of the fluid contained within the apparatus reservoir.

FIG. 38 is a side-elevational view of one form of the control shaft of the flow control means of the invention.

FIG. 39 is a view taken along lines 39-39 of FIG. 38.

FIG. 40 is a view taken along lines 40-40 of FIG. 38.

FIG. 41 is an enlarged, cross-sectional view taken along lines 41-41 of FIG. 38.

FIG. 42 is an enlarged, side-elevational view of one form of the spring knife of the invention that is carried within cavities formed in the control shaft as shown in FIG. 41.

FIG. 43 is a view taken along lines 43-43 of FIG. 42.

FIG. 52 is a longitudinal, cross-sectional view of an alternate form of the fluid dispensing apparatus of the invention showing the reservoir in a pre-filled condition.

FIG. 53A is a fragmentary, longitudinal, cross-sectional view of the left-hand portion of the apparatus shown in FIG. 52.

FIG. 54 is a cross-sectional view of the fluid reservoir assembly of this latest form of the invention.

FIG. 55 is a cross-sectional view showing the fluid reservoir assembly as it appears in a substantially empty condition following delivery to the patient of the fluid contained within the reservoir.

FIG. 67A is a longitudinal, cross-sectional view of yet another form of the fluid dispensing apparatus of the invention.

FIG. 68A is a generally perspective view of the fluid dispensing apparatus of the invention shown in FIG. 68 as it appears following removal of the closure cap.

FIG. 68B is a fragmentary, generally perspective, exploded view of the upper portion of the fluid dispensing apparatus of the invention shown in FIG. 68 as it appears following removal of the tear strip.

FIG. 70 is a foreshortened, longitudinal, cross-sectional view of still another form of the fluid dispensing apparatus of the invention showing the reservoir in a filled condition.

FIG. 71 is a foreshortened, longitudinal, cross-sectional view similar to FIG. 70, but showing the various components of the apparatus as they appear following delivery to the patient of the fluid contained within the apparatus reservoir which is shown in a substantially empty condition.

FIG. 74 is a top plan view of the collapsible container of this alternate embodiment of the invention.

FIG. 75 is a cross-sectional view taken along lines 75-75 of FIG. 74.

FIG. 76 is an exploded, cross-sectional view of the reservoir access assembly of this latest form of the invention.

FIG. 77 is a fragmentary, cross-sectional view of the collapsible container as it appears in the collapsed substantially empty condition.

FIG. 78 is a foreshortened, longitudinal, cross-sectional view of an alternate form of the fluid dispensing apparatus of the invention showing the reservoir in a pre-filled condition.

FIG. 82A is a foreshortened, longitudinal, cross-sectional view of yet another alternate form of the fluid dispensing apparatus of the invention showing the reservoir in a pre-filled condition.

FIG. 82B is a foreshortened, longitudinal, cross-sectional view, similar to FIG. 83A, but showing the various components of the apparatus as they appear following delivery to the patient of the fluid contained within the apparatus reservoir which is substantially empty.

FIG. 85 is a top plan view of the collapsible container of this alternate embodiment of the invention.

FIG. 86 is a cross-sectional view taken along lines 86-86 of FIG. 85.

FIG. 87 is a cross-sectional view of the reservoir access assembly of this latest form of the invention.

FIG. 88 is a fragmentary, cross-sectional view of the collapsible container as it appears in the collapsed configuration.

FIG. 90 is a foreshortened, longitudinal, cross-sectional view, similar to FIG. 89, but showing the various components of the apparatus as they appear following delivery to the patient of the fluid contained within the apparatus reservoir which is substantially empty.

FIG. 91 is a top plan view of the collapsible container of this alternate embodiment of the invention.

FIG. 92 is a cross-sectional view taken along lines 92-92 of FIG. 91.

FIG. 93 is a cross-sectional view of the luer-like reservoir access assembly of this latest form of the invention.

FIG. 94 is a fragmentary, cross-sectional view of the collapsible container as it appears in the collapsed configuration.

FIG. 95 is a foreshortened, longitudinal, cross-sectional view of yet another alternate form of the fluid dispensing apparatus of the invention showing the reservoir in a pre-filled condition.

FIG. 97 is a top plan view of the collapsible container of this alternate embodiment of the invention.

FIG. 98 is a cross-sectional view taken along lines 98-98 of FIG. 97.

FIG. 99 is a cross-sectional view of the luer-like reservoir access assembly of this latest form of the invention.

FIG. 102 is a top plan view of the collapsible container of this alternate embodiment of the invention.

FIG. 103 is a cross-sectional view taken along lines 103-103 of FIG. 102.

FIG. 104 is a cross-sectional view of the luer-like reservoir access assembly of this latest form of the invention.

FIG. 105 is a fragmentary, cross-sectional view of the collapsible container as it appears in the collapsed configuration.

FIG. 106 is a foreshortened, longitudinal, cross-sectional view of still another alternate form of the fluid dispensing apparatus of the invention showing the reservoir in a pre-filled condition.

FIG. 107 is a foreshortened, longitudinal, cross-sectional view similar to FIG. 106 but showing the various components of the apparatus as they appear following delivery to the patient of the fluid contained within the apparatus reservoir which is shown substantially empty.

FIG. 108 is a top plan view of the collapsible container of this alternate embodiment of the invention.

FIG. 109 is a cross-sectional view taken along lines 109-109 of FIG. 108.

FIG. 110 is a cross-sectional view of the luer-like reservoir access assembly of this latest form of the invention.

FIG. 111 is a foreshortened, longitudinal, cross-sectional view of still another alternate form of the pre-filled reservoir type fluid dispensing apparatus of the invention that includes a sponge-like stored energy source.

FIG. 112 is a foreshortened, longitudinal, cross-sectional view, similar to FIG. 111, but showing the various components of the apparatus as they appear following delivery to the patient of the fluid contained within the apparatus reservoir showing the reservoir substantially empty.

FIG. 113 is a top plan view of the collapsible container of this alternate embodiment of the invention.

FIG. 114 is a cross-sectional view taken along lines 114-114 of FIG. 113.

FIG. 115 is a cross-sectional, exploded view of the luer-like reservoir access assembly of this latest form of the invention.

FIG. 116 is a fragmentary, cross-sectional view of the collapsible container as it appears in the collapsed configuration.

FIG. 117 is a foreshortened, longitudinal, cross-sectional view of still another alternate form of the pre-filled reservoir type fluid dispensing apparatus of the invention that includes a sponge-like stored energy source.

Figure 118:
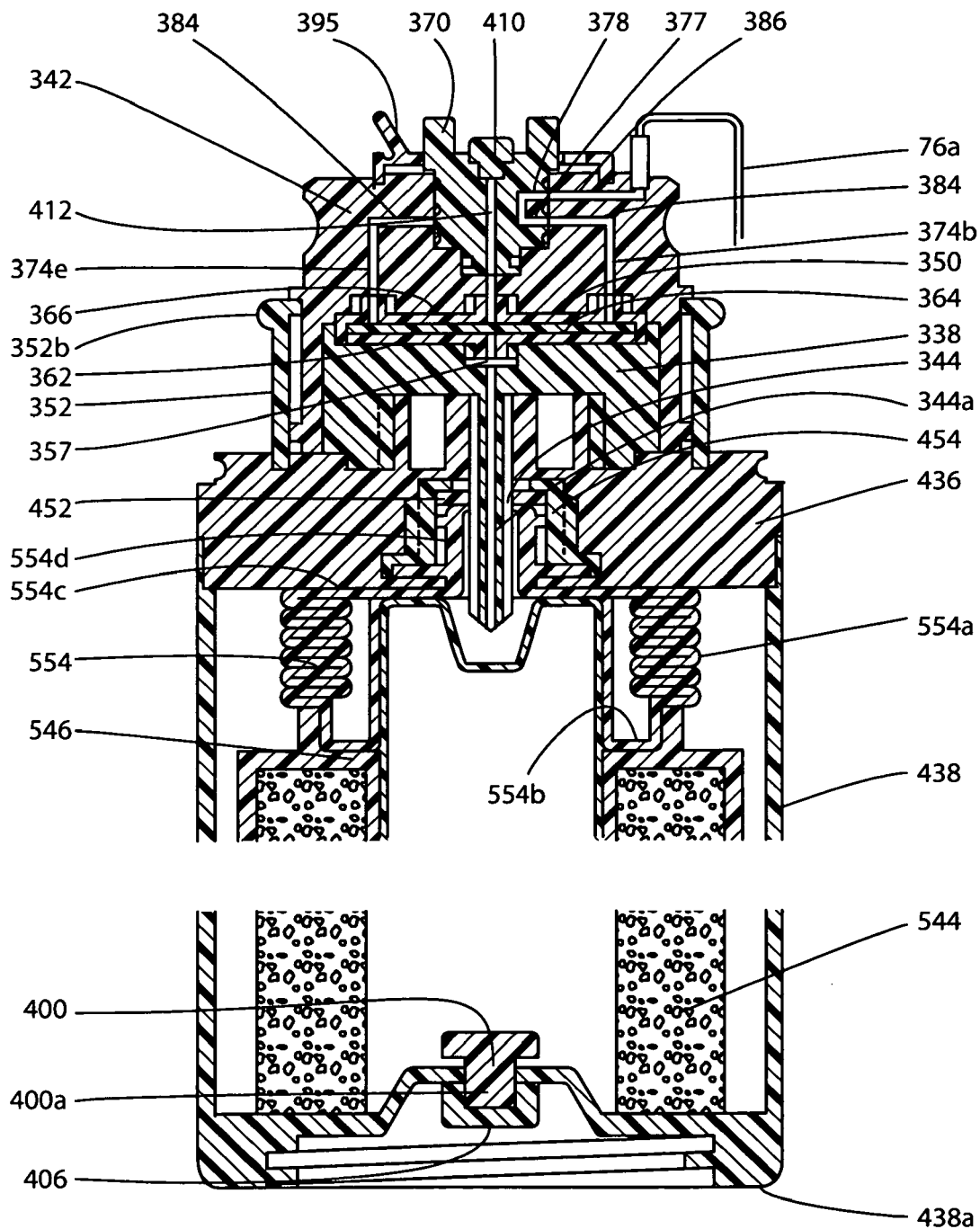

FIG. 118 is a foreshortened, longitudinal, cross-sectional view, similar to FIG. 117, but showing the various components of the apparatus as they appear following delivery to the patient of the fluid contained within the apparatus reservoir which is shown in a substantially empty condition.

FIG. 119 is a top plan view of the collapsible container of this alternate embodiment of the invention.

FIG. 120 is a partial cross-sectional view taken along lines 120-120 of FIG. 119.

FIG. 121 is a cross-sectional, exploded view of the luer-like reservoir access assembly of this latest form of the invention.

Figure 122:
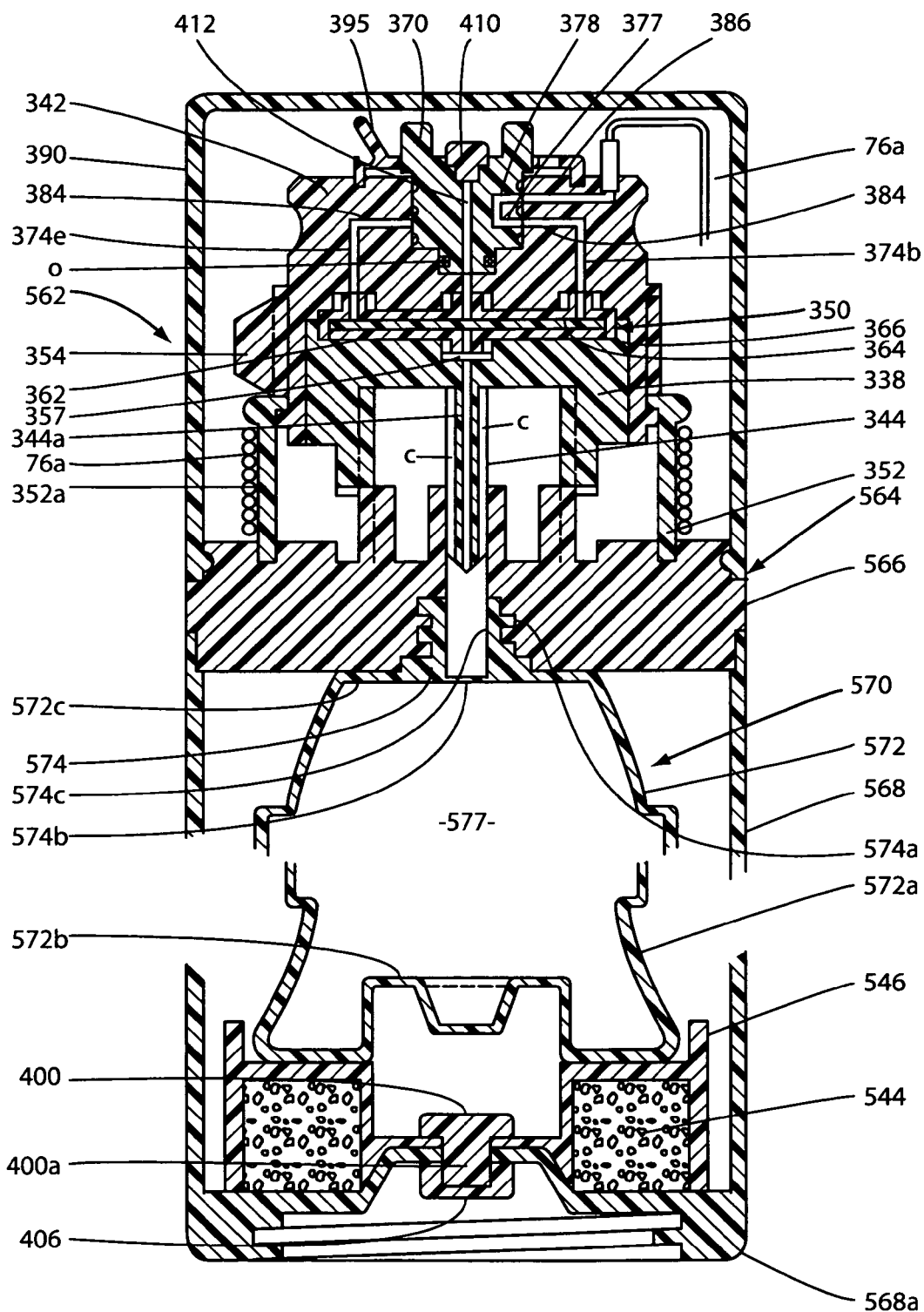

FIG. 122 is a foreshortened, longitudinal, cross-sectional view of yet another alternate form of the pre-filled reservoir type fluid dispensing apparatus of the invention that includes a sponge-like stored energy source.

FIG. 123 is a foreshortened, longitudinal, cross-sectional view, similar to FIG. 122, but showing the various components of the apparatus as they appear following delivery to the patient of the fluid contained within the apparatus reservoir which appears in a substantially empty condition.

Figure 124:
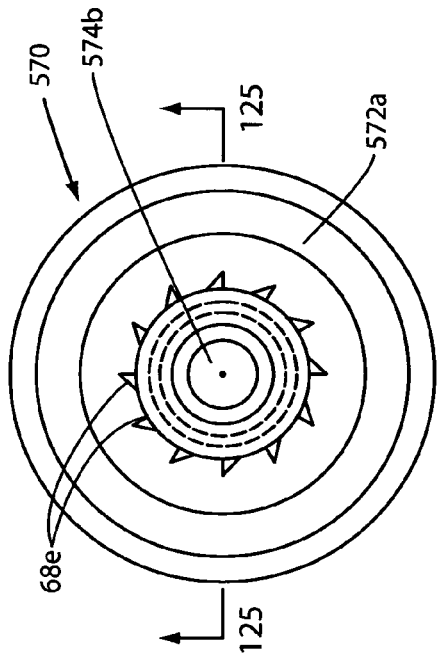

FIG. 124 is a top plan view of the collapsible container of this alternate embodiment of the invention.

Figure 125:
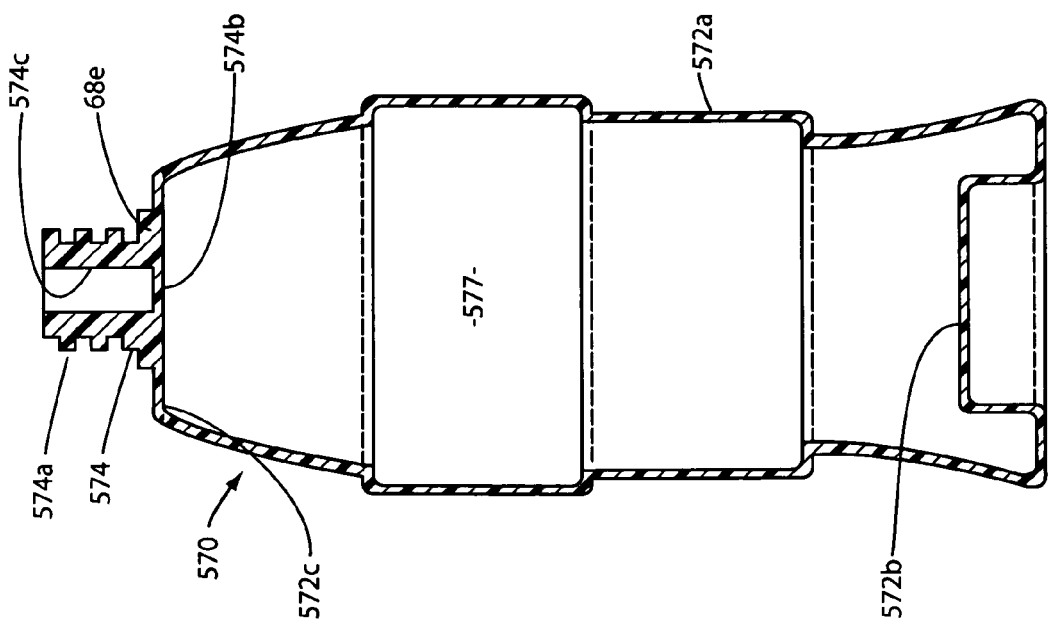

FIG. 125 is a cross-sectional view taken along lines 125-125 of FIG. 124.

Figure 126:
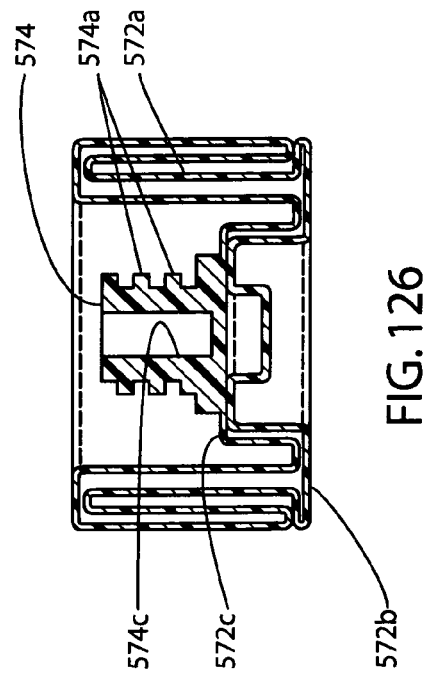

FIG. 126 is a fragmentary, cross-sectional view of the collapsible container as it appears in the collapsed configuration.

Figure 127:
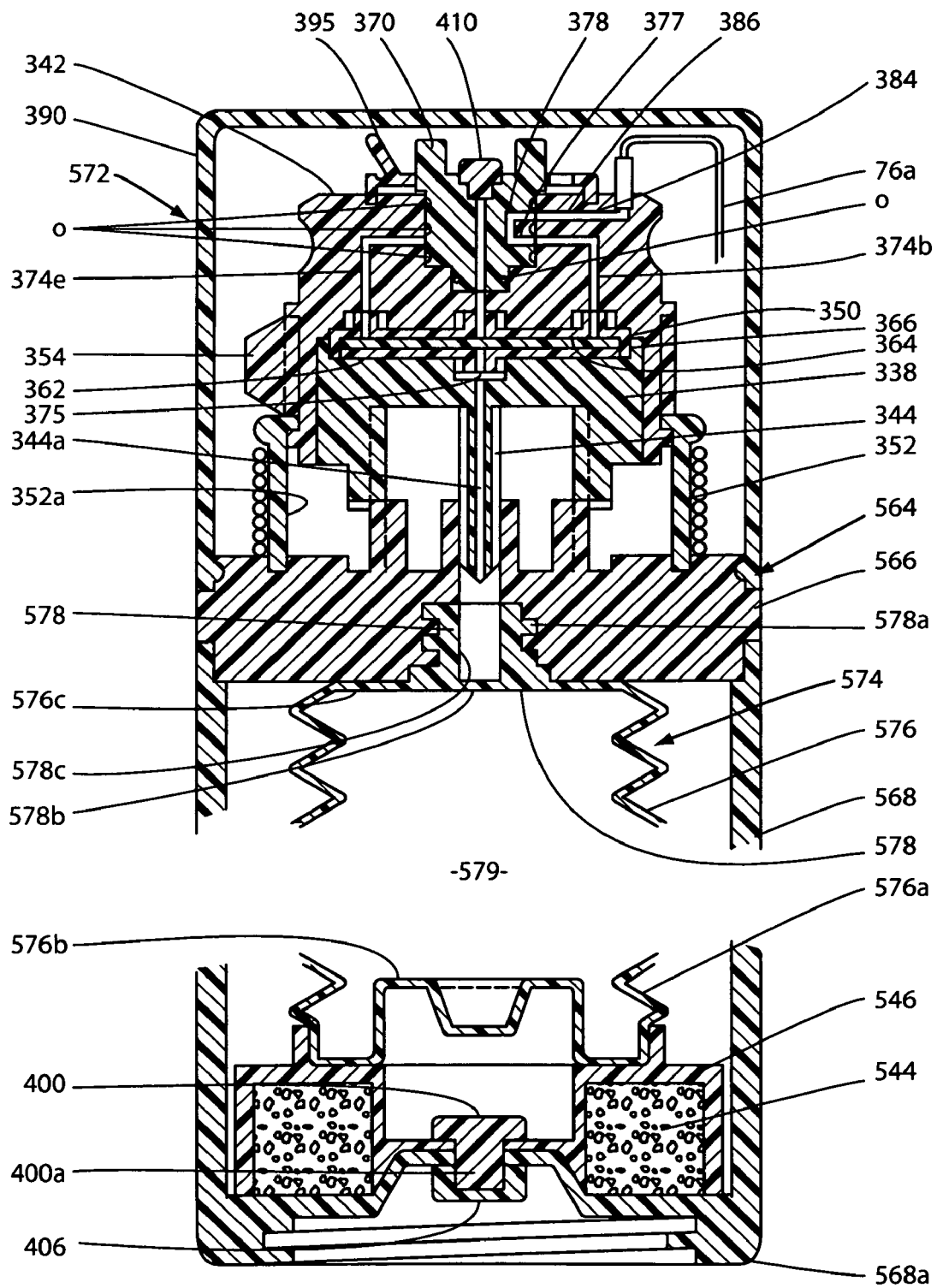

FIG. 127 is a foreshortened, longitudinal, cross-sectional view of still another alternate form of the pre-filled reservoir type fluid dispensing apparatus of the invention that includes a sponge-like stored energy source.

Figure 128:
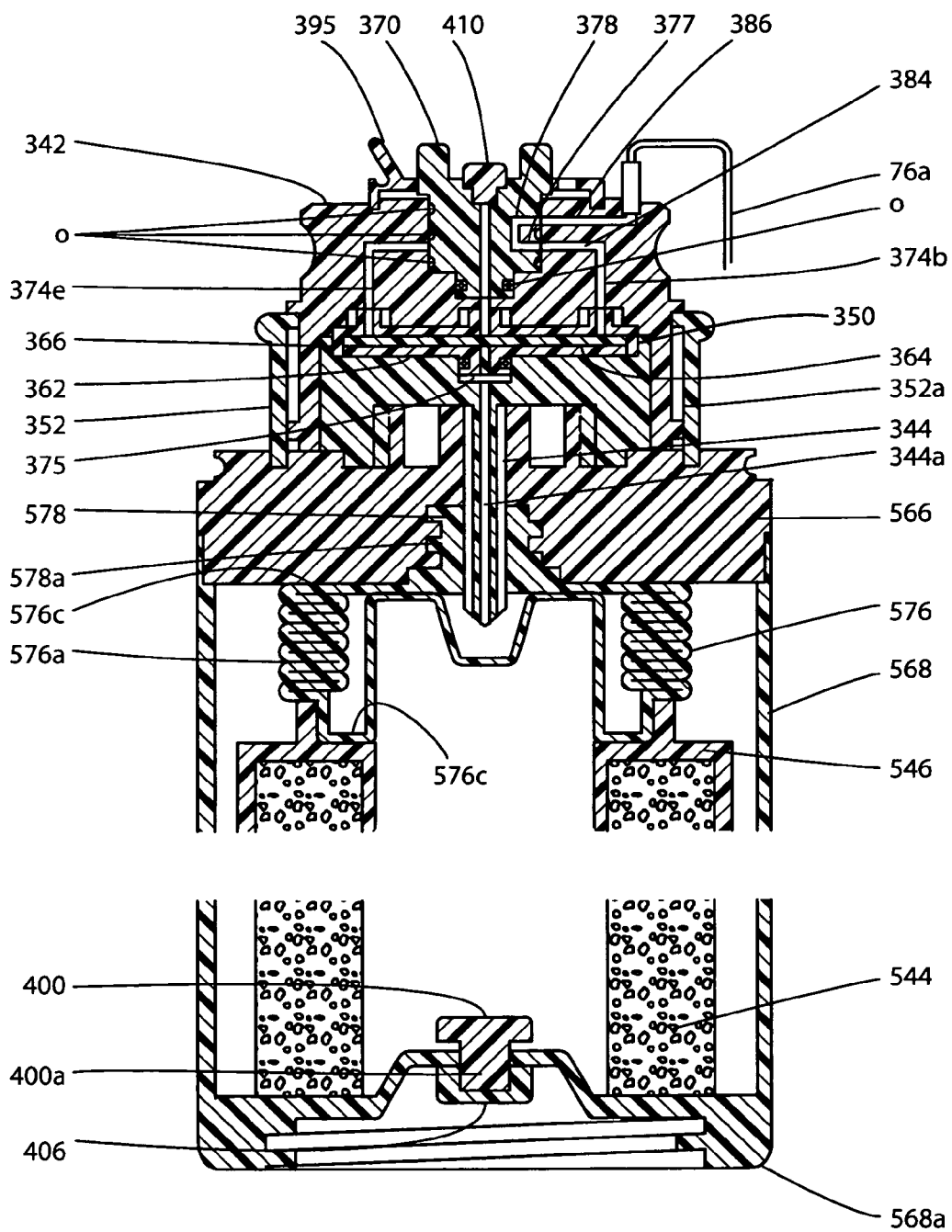

FIG. 128 is a foreshortened, longitudinal, cross-sectional view, similar to FIG. 127, but showing the various components of the apparatus as they appear following delivery to the patient of the fluid contained within the apparatus reservoir which appears in a substantially empty condition.

FIG. 129 is a top plan view of the collapsible container of this alternate embodiment of the invention.

FIG. 130 is a partial cross-sectional view taken along lines 130-130 of FIG. 129.

DESCRIPTION OF THE INVENTION

Definitions

As used herein, the following terms have the following meanings:

Unitary Container

A closed container formed from a single component.

Continuous/Uninterrupted Wall.

A wall having no break in uniformity or continuity.

Patient

Individual seeking medical care.

Hermetically Sealed Container

A container that is designed and intended to be secure against the entry of microorganisms and to maintain the safety and quality of its contents after pressurizing.

Biologic

A virus, therapeutic serum, toxin, antitoxin, vaccine, blood, blood component or derivative, allergenic product, or analogous product applicable to the prevention, treatment or cure of diseases or injuries of man.

Drug
As defined by the Food, Drug and Cosmetic Act, drugs are "articles (other than food) intended for the use in the diagnosis, cure, mitigation, treatment, or prevention of disease in man or other animals, or to affect the structure or any function."

Drug Product
A finished dosage form (e.g. tablet, capsule, or solution) that contains the active drug ingredient usually combined with inactive ingredients.

Artificial Blood Substitutes
Blood Substitutes are used to fill fluid volume and/or carry oxygen and other gases in the cardiovascular system. These include volume expanders for inert products, and oxygen therapeutics for oxygen-carrying products.

Resuscitation Fluids
Infusion of hyperosmotic-hyperoncotic solutions such as hypertonic saline dextran (HSD) as used for resuscitation of traumatic shock and perioperative volume support or as an adjunct to other conventional isotonic crystalloid solutions. Where hypotension is caused by myocardial depression, pathological vasodilatation and extravascation of circulating volume due to widespread capillary leak, a resuscitative effort is attempted to correct the absolute and relative hypovolemia by refilling the vascular tree. Here resuscitation with a small volume of hypertonic-hyperoncotic solution allows systemic and splanchnic hemodynamic and oxygen transport recovery, without an increase in pulmonary artery pressure. Alternate types of normotonic, hyperoncotic, hypertonic, and hypertonic-hyperoncotic solutions can be used for systemic hemodynamic recovery.

KVO
KVO—keeping-the-vein-open in an IV set up, a phrase that refers to the flow rate of a maintenance IV line established as a prophylactic access.

Nutritionals
Dietary supplemental enteral nutrition support feeding solutions used for nasoenteric application typically used in nasogastric, nasoduodenal and nasojejunal or intravenous routes of administration.

Beneficial Agent
The term beneficial agent can include any substance or compound that is biologically active and includes any physiologically or pharmacologically active substance that produces a localized or systemic effect in humans or animals and that can be delivered by the present invention to produce a beneficial and useful result.

Diluent
A liquid that dilutes, as in an inert solution used to dilute a medicament. An inert liquid carrier of a beneficial agent.

Device
An instrument, apparatus, implement, machine, contrivance, implant, in vitro reagent, or other similar or related article, including any component, part or accessory, which is intended for use in the diagnosis, cure, treatment or prevention of disease. A device does not achieve its intended purpose through chemical action in the body and is not dependent upon being metabolized to achieve its purpose.

Apparatus
An appliance or device for a particular purpose: An integrated group of materials or apparatus used for a particular purpose. The totality of means by which a designated function is performed or a specific task executed, a group of body parts that work together to perform a given function.

Reservoir
A receptacle or chamber for storing a fluid. A part of a machine, apparatus, where liquid is stored.

Liquid Container
A receptacle for holding a liquid. A fluid dispenser that is carried or transported.

Collapsible
To cause to fold, break down, or fall down or inward or as in bent-over or doubled-up so that one part lies on another."

Collapsible Container
A dispensing apparatus in which one or more walls of the container are made of a material which will deform (collapse) when pressure is applied thereto; or a dispensing apparatus having a collapsible or telescoping wall structure.

Aseptic Processing
The term 'aseptic processing' as it is applied in the pharmaceutical industry refers to the assembly of sterilized components and product in a specialized clean environment.

Sterile Product
A sterile product is one that is free from all living organisms, whether in a vegetative or spore state.

Blow-Fill-Seal Process
The concept of aseptic blow-fill-seal (BFS) is that a container is formed, filled, and sealed as a unitary container in a continuous manner without human intervention in a sterile enclosed area inside a machine. The process is multi-stepped, pharmaceutical grade resin is extruded into a tube, which is then formed into a container. A mandrel is inserted into the newly formed container and filled. The container is then sealed, all inside a sterile shrouded chamber. The product is then discharged to a non-sterile area for packaging and distribution.

Integrally Formed
An article of one-piece construction, or several parts that are rigidly secured together and is smoothly continuous in form and that any such components making up the part have been then rendered inseparable.

Septum
A word borrowed from the Latin "saeptum" meaning a dividing wall or enclosure; thus, a thin partition or membrane that divides two spaces.

Slit Septum
A septum that is partially slit to aid in cannula penetration.

Penetrating
Tending to penetrate; having the power of entering or piercing.

Cutting
Capable of or designed for incising, shearing, or severing as to cut off from a main body.

Frangible
An article, item or object that is capable of being ruptured or broken, but does not necessarily imply any inherent materials weakness. A material object, under load that demonstrates a mechanical strain rate deformation behavior, leading to disintegration.

Luer-Like Connector
A connector used to connect medical apparatus. Classically, the Luer consists of a tapered barrel and a conical male part that fits into it with or without a seal.

Surface Treatment
The processes of surface treatments, more formally surface engineering, to tailor the surfaces of engineering materials to change, alter or modify the physical surface characteristics and improve the function of the materials properties for its intended purpose.

Spring
A mechanical element that can be deformed by a mechanical force such that the deformation is directly proportional to the force or torque applied to it. An elastic machine component able to deflect under load in a prescribed manner and to recover its initial shape when unloaded. The combination of force and displacement in a deflected spring is energy which may be stored when moving loads are being arrested.

Constant Force Spring

Constant force springs are a special variety of extension spring. They are tightly coiled wound bands of pre-hardened spring steel or stainless steel strip with built-in curvature so that each turn of the strip wraps tightly on its inner neighbor. When the strip is extended (deflected) the inherent stress resists the loading force; the same as a common extension spring, but at a nearly constant (zero) rate. The constant-force spring is well suited to long extensions with no load build-up. In use, the spring is usually mounted with the ID tightly wrapped on a drum and the free end attached to the loading force. Considerable flexibility is possible with constant-force springs because the load capacity can be multiplied by using two or more strips in tandem, or back-to-back. Constant force springs are available in a wide variety of sizes.

Figure 1:
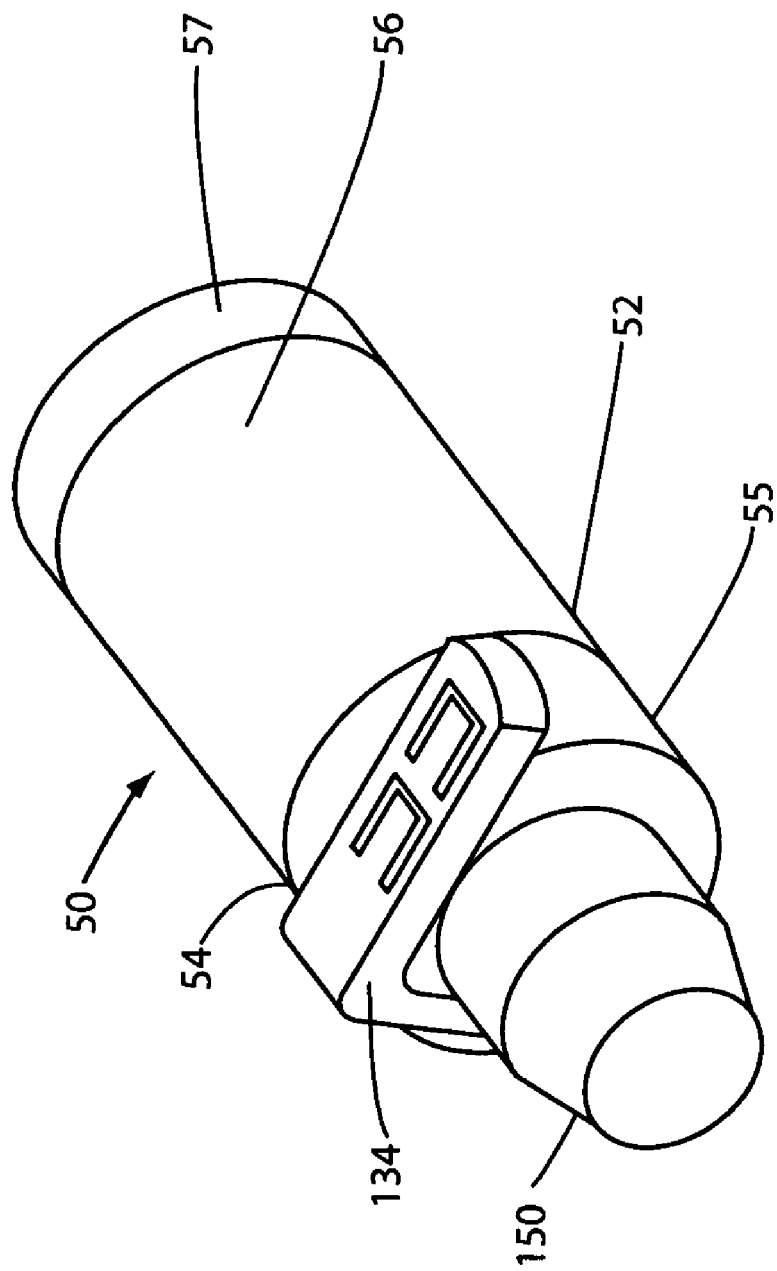
FIG. 1 is a generally perspective, top view of one form of the fluid dispensing apparatus of the present invention for dispensing medicaments to a patient.
Figure 2:
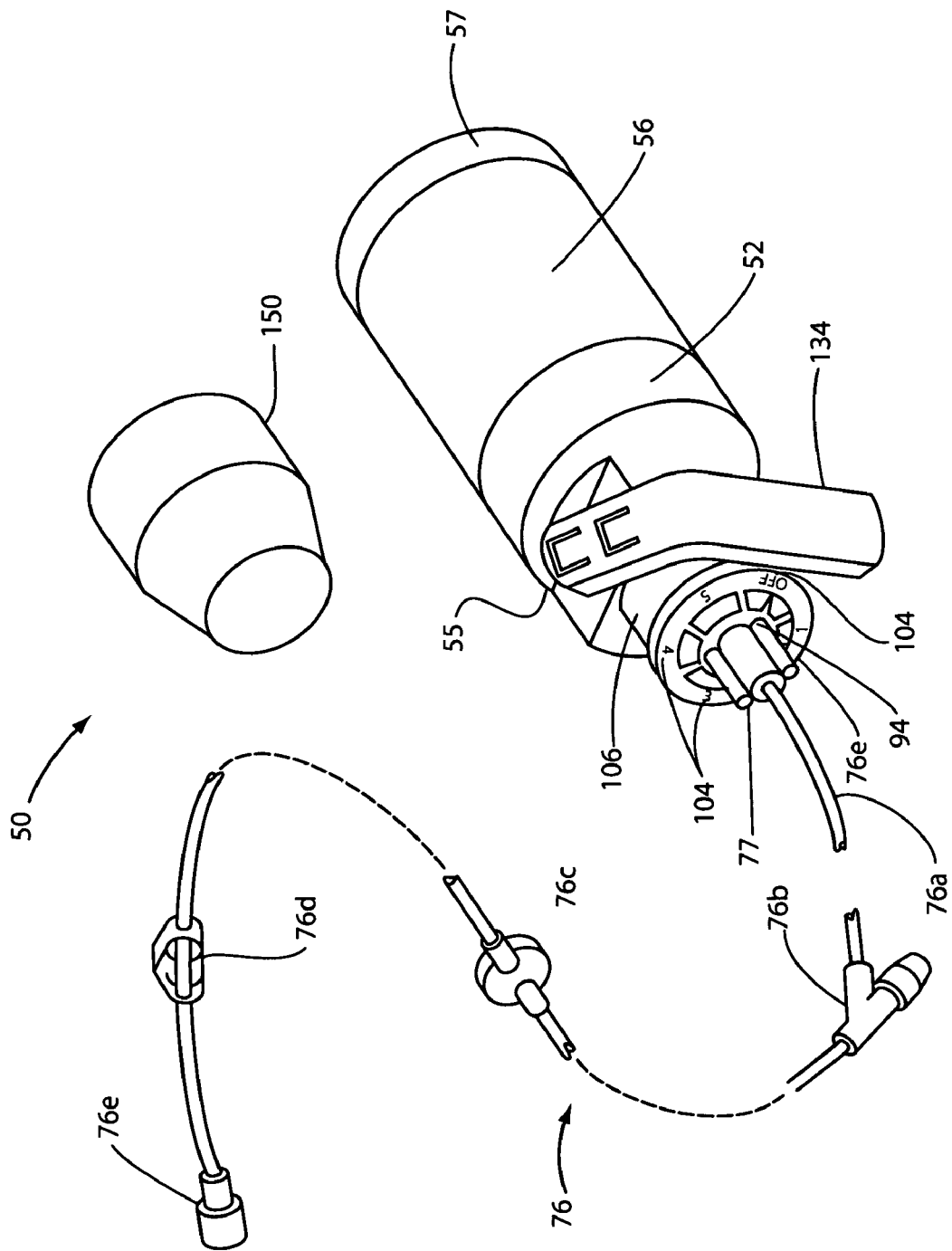
FIG. 2 is a generally perspective, exploded view of the fluid dispensing apparatus shown in FIG. 1 as it appears with a top cover of the apparatus removed.
Figure 5:
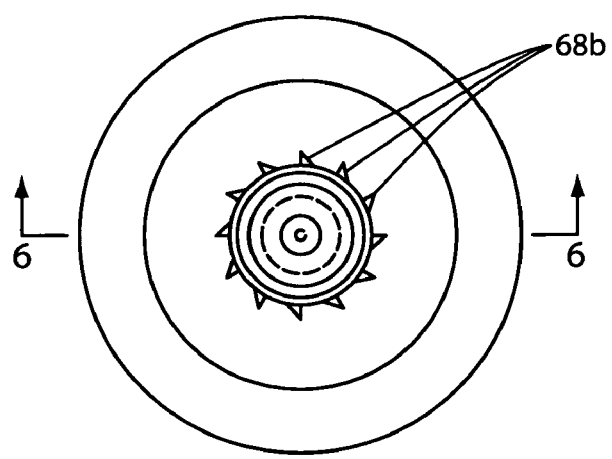
FIG. 5 is a top plan view of the fluid reservoir assembly of the invention.

Referring to the drawings and particularly to FIGS. 1 through 3, one form of the fluid dispensing apparatus of the present invention for dispensing medicaments to a patient is there shown and generally designated by the numeral 50. The dispensing apparatus here comprises a supporting structure 52, which includes a housing 54 having an upper portion 55 and a generally cylindrically shaped skirt portion 56. Supporting structure 52 can be constructed from metal, plastic or any suitable material. Connected to portion 56 is a base segment 57, the details of construction of which will presently be described.

Disposed within skirt portion 56 is a carriage assembly 58, which is movable between a first position shown in FIGS. 3 and 4A and a second position shown in FIG. 4B. As best seen by referring to FIGS. 4A and 4B, carriage assembly 58 comprises a carriage 60 having a carriage flange 60a to which the novel stored energy means of the present invention is operably interconnected. Carriage assembly 58 is releasably locked in its first position by a novel locking means the character of which will be described in the paragraphs, which follow.

Figure 6:
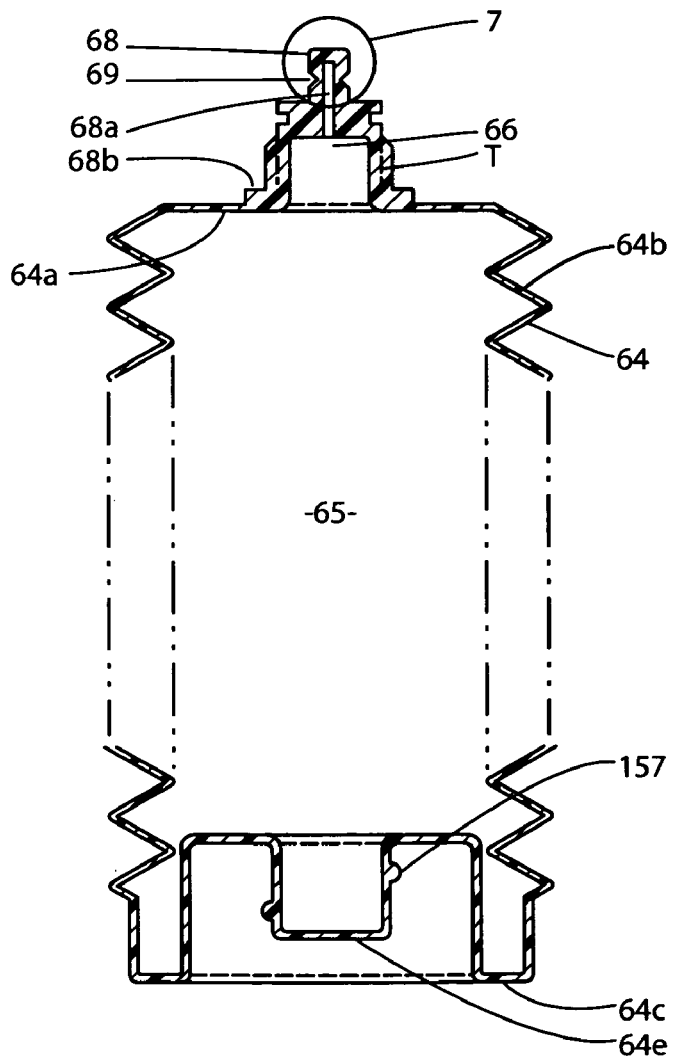
FIG. 6 is a cross-sectional view taken along lines 6-6 of FIG. 5.
Figure 7:
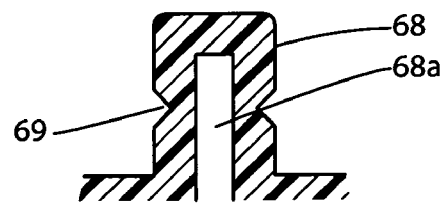
FIG. 7 is an enlarged, cross-sectional view of the area designated in FIG. 6 by the numeral "7".

Carried by carriage assembly 58 is a reservoir defining assembly 64 that defines a fluid reservoir 65. As illustrated in FIGS. 3 and 6, reservoir defining assembly 64 includes a top wall 64a, an accordion-like side wall 64b that is connected to top wall 64a and a bottom wall 64c that is connected to side wall 64b. As illustrated in FIG. 3, bottom wall 64c includes a cup-shaped portion 64e. Reservoir 65 has a combination inlet/outlet 66 that is formed in a reservoir nipple 68 showing a scoreline 69 that also comprises a part of the reservoir assembly 64.

In the preferred form of the invention shown in FIG. 6, nipple 68 is sealably interconnected with top wall 64a in accordance with an aseptic blow-fill-seal technique of a character well understood by those skilled in the art. This blow-fill-seal technique comprises the continuous extrusion through an extruder head of a length of a parison in the form of a hollow tube between and through two co-acting first or main mold halves. The method includes the step of cutting off the parison below the extruder head and above the main mold halves to create an opening which allows a blowing and filling nozzle assembly to be moved downwardly into the opening in the parison for molding and thereafter filling a molded container.

When the container portion of the container assembly is filled with the desired amount of liquid, the blowing and filling nozzle assembly is retracted from the opening in the parison. A separate pair of co-acting second or upper sealing mold halves are then moved together around the exposed length of parison to form and seal the container upper portion. The finished container assembly, completely formed, filled, and sealed as a unitary structure is then conveyed out of the molding apparatus. Further information concerning aseptic blow-fill and blow-fill-seal techniques is available from Weiler Engineering of Elgin, Ill. and from Rommelag of Waiblingen, Germany.

Figure 8:
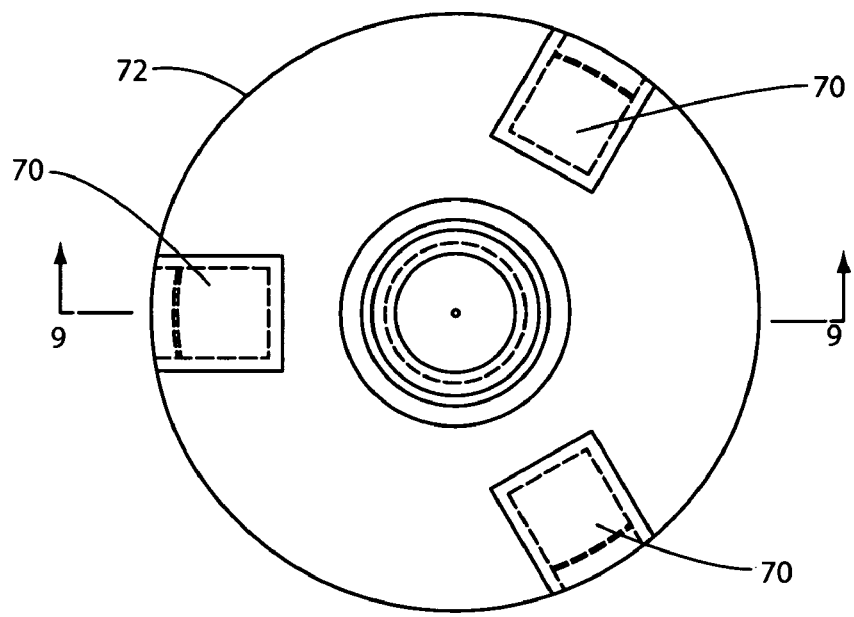
FIG. 8 is a cross-sectional view taken along lines 8-8 of FIG. 3.
Figure 9:
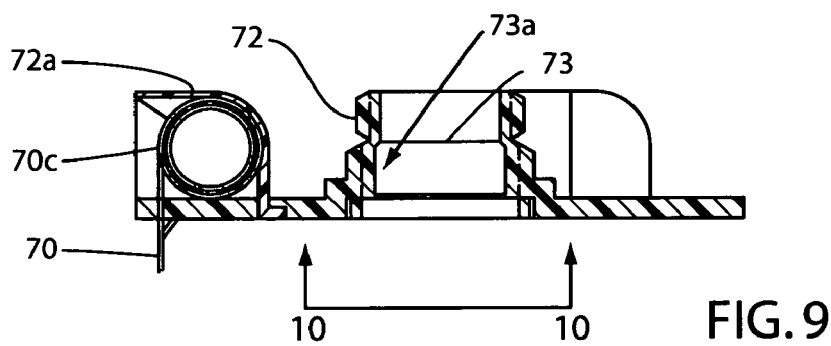
FIG. 9 is a cross-sectional view taken along lines 9-9 of FIG. 8.
Figure 10:
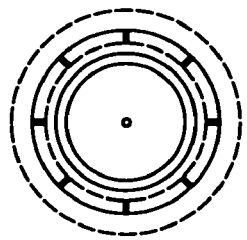
FIG. 10 is a view taken along lines 10-10 of FIG. 9.
Figure 11:
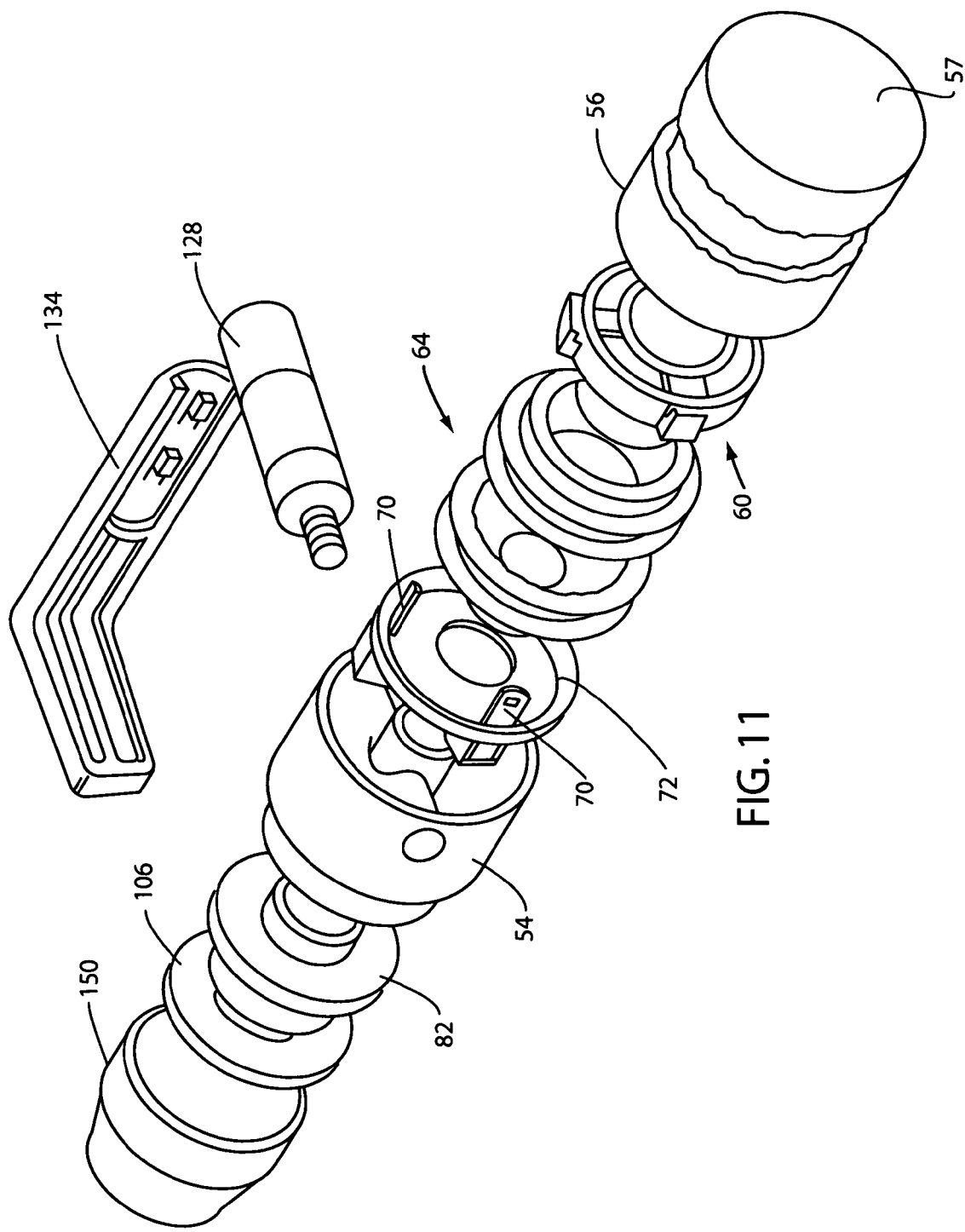
FIG. 11 is a generally perspective, exploded view of the fluid delivery apparatus illustrated in FIG. 1.

To controllably move the carriage assembly from its first position to its second position and to thereby controllably expel the fluid from the fluid reservoir 65, novel stored energy means are provided. These novel stored energy means, which are operably associated with carriage assembly 58, are here provided in the form of three circumferentially spaced-apart, constant force springs 70 (FIGS. 3 and 8). It is to be understood that an alternate number of springs can be used as may be desired. As illustrated in FIGS. 3, 8 and 9, constant force springs 70 are housed within spring retainers 72a which form a part of a spring housing 72 which includes a cavity 73 having internal threads 73a. Housing 72, in turn, forms a part of the supporting structure 52 of the apparatus. The details of construction and operation of these important constant force springs will presently be described.

As will be discussed more fully in the paragraphs which follow during the fluid dispensing step, as the carriage assembly 58 is moved by the constant force springs 70 toward its deployed position, the accordion-like sidewall 64b of the reservoir assembly 64 will be urged to move into the collapsed configuration shown in FIG. 4B and in so doing will cause the fluid contained within the container to be controllably and substantially expelled therefrom.

To further control the flow of fluid from reservoir 65 toward the administration set 76 of the invention and then on to the patient, novel fluid flow control means are provided. The fluid flow control means, which is carried by the supporting structure 52, here comprises two cooperating components, namely a rate control means for controlling the rate of fluid flow from the collapsible reservoir toward the administration set and an operating means for controlling fluid flow between the collapsible reservoir and the rate control means.

Figure 13:
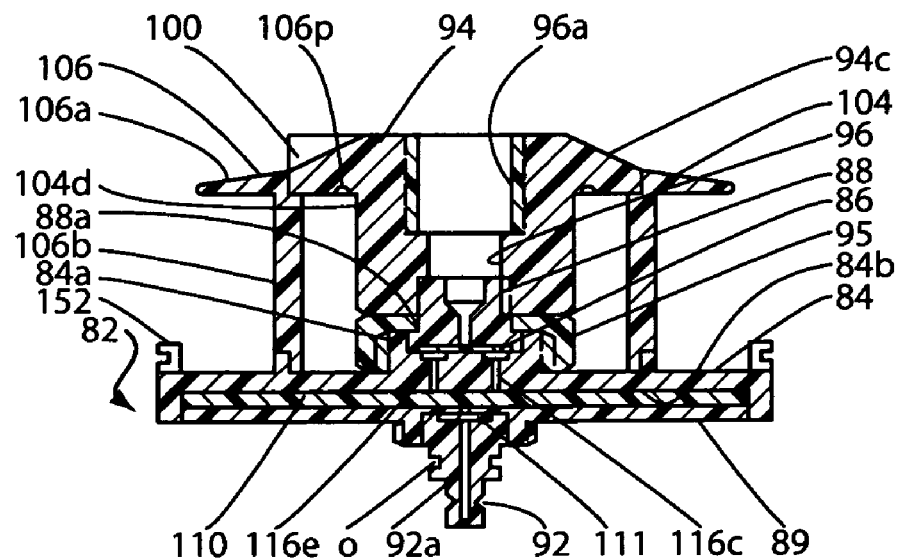
FIG. 13 is a cross-sectional view of the rate control assembly depicted in FIG. 12 as it appears in an assembled configuration.
Figure 15:
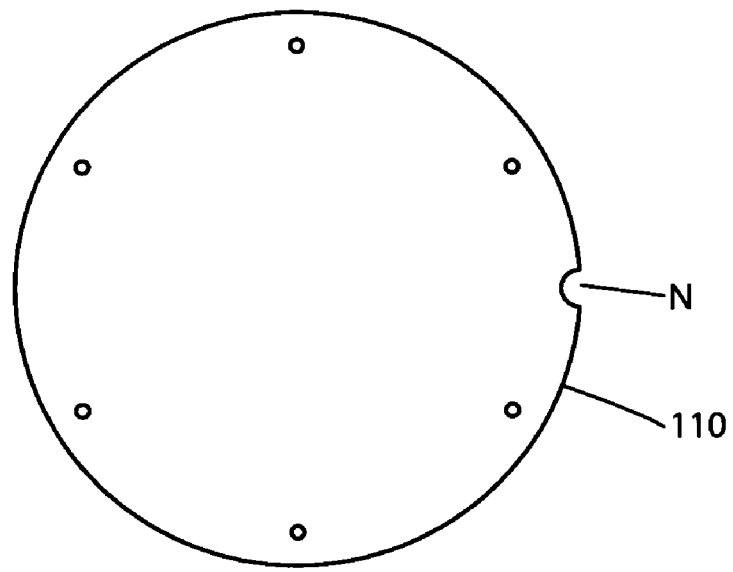
FIG. 15 is a view taken along lines 15-15 of FIG. 14.
Figure 14:
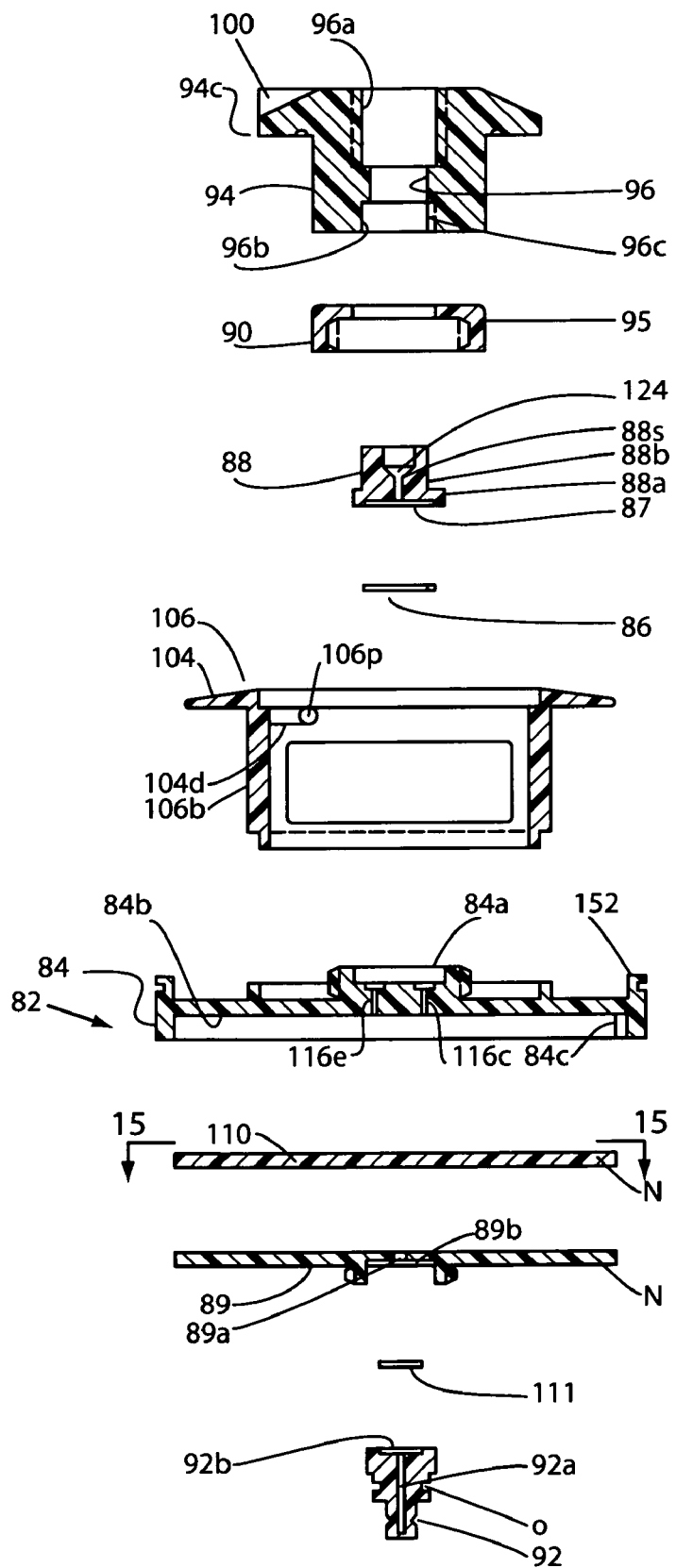
FIG. 14 is an exploded, cross-sectional view of the rate control assembly illustrated in FIG. 13.
Figure 16:
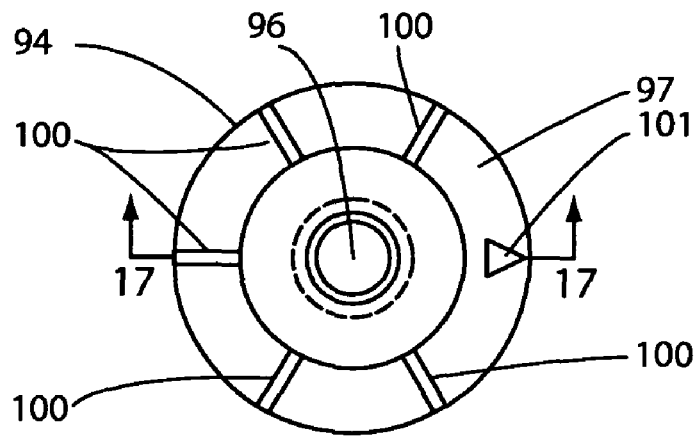
FIG. 16 is a top plan view of the selector knob of the present invention for rotating the selector member in a manner to select the rate of fluid flow to the patient.
Figure 23:
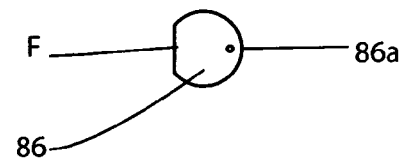
FIG. 23 is a bottom plan view of the selector element.
Figure 20:
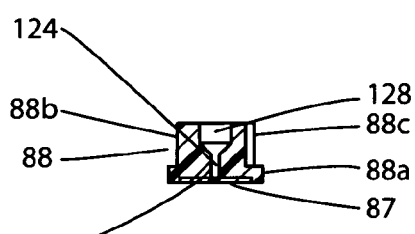
FIG. 20 is a cross-sectional view taken along lines 20-20 of FIG. 19.
Figure 24:
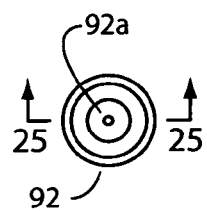
FIG. 24 is a top plan view of the nipple portion of one of the rate control covers of the rate control assembly.

Considering first the rate control means of the invention, this important means comprises a rate control housing 82, which includes a first cover member 84, that engages a selector element 86 which is received within a cavity 87 provided in selector member 88 and located therewithin by a flat "F" (FIG. 23). Selector member 88, which has an enlarged diameter portion 88a (See FIG. 14), forms a part of the selector means of the invention for selecting the desired rate of fluid flow from the fluid reservoir toward the administration set. Cover member 84 also has a rate control plate cavity 84b. As best seen in FIGS. 13 and 14, rate control housing 82 includes a second cover member 89 having an outwardly extending attached nipple 92, the purpose of which will presently be described.

Figure 12:
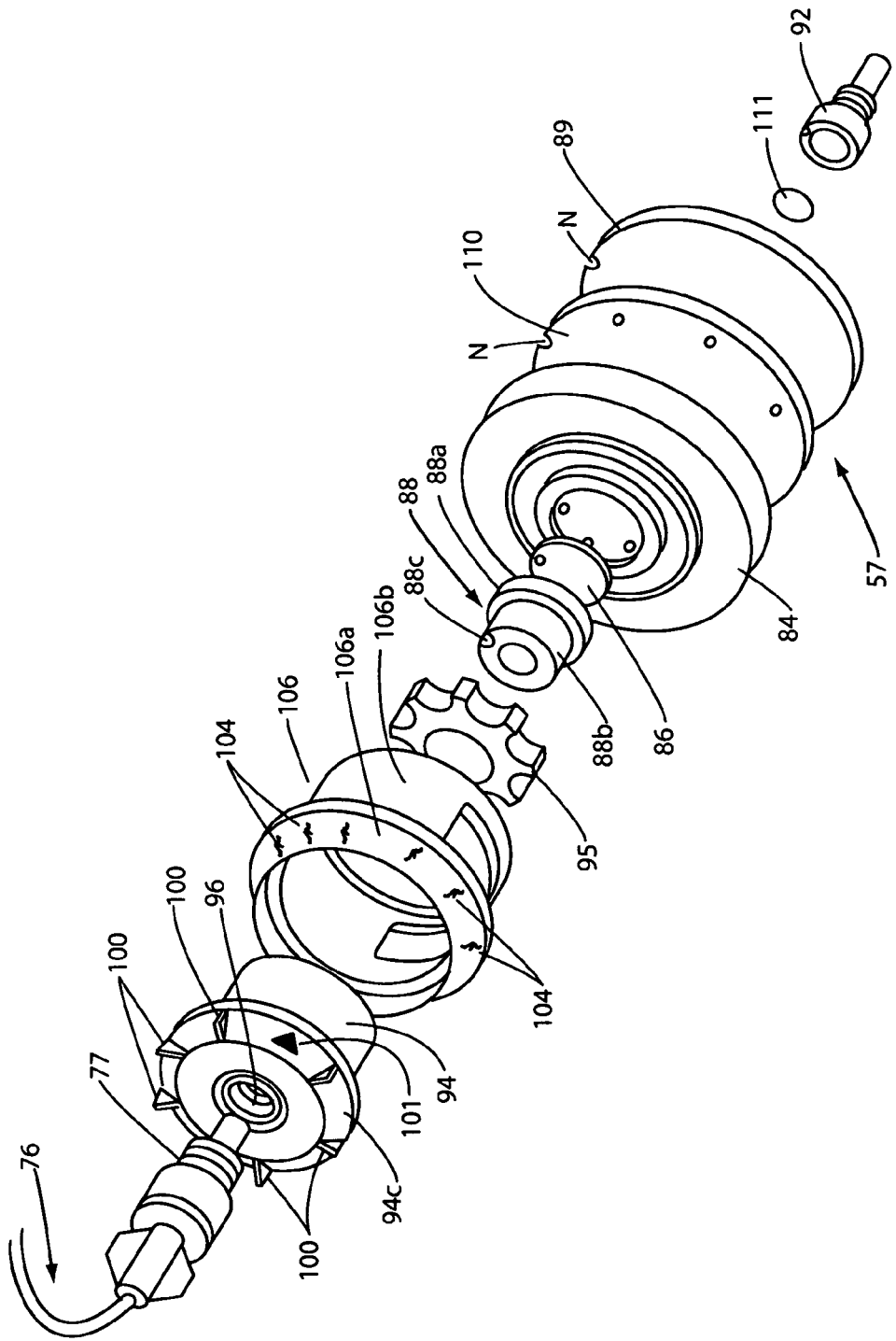
FIG. 12 is a generally perspective, exploded view of the multiple flow rate control assembly of the apparatus of the invention and a portion of the administration set.

Interconnected with rate control housing 82 is a selector knob 94, that includes a central bore 96, the enlarged, threaded diameter portion 96a of which sealably receives the connector hub 77 of the administration set 76 (FIG. 12). The enlarged diameter portion 96b of bore 96, which includes a groove 96c, receives the reduced diameter portion 88b of selector member 88 (FIGS. 13 and 14). A threaded cap 95 retains selector member 88 in position. As shown in FIG. 14, selector member 88 includes an orientation spine 88s that is received in groove 96c. Selector knob 94 also includes an outwardly extending flange 94c which carries circumferentially spaced finger-gripping elements 100 which assist in rotating the selector knob (FIG. 12). Flange 94c also carries an indicator arrow 101, which, upon rotation of the selector member, aligns with flow rate indicia 104 imprinted on the rim portion 106a of a selector member support 106 that supports selector knob 94 (FIGS. 2, 12 and 13). Selector member support 106 also includes a skirt portion 106b that is interconnected with rate control housing 82 in the manner shown in FIGS. 3 and 13. It is to be noted that the movable components of the dispensing apparatus typically carry conventional 0-rings to provide appropriate sealing of the components within the apparatus with their mating parts. Throughout the drawings these 0-rings are identified as "O".

Figure 26:
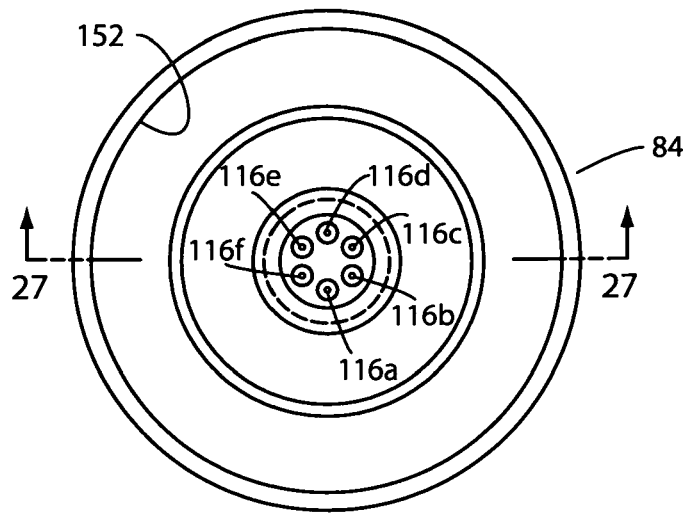
FIG. 26 is a top plan view of the other of the rate control covers.
Figure 27:
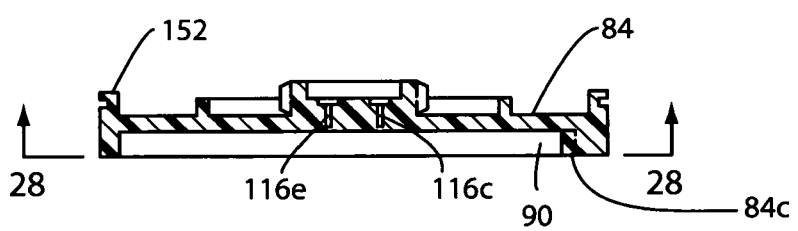
FIG. 27 is a cross-sectional view taken along lines 27-27 of FIG. 26.
Figure 28:
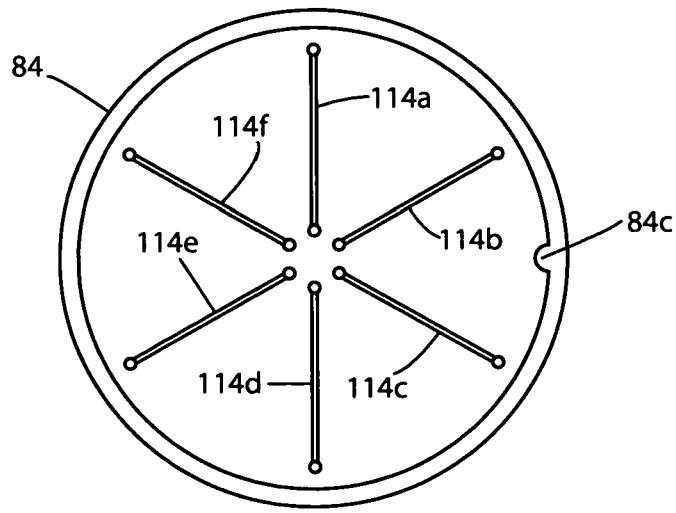
FIG. 28 is a view taken along lines 28-28 of FIG. 27.

As illustrated in FIGS. 4A and 4B, first cover member 84 cooperates with second cover 89 to sealably enclose the rate control plate 110 of the invention (FIGS. 13 and 14) that is disposed between covers 84 and 89 and is oriented therebetween by a spline 84c on cover 84 and notches "N" formed on cover 89 and plate 110. Rate control plate 110 is provided with a plurality of fluid flow channels of different lengths, widths, depths and geometry (FIG. 32) that are in fluid communication with outlet 66 of collapsible reservoir 65 via the operating means of the invention, central passageway 92a of nipple 92, and central passageway 68a of nipple 68. After operating the operating means of the invention in a manner presently to be described to permit fluid to flow into the passageway of the nipples 68 and 92 via the operating means, fluid will flow through passageway 89a, through a conventional particulate filter 111, into a well 89b and into inlet 110a of the rate control plate. From inlet 110a, the fluid will flow into the various circuitous fluid channels 112a, 112b, 112c, 112d, 112e and 112f formed in the rate control plate, each of which is of a different length, width, depth and geometry (see FIGS. 12 and 32). As each of the channels fills with the medicinal fluid to be dispensed to the patient, the fluid will flow into outlet passageways 114a, 114b, 114c, 114d, 114e and 114f respectively formed in rate control cover 84 (FIG. 28). From these outlet passageways, the fluid will flow into and fill circumferentially spaced-apart fluid passageways 116a, 116b, 116c, 116d, 116e and 116f formed in cover member 84 (see FIGS. 26 and 27).

Figure 21:
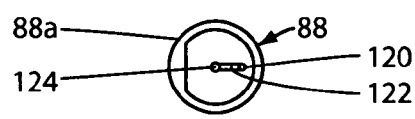
FIG. 21 is a bottom plan view of the selector member shown in FIG. 20.
Figure 25:
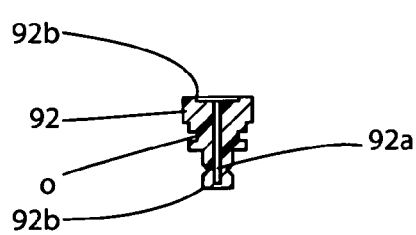
FIG. 25 is a cross-sectional view taken along lines 25-25 of FIG. 24.
Figure 22:
FIG. 22 is front view of the selector element of the rate control means of the invention.

As best seen by referring to FIG. 21, selector member 88, which controllably rotates with knob 94, is provided with an inlet 120, a radially extending inlet passageway 122 and an outlet 124 that is in communication with a central passageway 126 via an orifice 86a of the selector element 86 (FIG. 23). When the connector hub 77 of the administration set 76 is in position within the cavity 96a formed in selector knob 94 in the manner shown in FIG. 4B, the fluid will flow through the selector film 86 and directly into the inlet 77a of the hub 77 of the administration set 76 (FIGS. 3, 20, 21, 22, and 23).

With the construction just described, by rotating the selector knob 94, (See FIG. 4B) which, in turn, rotates selector member 88, inlet 120 of the selector member can be selectively brought into index with one of the axially extending passageways formed in selector member 88, thereby providing fluid communication with a selected one of the circuitous flow passageways formed in rate control plate 110. Since outlet passageway 124 is in fluid communication with the administration set 76 in the manner previously described, the rate of fluid flow toward the patient can be precisely controlled by selecting a rate control passageway of appropriate length that is formed in rate control plate 110.

Figure 36:
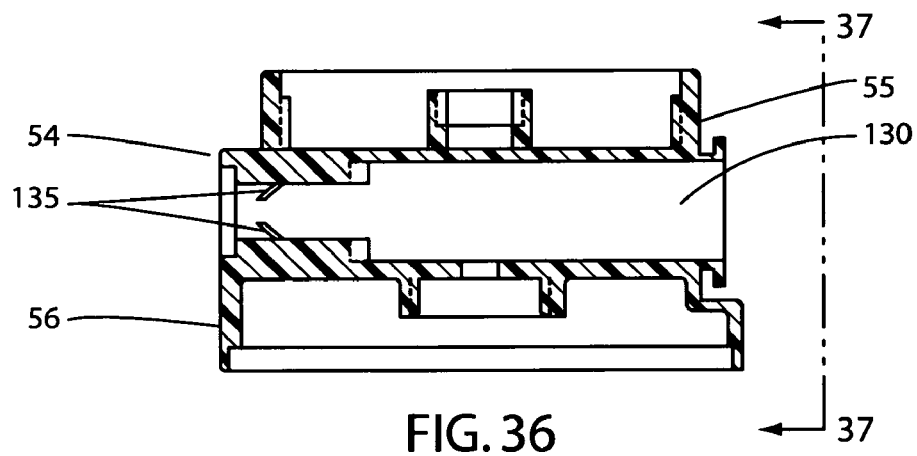
FIG. 36 is a cross-sectional view taken along lines 36-36 of FIG. 35.
Figure 37:
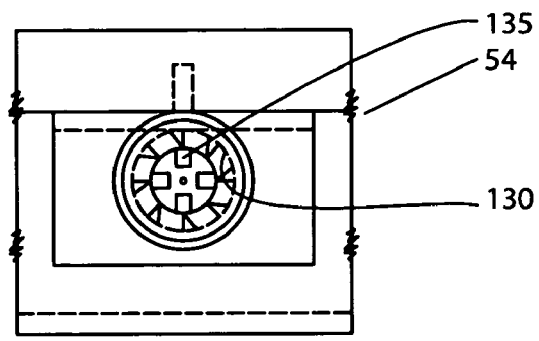
FIG. 37 is a view taken along lines 37-37 of FIG. 36.
Figure 46:
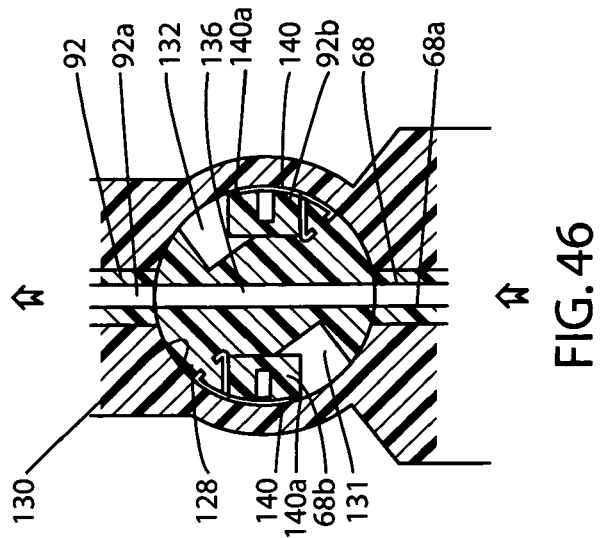
FIG. 46 is a cross-sectional view similar to FIG. 45 but showing the appearance of the components after further rotation of the control shaft from the second position to a third, final position.
Figure 44:
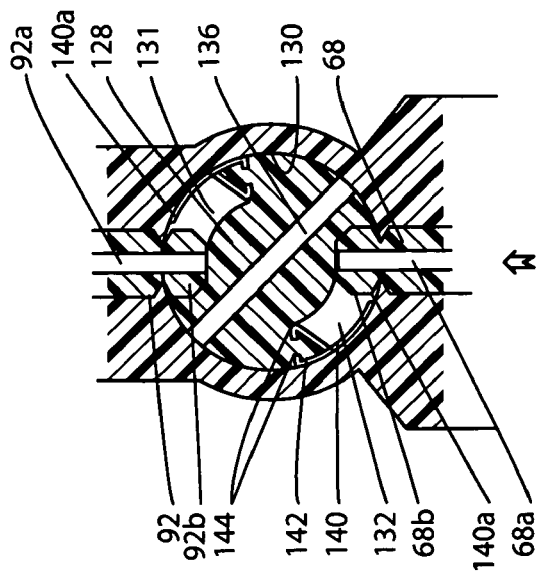
FIG. 44 is an enlarged, cross-sectional view of a portion of the support structure and of the control shaft of the apparatus illustrating the appearance of the components in their starting position.

Considering now the previously identified operating means of the invention, this important means, which controls fluid flow between collapsible reservoir 65 and passageway 92a of nipple 92 of the rate control means, here comprises an operating shaft 128 (FIGS. 4A, 4B and 38) that is sealably, rotatably mounted within a generally cylindrical-shaped chamber 130 (FIGS. 4A, 4B and 36) formed in housing 54 of supporting structure 52 (FIGS. 3, 4A and 36). Operating shaft 128 can be rotated within chamber 130, which is closed by a closure cap 130a, by an "L"-shaped operating handle 134 (FIG. 2) between the position shown in FIG. 44, blocking fluid flow from collapsible reservoir 65 toward administration set 76 and the position shown in FIG. 46 permitting fluid flow from the reservoir toward the administration set.

Turning particularly to FIGS. 38 through 41, operating shaft 128 can be seen to comprise a body portion 128a and a reduced diameter neck portion 128b. Circumferentially spaced-apart, generally arcuate-shaped cavities 131 and 132, which are formed in body portion 128a, are strategically located to receive the end portions of nipples 68 and 92 when the operating shaft is held in position within chamber 130 by integral retainer clips 135 in the manner shown in FIG. 36. Also formed within operating shaft 128 is a transversely extending fluid passageway 136, which, upon rotation of the operating shaft by handle 134, can be moved into alignment with the fluid passageways 68a and 92a of nipples 68 and 92 respectively (see FIG. 46).

Figure 45:
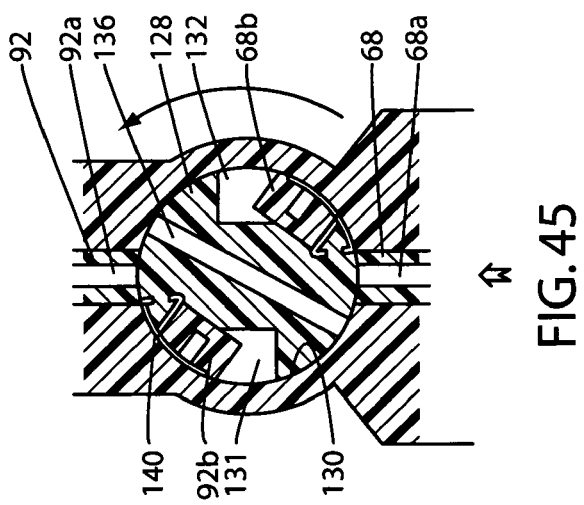
FIG. 45 is a cross-sectional view similar to FIG. 44 but showing the appearance of the components after the initial rotation of the control shaft from a first position to a second position.

Mounted within each of the cavities 131 and 132 is a spring knife 140, which, as indicated in FIGS. 41 and 42, includes a cutting edge 140a formed proximate one extremity and a pair of mounting clips 142 provided proximate the opposite extremity. Tabs 142a of the mounting clips are received within slots 144 formed in body portion 128a so as to secure the spring knives within the arcuate cavities in the manner illustrated in FIG. 44. With this construction, as the operating shaft 128 is rotated by handle 134 from the position shown in FIG. 44 into the position shown in FIG. 45 the spring knives will cleanly sever the sealed tip portions 68b and 92b of nipples 68 and 92 respectively. Continued rotation of operating member 128 will move sealed tip portions 68b and 92b into the cavities for rotation therewith (FIG. 45) and will move transverse passageway 136 into alignment with passageways 68a and 92a in a manner shown in FIG. 46. With the operating member in this position fluid can flow freely from reservoir 65 toward the rate control means of the invention via passageways 68a and 92a of nipples 68 and 92.

Figure 32:
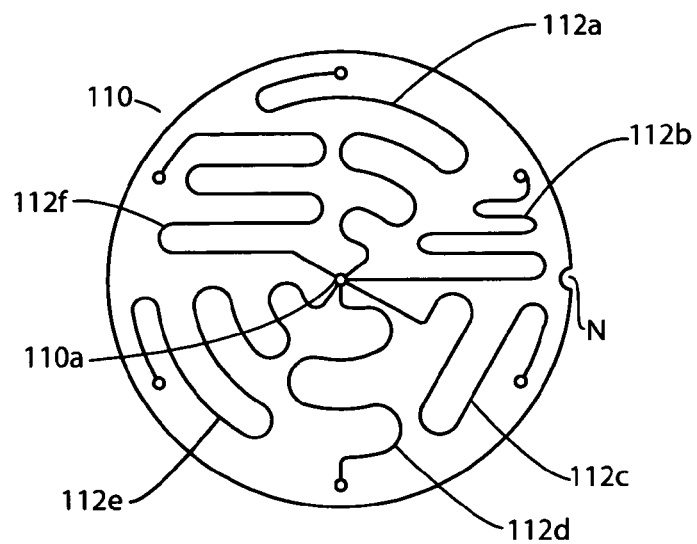
FIG. 32 is a bottom plan view of the rate control plate of the rate control assembly.
Figure 34:
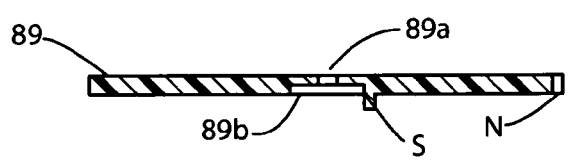
FIG. 34 is a cross-sectional view taken along lines 34-34 of FIG. 33.
Figure 33:
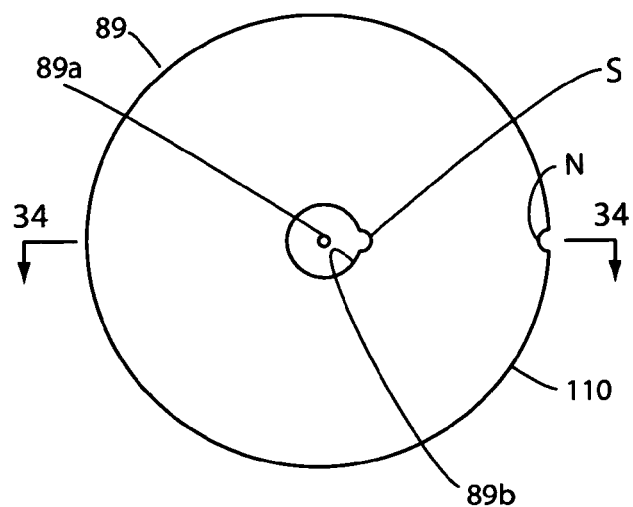
FIG. 33 is a top plan view of the cover member 89 of the rate control assembly.
Figure 35:
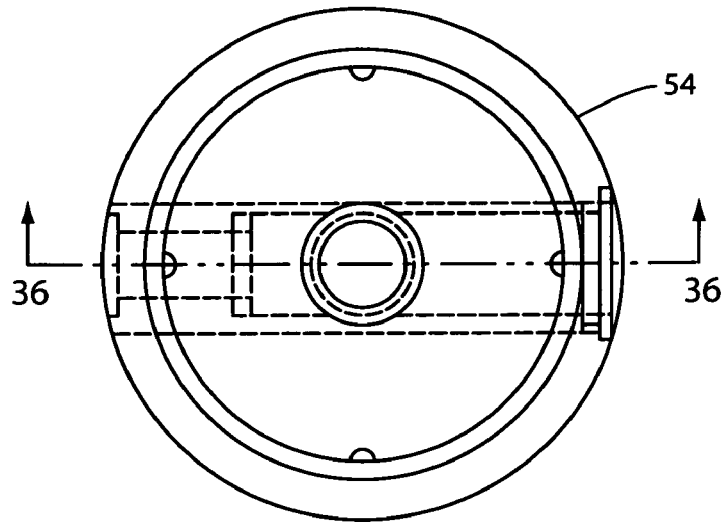
FIG. 35 is a top plan view of a portion of the supporting structure of the apparatus of the invention.

From passageway 68a, fluid will flow through passageway 136, through passageway 92a, through conventional particulate filter 111, through well 89b, through outlet 89a, into inlet 110a of rate control plate 110 of the rate control assembly and then into the various circuitous fluid channels 112a, 112b, 112c, 112d, 112e and 112f formed in the rate control plate (see FIGS. 3, 13 and 32). Rate control plate 110, which can be constructed from various plastics, is oriented relative to members 84 and 89 by the previously identified notches "N" and spines "S" and 84c. Filter 111 is maintained in position within cavity 92b of member 92 which is received in a cavity 89b formed in plate 89. As each of the channels fills with the medicinal fluid to be dispensed to the patient, the fluid will flow next into outlet passageways 114a, 114b, 114c, 114d, 114e and 114f respectively formed in rate control cover 84 (FIG. 28). From these outlet passageways, the fluid flows into and fills circumferentially spaced-apart fluid passageways 116a, 116b, 116c, 116d, 116e and 116f formed in cover member 84 (see FIGS. 26 and 27). By controllably rotating knob 94 which in turn rotates the selector member 88, inlet 120 thereof can be selectively brought into index with one of the fluid passageways formed in cover member 84 via element 86, thereby providing fluid communication with a selected one of the circuitous flow passageways formed in rate control plate 110. Since outlet passageway 124 of the selector member 88 is in fluid communication with the administration set 76 in the manner previously described the fluid can be delivered to the patient at a selected controlled rate of flow.

Figure 17:
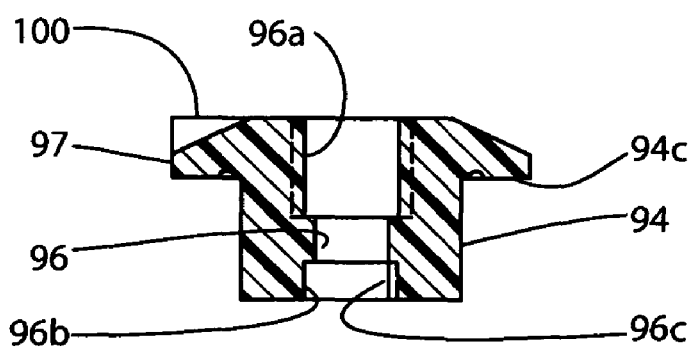
FIG. 17 is a cross-sectional view taken along lines 17-17 of FIG. 16.
Figure 18:
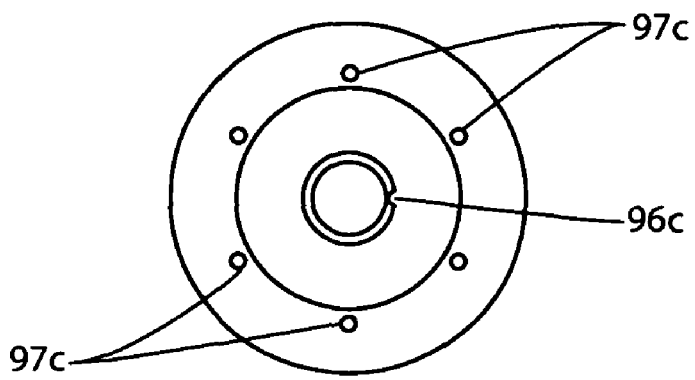
FIG. 18 is a bottom plan view of the selector knob shown in FIG. 17.
Figure 19:
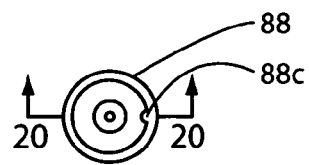
FIG. 19 is a top plan view of the selector member of the apparatus which is rotated by the selector knob.
Figure 31:
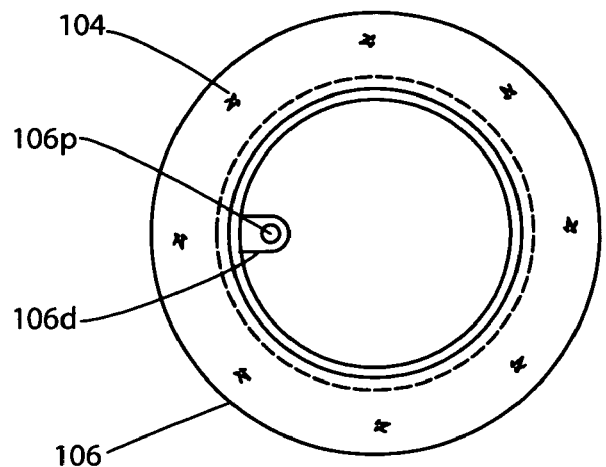
FIG. 31 is a view taken along lines 31-31 of FIG. 29.
Figure 30:
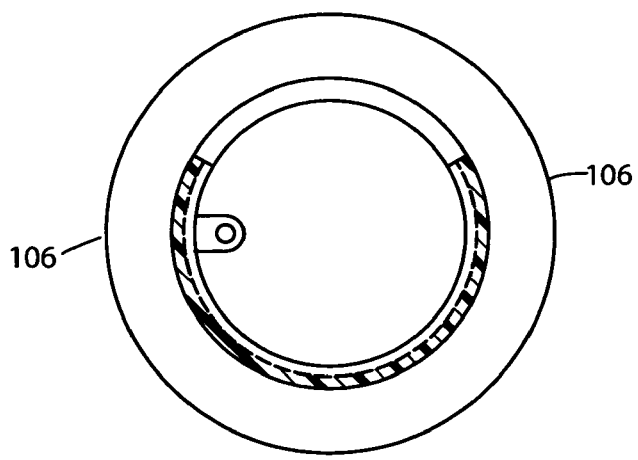
FIG. 30 is a cross-sectional view taken along lines 30-30 of FIG. 29.
Figure 29:
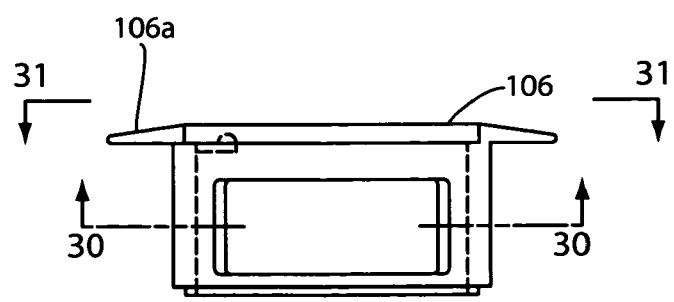
FIG. 29 is a side elevation view of the selector member housing of the apparatus.
Figure 47:
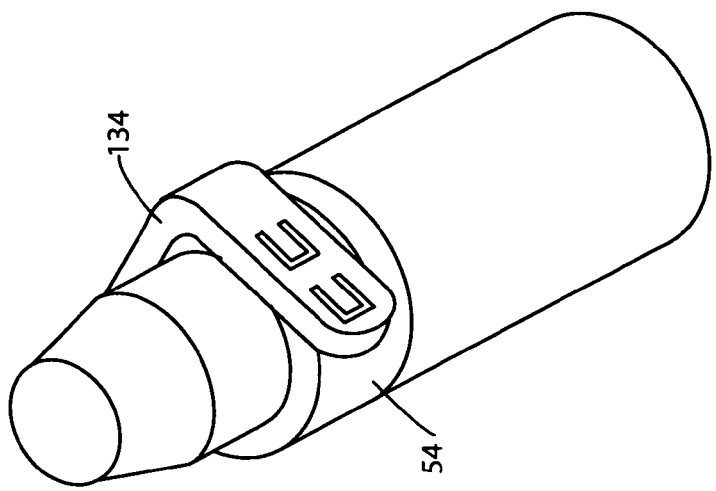
FIG. 47 is a generally perspective, diagrammatic view showing the operating handle of the apparatus in its starting position.
Figure 48:
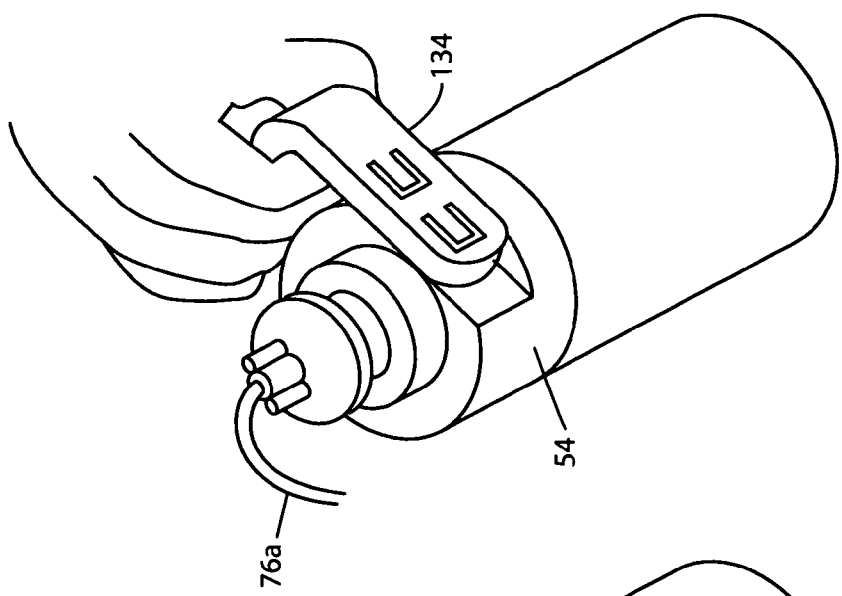
FIG. 48 is a generally perspective, diagrammatic view illustrating the gripping of the apparatus handle by the operator.
Figure 49:
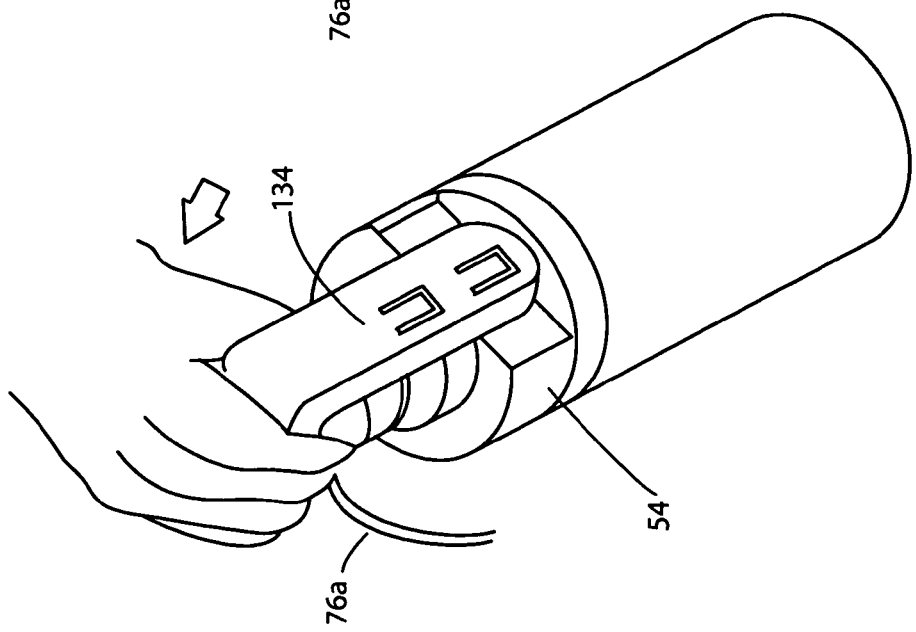
FIG. 49 is a generally perspective, diagrammatic view illustrating the movement of the operating handle by the operator to open the fluid flow path between the reservoir and the rate control means of the invention.

With the apparatus in the configuration shown in FIG. 1 and with the fluid reservoir 65 filled with the medicament to be dispensed to the patient, the dispensing operation can be commenced by removing the top cover 150 which is snapped over a cover connector 152 that protrudes from the rate control cover 84. With the top cover removed, the administration line 76a of the administration set 76 can be unwrapped from the sleeve 106b of the selector knob support 106 about which it has been coiled (see FIG. 3). Removal of the top cover 150 also exposes the selector knob 94 so that the fluid flow rate can be selected by rotating the selector knob to the desired flow rate indicated by the indicia 104 imprinted on the rim of the selector knob support 106 (FIG. 2). In this regard, it is to be noted that selector knob 94 is provided with a plurality of circumferentially spaced cavities 97c (FIG. 17) that are engaged by a protuberance 106p formed on inwardly extending flange 106d of support 106 (FIGS. 13 and 31). With the desired flow rate thusly set, the operating shaft 128 is next rotated through the use of the operating handle 134 from the starting position shown in FIG. 47 to the fully rotated position shown in FIG. 49. In this way, communication is opened between the reservoir outlet 66 and passageway 92a of nipple 92 which, in turn, is in communication with the rate control assembly of the invention.

Figure 51:
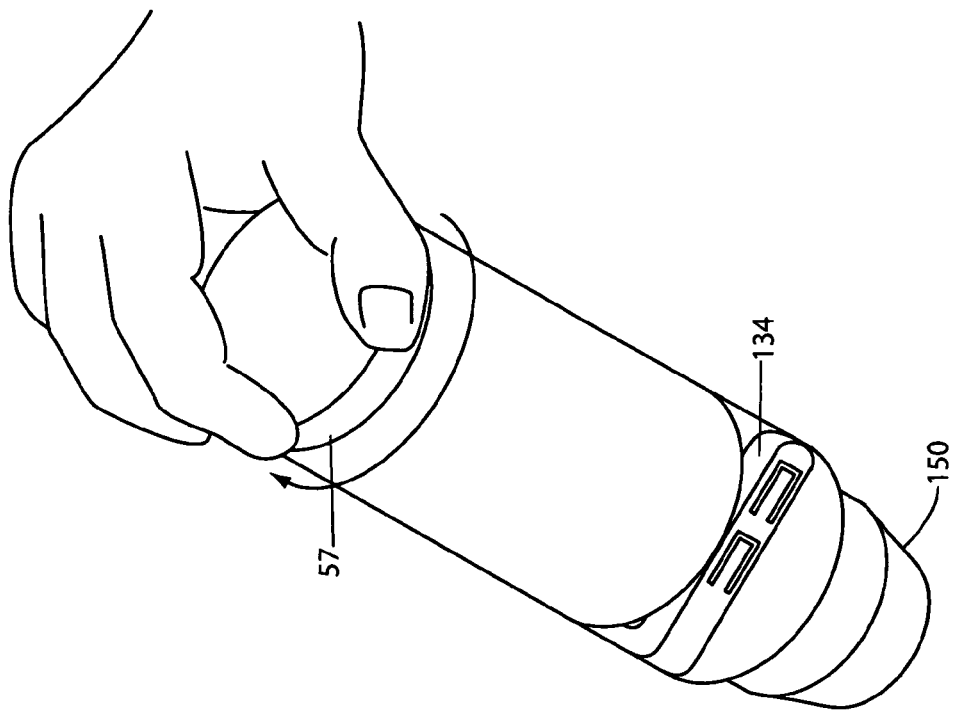
FIG. 51 is a generally perspective, diagrammatic view illustrating the operation of the locking means of the apparatus to release the carriage so as to arm the system to permit delivery of fluid to the patient via the administration set of the apparatus.
Figure 50:
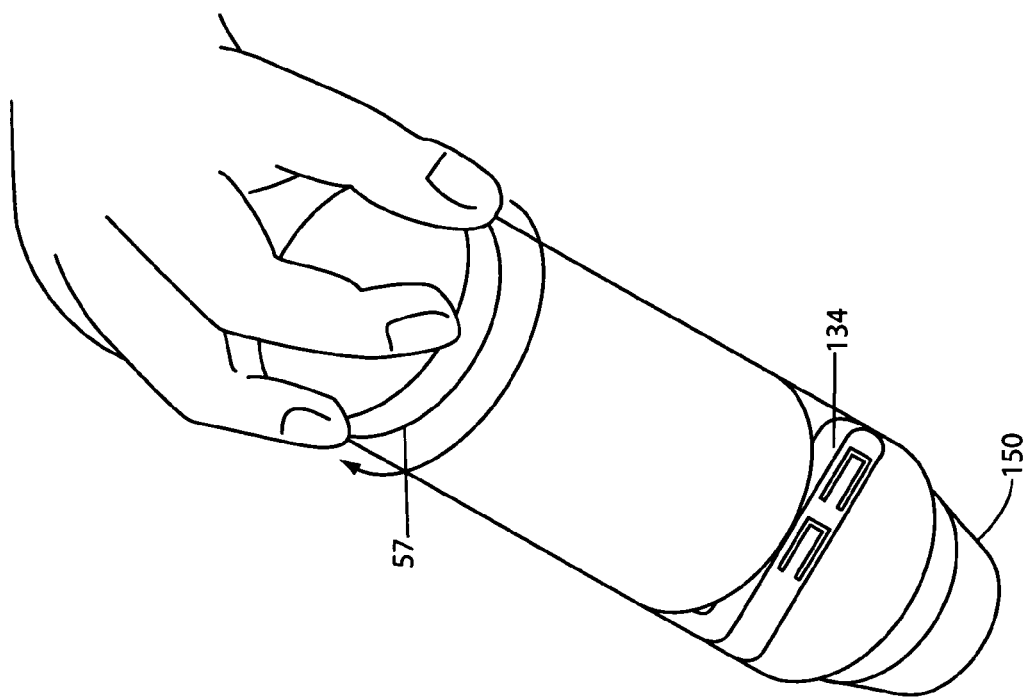
FIG. 50 is a generally perspective, diagrammatic view illustrating the operation of the locking means of the apparatus in a manner to lock the carriage to the base component of the apparatus structural support.

Following the controlled rotation of the operating shaft 128 in the manner shown in FIGS. 44 through 49, the carriage locking means of the invention can now be manipulated in the manner illustrated in FIG. 51 to release the carriage 60 from base segment 57 in order to permit the stored energy means, or constant force springs 70 to move the carriage from the fully deployed or extended starting position shown in FIG. 4A to the retracted position shown in FIG. 4B. In this regard, as best seen in FIGS. 4A, 4B and 51, the carriage locking means here comprises the previously identified base segment 57 which includes a locking sleeve 57a that is provided with a cam groove 155 that is adapted to mate with a male thread 157 formed on the base 57 of container 64 (see FIGS. 4A and 6). With this construction, upon rotating base segment 57 so as to release the carriage in the manner shown in FIGS. 4B and 51, carriage 60 is then free to move in response to the urging of the constant force springs 70 from the position shown in FIG. 4A to the fluid delivery position shown in FIG. 4B. As the carriage moves into the fluid delivery position the fluid contained within reservoir 65 will be caused to controllably flow toward reservoir outlet 66, into fluid passageway 68a of nipple 68, through passageway 136 formed in control member 128 and into passageway 92a of nipple 92. From passageway 92a, fluid will flow through conventional particulate filter 111, into the well 89b, through outlet 89a, and into inlet 110a of rate control plate 110 and then into the various circuitous fluid channels 112a, 112b, 112c, 112d, 112e and 112f formed in the rate control plate (see FIG. 32). As each of the channels fills with the medicinal fluid to be dispensed to the patient, the fluid will flow into and fill circumferentially spaced-apart fluid passageways 114a, 114b, 114c, 114d, 114e and 114f formed in cover member 84 (see FIG. 28). By controllably rotating the selector knob 94, inlet 120 of selector member 88 can be selectively brought into index with one of the fluid passageways 116a, 116b, 116c, 116d, 116e and 116f formed in cover member 84, thereby providing fluid communication with a selected one of the circuitous flow rate control passageways formed in rate control plate 110 and in this way select the desired rate of fluid flow to the administration set and then on to the patient.

In the present form of the invention, administration set 76, which comprises a part of the dispensing means of the invention for delivering medicinal fluids to the patient, includes, in addition to administration line 76a, a conventional "Y"-site injection septum or port 76b, a conventional gas vent and particulate filter 76c and a line clamp 76d. Provided at the distal end of the administration line is a Luer connector 76e of conventional construction (FIG. 2) which enables the apparatus to be interconnected with the patient in a conventional manner.

The stored energy members or constant-force springs 70, which are a special variety of extension spring, are readily commercially available from several sources, including Barnes Group Inc. of Bristol, Conn.; Stock Drive Products/Sterling Instrument of Hyde Park, N.Y. and Walker Corporation of Ontario, Calif. Constant force extension springs are basically high stress, long deflection apparatus that offer great advantages when used in applications, such as the present application, where very low or zero gradient is desired, where space is a factor and where very high reliability, accuracy, and linear force tolerance is required. Constant force springs, such as springs 70, provide markedly superior constant force loading when compared to conventional helical extension or like conventional types of springs. A constant force spring is typically a roll of pre-stressed metal strip that exerts a nearly constant restraining force to resist uncoiling or recoiling. The force is constant over time because the change in the radius of the curvature is constant. Springs 70 can be of a laminate construction, or alternatively spring 70 can comprise a single spring element of the character shown in the drawings.

Figure 53B:
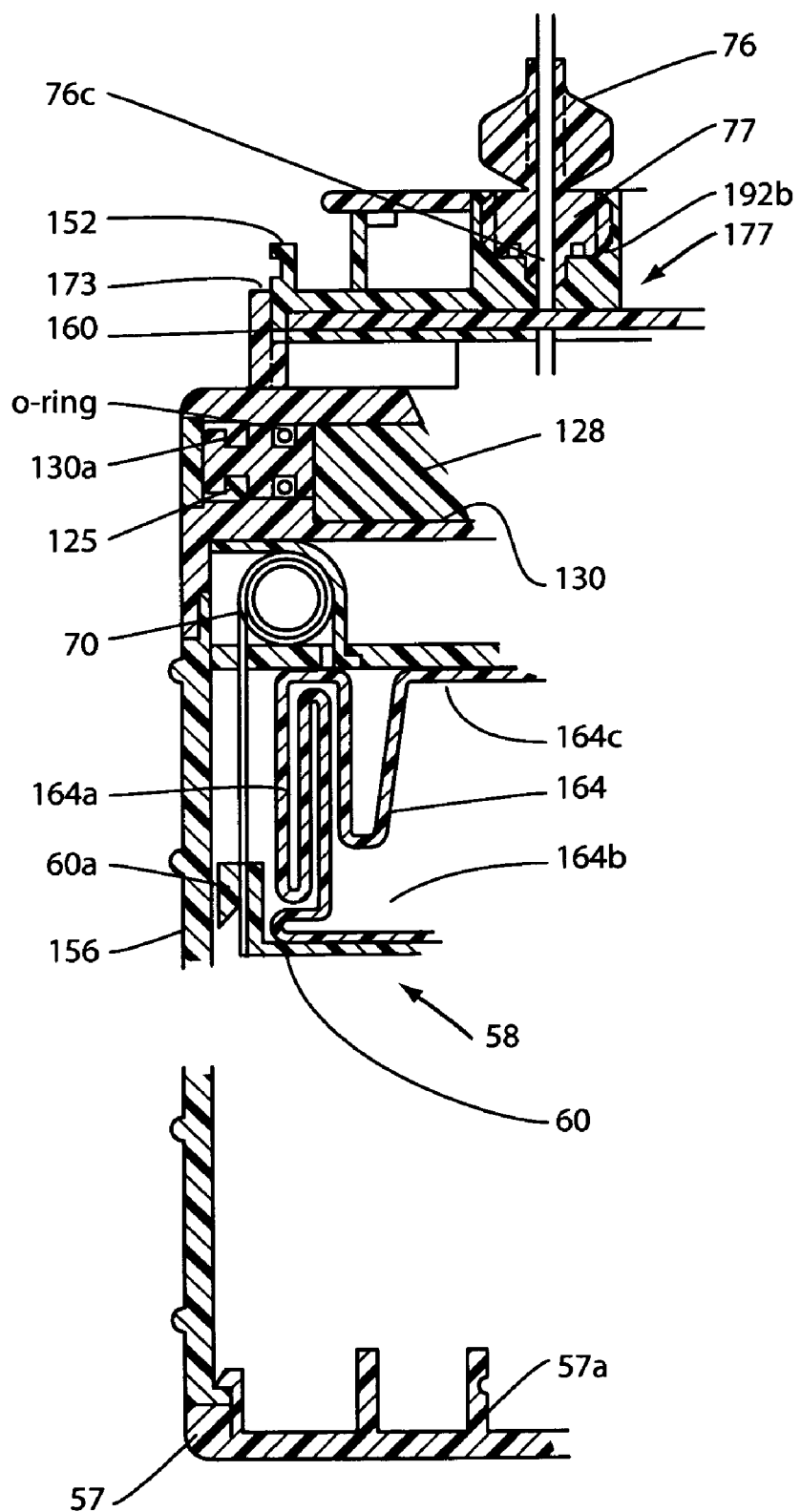
FIG. 53B is a fragmentary, longitudinal, cross-sectional view similar to FIG. 53A, but showing the various components of the apparatus as they appear with administration line installed and following delivery to the patient of the fluid contained within the apparatus reservoir.
Figure 56:
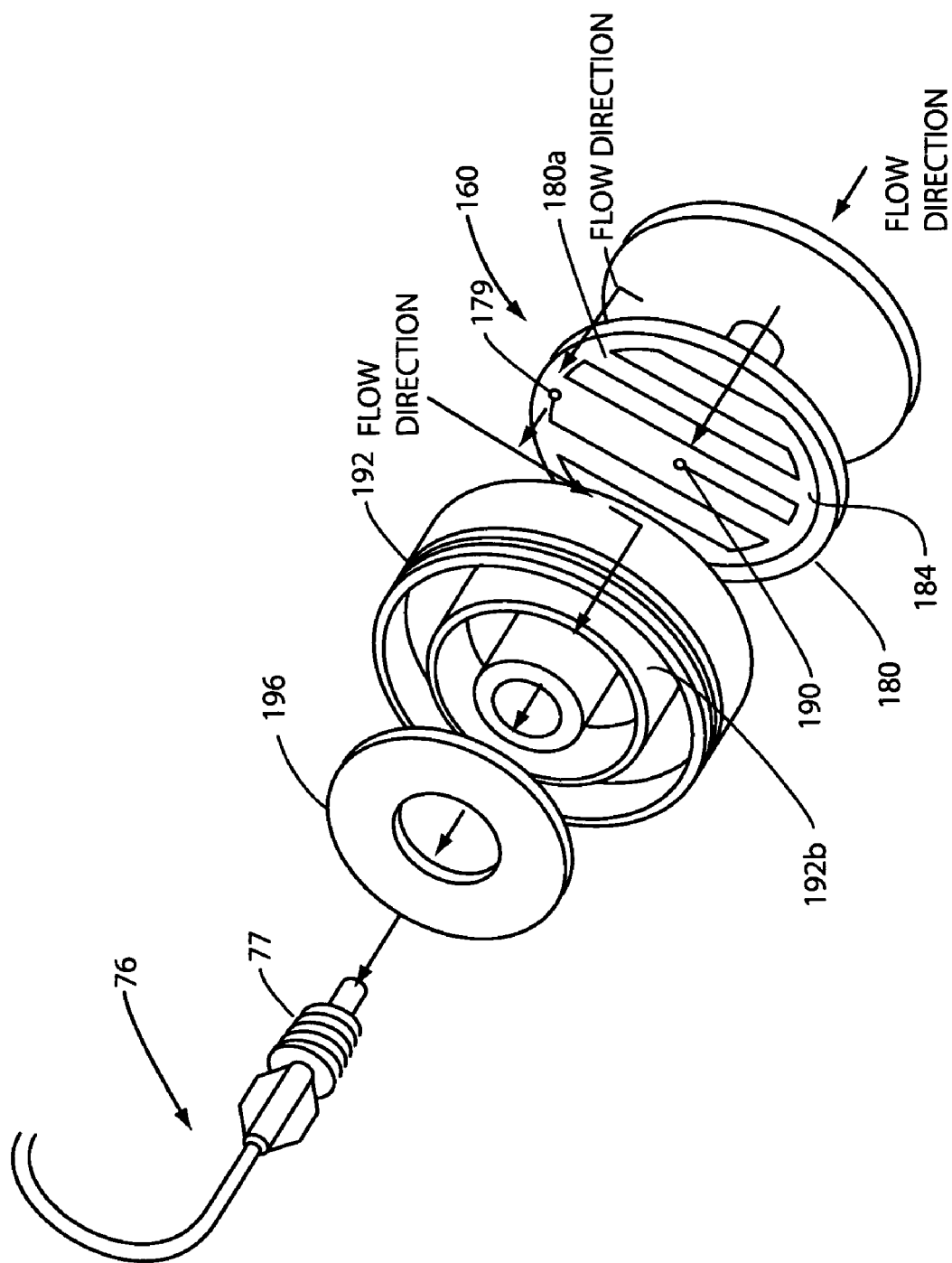
FIG. 56 is a generally perspective, exploded view of a portion of the administration set and of the single or fixed rate control assembly of this latest embodiment of the invention.

Turning now to FIGS. 52, 53A and 53B, an alternate form of the dispensing apparatus of the present invention for dispensing medicaments to a patient is there shown. This alternate form of dispensing apparatus is similar in many respects to that shown in FIGS. 1 through 51 and like numerals are used in FIGS. 52 through 64 to identify like components. As before, the dispensing apparatus here includes a supporting structure which includes an upper portion 154 and a generally cylindrically shaped skirt portion 156 that is interconnected with the upper portion in the manner best seen in FIG. 52 of the drawings.

Disposed within skirt portion 156 is a carriage assembly 60 which is movable between a first position shown in FIGS. 52 and 53A and a second position shown in FIG. 53B. Carriage assembly 60 is of identical construction and operation to that previously described and is releasably locked in its first position by locking means also identical to the locking means previously described herein.

The primary difference between this latest form of dispensing apparatus of the invention and that previously described resides in the provision of a single, rather than multiple, flow rate control assembly 160 and a reservoir defining assembly 162 of a totally different construction. Reservoir defining assembly 162 here comprises a collapsible container assembly 164 which is carried by carriage assembly 60 in the manner illustrated in FIG. 52.

As best seen by referring to FIGS. 52 and 54, collapsible container assembly 162 includes a collapsible container 164 having a collapsible sidewall 164a, an interconnected bottom wall 164b and an interconnected top wall 164c to which a sealed reservoir nipple 166 which is scored about its periphery is sealably interconnected. Collapsible container assembly 164 defines a fluid reservoir 168 having an inlet/outlet that is generally identified by the numeral 170 (FIGS. 52 and 54).

In the preferred form of this alternate embodiment of the invention, nipple 166 is sealably interconnected with member top wall 164*c* in accordance with an aseptic blow-fill-seal technique of the general character previously described to form a unitary structure.

To controllably move the carriage assembly 60 from its first position to its second position, novel stored energy means are provided. This novel stored energy means, which is identical in construction and operation to that previously described, comprises three circumferentially spaced constant force springs 70.

As in the earlier described embodiment of the invention, following operation of the operating means, when the locking means of the invention is manipulated in a manner to unlock the carriage assembly from base portion that is substantially similar to base portion 57, springs 70 will move from their extended position shown in FIGS. 52 and 53A to their retracted position shown in FIG. 53B and in so doing will controllably move the carriage assembly from its fully deployed or extended starting position shown in FIG. 52 to its fully retracted position shown in FIG. 53B. As the carriage assembly moves toward its retracted position, the collapsible sidewall 164*a* of the collapsible container 164 will move into the collapsed configuration shown in FIG. 53B. As the collapsible container collapses, the medicinal fluid or diluent contained within the container will be substantially and controllably expelled therefrom.

To further control the flow of medicinal fluid from reservoir 168 toward the administration set 76 of the invention and then on to the patient, flow control means are provided. As before this novel fluid flow control means, comprises two cooperating components, namely a rate control means for controlling the rate of fluid flow from the collapsible reservoir to the patient and an operating means for controlling fluid flow between the collapsible reservoir and the rate control means. As previously mentioned, the rate control means is different from that previously described. However, the flow control means of this embodiment is identical in construction and operation to that previously described. The important alternate form of rate control means will be more fully described in the succeeding paragraphs.

As in the earlier described embodiment of the invention, the important flow control means, which controls fluid flow between collapsible reservoir 164 and the rate control means, comprises an operating shaft 128 that is rotatably mounted within a generally cylindrically shaped chamber 130 formed in upper portion 154 of the supporting structure. As before, operating shaft 128 can be rotated within chamber 130 by an "L"-shaped operating handle between a first position blocking fluid flow from collapsible reservoir 168 toward administration set 76 and a second position permitting fluid flow from the reservoir toward the administration set.

Figure 57:
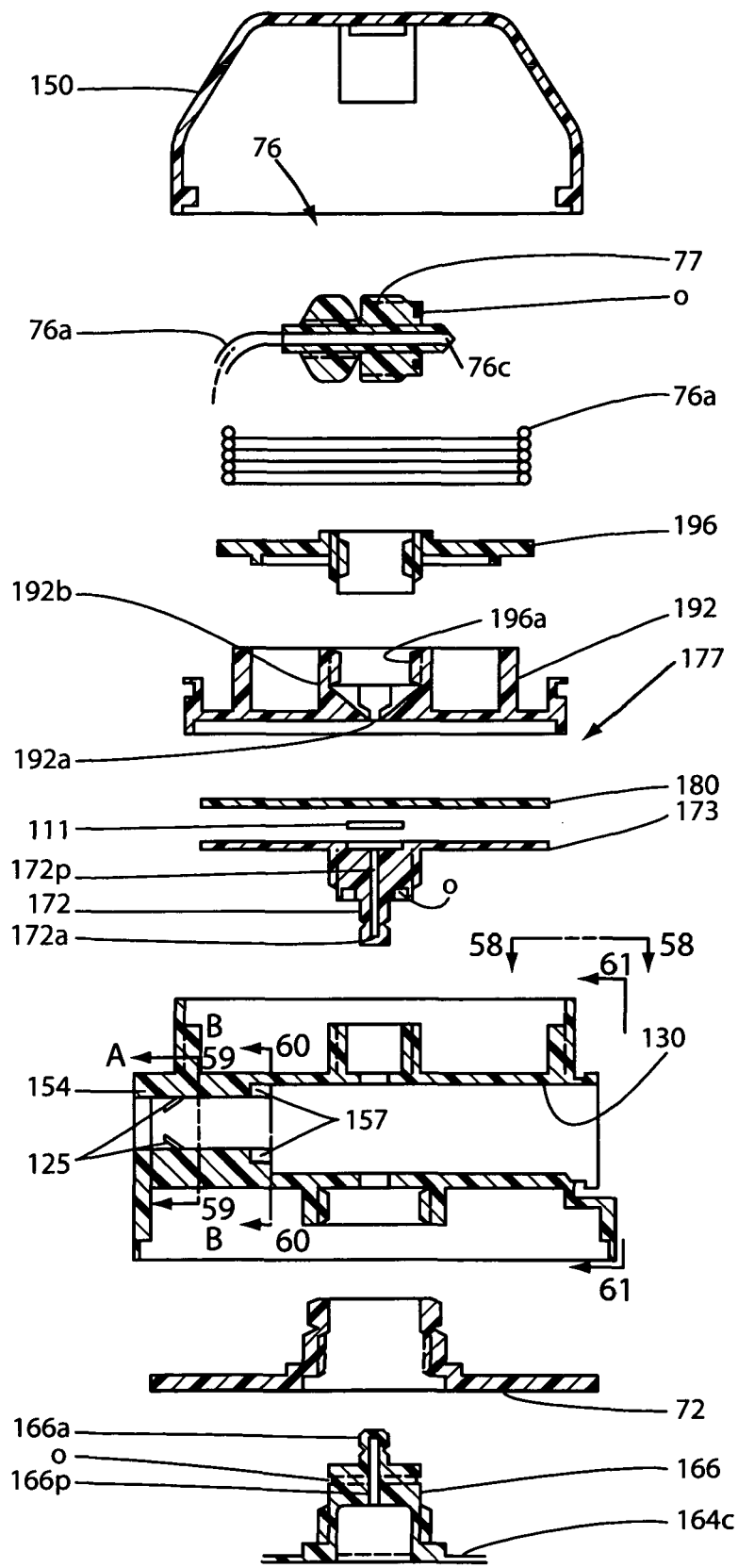
FIG. 57 is an exploded, cross-sectional view of the upper portion of the apparatus illustrated in FIG. 52.
Figure 58:
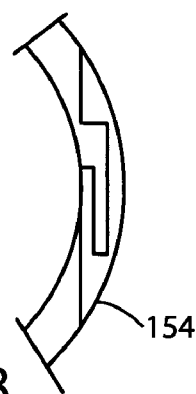
FIG. 58 is a cross-sectional view taken along lines 58-58 of FIG. 57.
Figure 59:
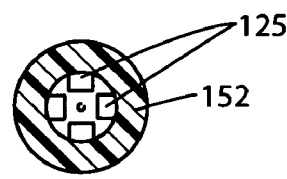
FIG. 59 is a cross-sectional view taken along lines 59-59 of FIG. 57.
Figure 60:
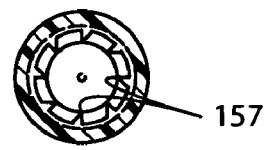
FIG. 60 is a cross-sectional view taken along lines 60-60 of FIG. 57.
Figure 61:
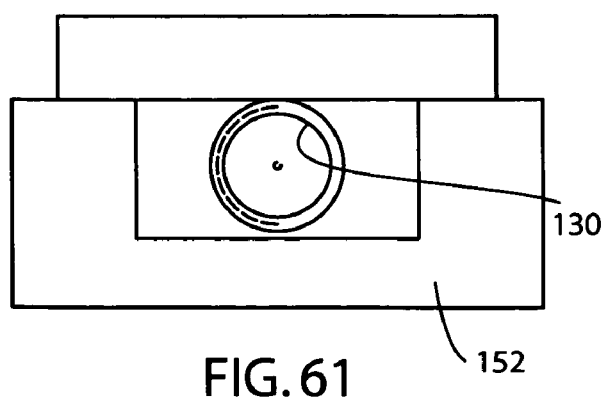
FIG. 61 is a cross-sectional view taken along lines 61-61 of FIG. 57.
Figure 62:
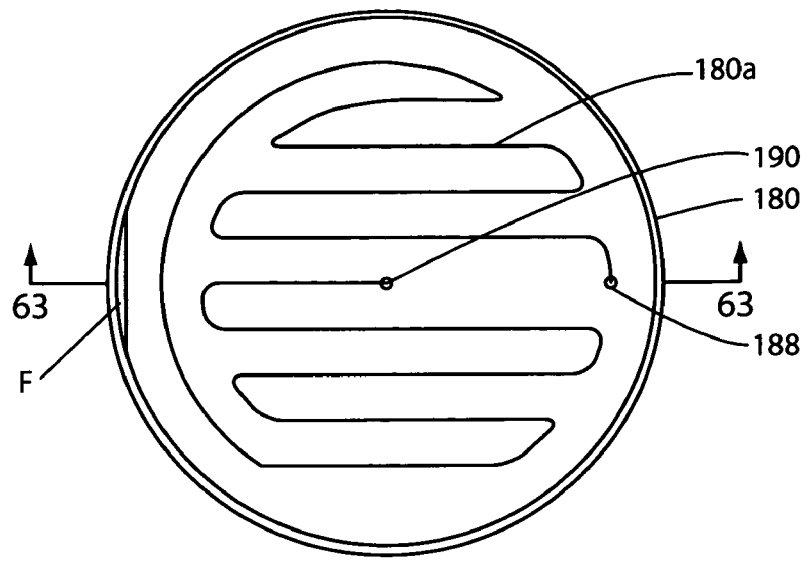
FIG. 62 is a top plan view of the rate control plate of the rate control apparatus of this latest form of the invention.
Figure 63:
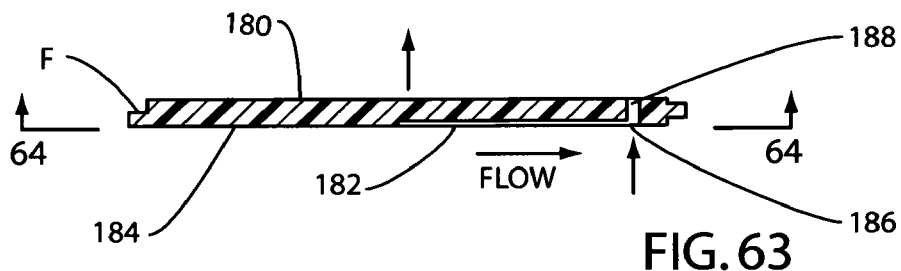
FIG. 63 is a cross-sectional view taken along lines 63-63 of FIG. 62.

Operating shaft 128 includes circumferentially spaced-apart generally arcuate-shaped cavities 131 and 132 that are strategically located to receive the end portion 166*a* of container nipple 166 and also to receive the end portion 172*a* of the rate control means nipple 172 when the operating shaft is held in position within chamber 130 by the retainer clips 125. As best seen in FIG. 57, nipple 172 is affixed to and extends from a cover 173, which forms a part of the rate control assembly 177 of this latest form of the invention. As in the earlier described embodiment, as the operating shaft 128 is rotated by the operating handle from it first position into its second position spring knives 140 will cleanly sever the sealed tip portions 166*a* and 172*a* of nipples 166 and 172 respectively. Continued rotation of the operating member will capture the tip portions within the cavities for rotation therewith and will move transverse passageway 136 into alignment with fluid passageways 166*p* and 172*p* of the respective nipples. With the operating member in this position fluid can flow freely from reservoir 168 toward the rate control means of the invention via passageways 166*p* and 172*p* of nipples 166 and 172 and 136 of control shaft 128.

Figure 64:
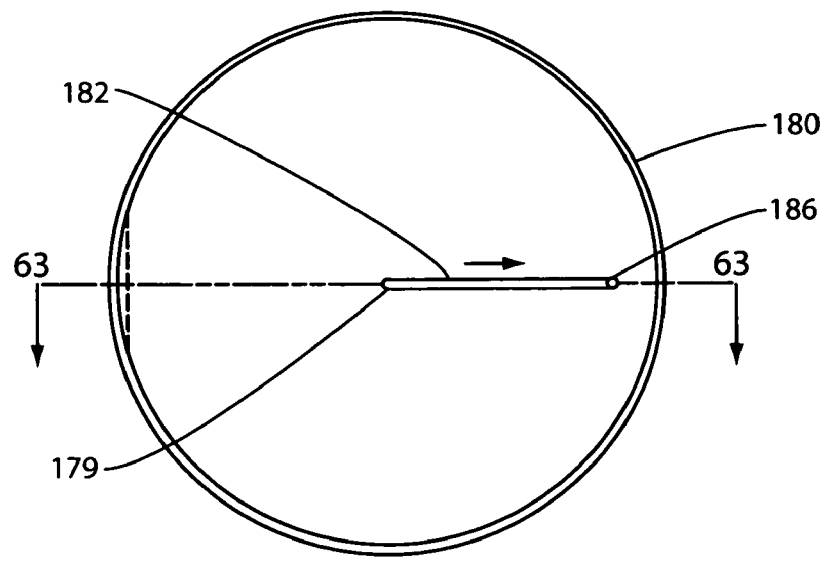
FIG. 64 is a view taken along lines 64-64 of FIG. 63.

From passageway 172*p*, fluid will flow through a conventional particulate filter 111 and then into the inlet 179 of the rate control plate 180 of the rate control assembly 160 (FIG. 64). The fluid will then flow through channel 182 and outwardly of outlet 186. From outlet 186 the fluid will flow into inlet 188 of circuitous flow channel 180*a*. Unlike the rate control plate of the previously described embodiment of the invention, rate control plate 180 has but a single micro-channel 180*a*. It is apparent that by varying the geometry of the micro-channel, including its length, depth, width and geometry, the rate of fluid flow from reservoir 168 toward the administration set of the apparatus can be precisely controlled. After flowing through the rate control channel 180*a*, fluid will flow through outlet 190 of the rate control plate and into inlet 192*a* formed in the upper plate 192 of the rate control assembly. After rate control cover 196 has been mated with upper plate 192 in the manner shown in FIGS. 52 and 56, the administration line 76*a* of the administration set 76 can be unwound from the periphery of the upper plate 192 and the hub portion 77 of the administration set can be inserted into the socket 196*a* formed in cover 196. With the administration set thusly interconnected with the rate control assembly, the fluid will flow from inlet 192*a* into the inlet 76*c* of the administration set and onward toward the patient at a precisely controlled rate.

Figure 65:
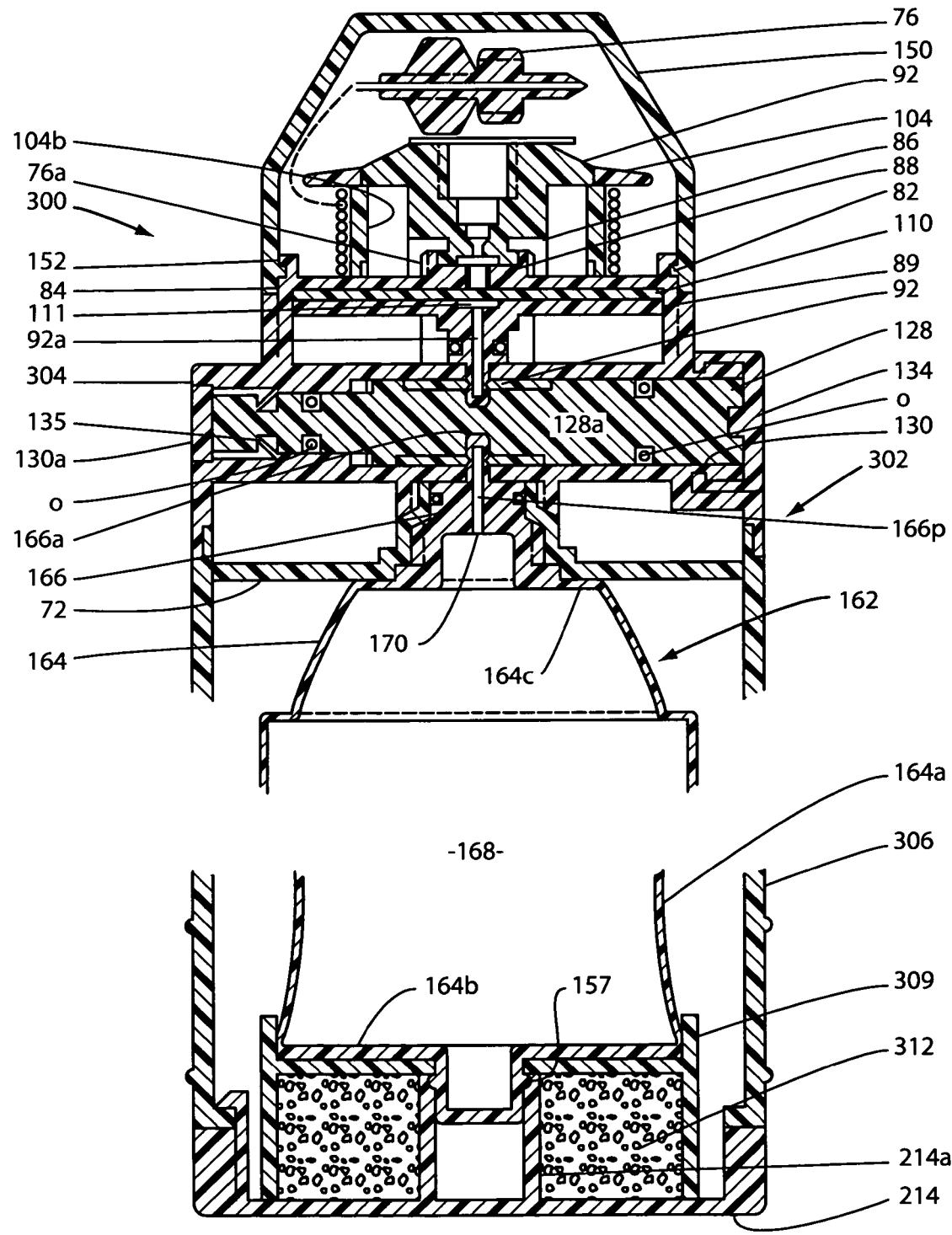
FIG. 65 is a longitudinal, cross-sectional view of yet another form of the dispensing apparatus of the invention showing the reservoir in a pre-filled condition.
Figure 66:
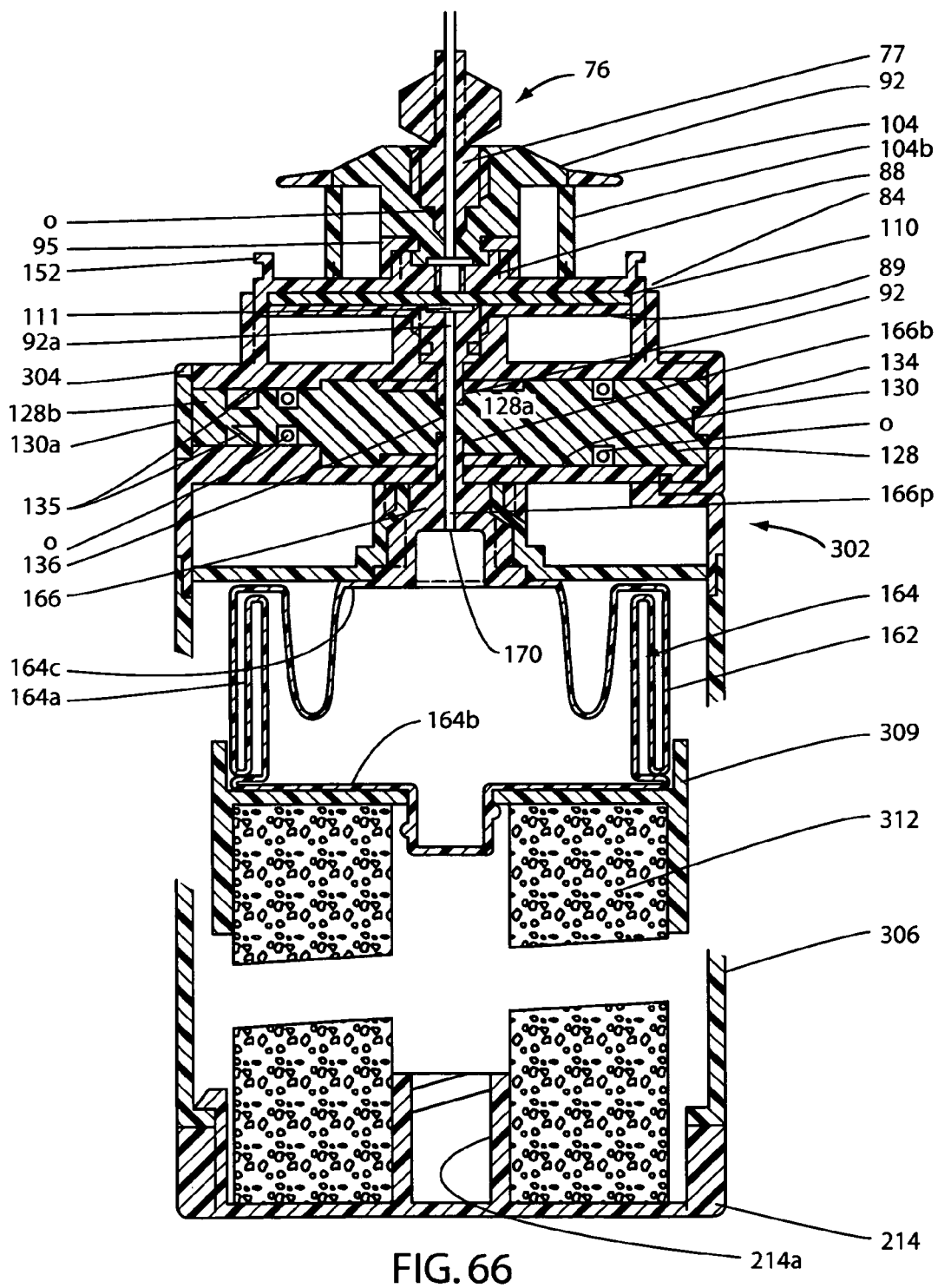
FIG. 66 is a longitudinal, cross-sectional view similar to FIG. 65, but with the reservoir in a substantially empty condition showing the configuration of the apparatus after the fluid dispensing step.
Figure 67:
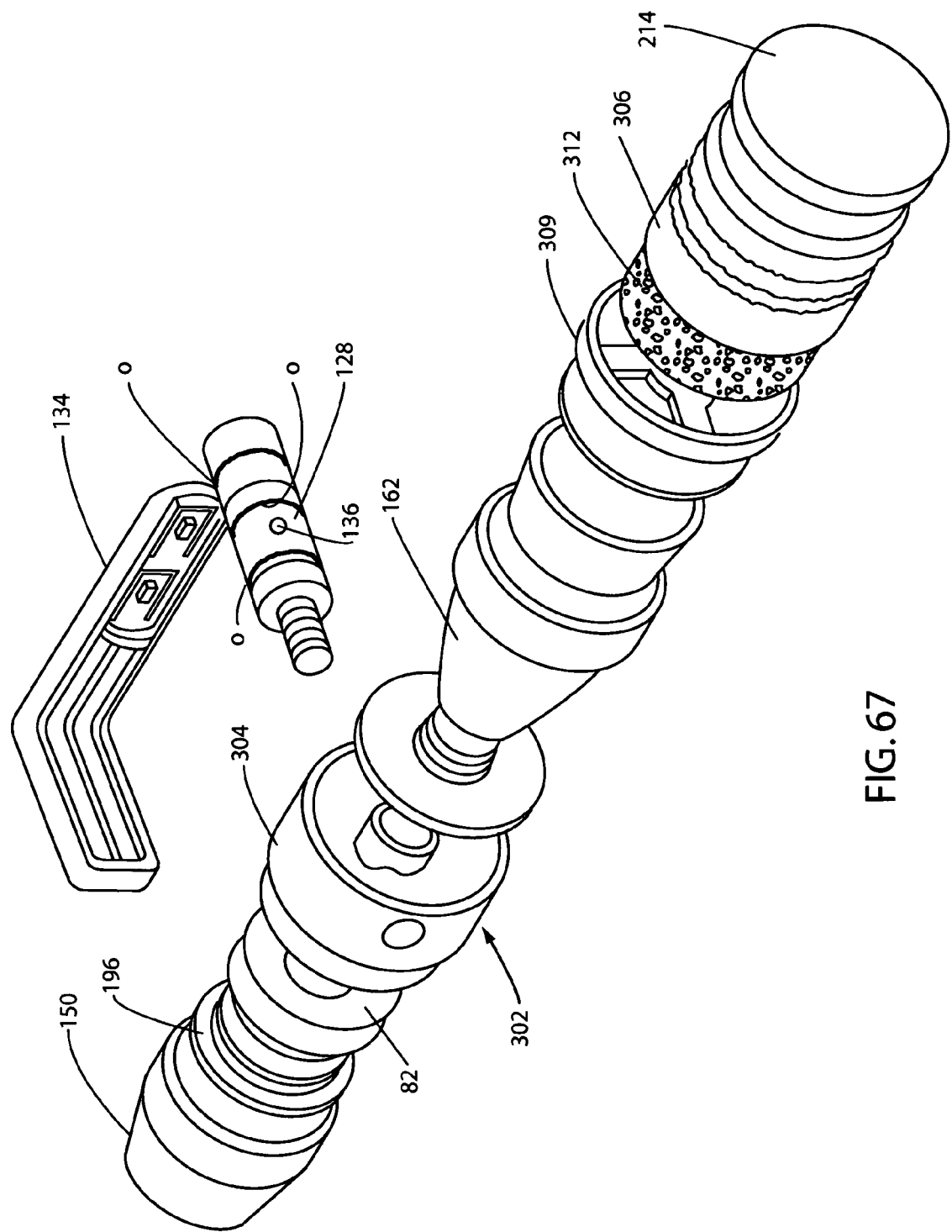
FIG. 67 is a generally perspective, exploded view of the apparatus shown in FIG. 65.

Turning now to FIGS. 65, 66 and 67, an alternate form of the dispensing apparatus of the present invention for dispensing medicaments to a patient is there shown and generally designated by the numeral 300. This alternate form of the dispensing apparatus is similar in many respects to the previously described embodiments and like numerals are used in FIGS. 65 through 67 to identify like components. As before, the dispensing apparatus here includes a supporting structure 302 which includes an upper portion 304 and a generally cylindrically shaped skirt portion 306 that is interconnected with the upper portion in the manner best seen in FIG. 65 of the drawings.

Disposed within skirt portion 306 is a carriage assembly 309 which is movable between a first position shown in FIG. 65 and a second position shown in FIG. 66. Carriage assembly 309 is of similar construction and operation to that previously described and is releasably locked in its first position by locking means also similar to the locking means previously described herein. As before, the locking means secures the carriage assembly and until released prevents forced loading of the reservoir assembly.

The primary difference between this latest form of dispensing apparatus of the invention and that previously described resides in the provision of a novel stored energy source, which is of a totally different construction. More particularly, rather than being of a mechanical spring, the novel stored energy means of this latest form of the invention comprises a compressible, expandable sponge-like configuration, which is generally designated in the drawings by 312. This unique stored energy source, which functions to move the carriage 309 in the first compressed position shown in FIG. 65 to the second expanded position shown in FIG. 66 can take several forms. By way of non-limiting example, stored energy source 312 can comprise a microporous, mesoporous, macroporous, ordered structure and can be constructed from Polypropylene (PP), Ultra High Molecular Weight Polyethylene (UHMWPE), High Density Polyethylene (HDPE), Polyvinylidene Fluoride (PVDF), Ethyle-vinyl Acetate (EVA), Styrene Acrylonitrile (SAN), Polytetrafluroethylene (PTFE), silicone and porous cellulose acetate. A suitable source of certain of these materials is NUSIL Technology of Carpinteria, Calif. However, practice has shown that any porous plastic material including an open cell, porous foam or sponge-like material is suitable for use in constructing the stored energy source. The stored energy material employed may also be a cellular metal, porous metal, a metal sponge or solid metal foam. The metal foams may be derived from single element or alloys of two or more elements. The metals or alloys comprising the foams may be crystalline or amorphous. They may also have regions that display semi-crystalline characteristics. General examples of these materials include Al, Cu/Al, Sn, Au, Pb, brass, steel and negative Poisson metal foams.

As in the last described embodiment of the invention, reservoir defining assembly 162 here comprises a collapsible container assembly 164, which is of identical construction to that previously described in connection with FIGS. 52 and 54. Container assembly 164 is carried by carriage assembly 309 in the manner illustrated in FIG. 65. Collapsible container assembly 164, which includes a nipple assembly 166, defines a fluid reservoir 168 having an inlet/outlet that is generally identified by the numeral 170.

To control the flow of fluid from reservoir 168 toward the administration set 76 of the invention and then on to the patient, novel fluid flow control means are provided. The fluid flow control means, which is carried by the supporting structure 302 is identical in construction and operation to that previously described in connection with FIGS. 1 through 51. As before, this fluid flow control means here comprises two supporting components, namely a rate control means for controlling the rate of fluid flow from the collapsible reservoir toward the administration set and an operating means for controlling fluid flow between the collapsible reservoir and the rate control means. Because the operating means and the rate control means of this latest form of the invention are substantially identical to those described in connection with the embodiment of the invention shown in FIGS. 1 through 51, these means will not be further described.

In operating the apparatus of this latest form of the invention, with the apparatus in the configuration shown in FIG. 65 and with the fluid reservoir 168 filled with the medicament or diluent to be dispensed to the patient, the dispensing operation can be commenced by removing the top cover 150, which is snapped over a cover connector 152 that protrudes from the rate control cover 84. With a cover removed, the administration line of the administration set 76 can be unwrapped from the sleeve 104b of the selector knob support 104 about which it has been coiled. Removal of the top cover 150 also exposes the selector knob 92 so that the fluid flow rate can be selected by rotating the selector member to the desired flow rate indicated by the indicia imprinted on the rim of the selector knob support 104. With the desired flow rate appropriately set, the operating shaft 128 is next rotated through the use of the operating handle to open communication between the reservoir outlet 170 and passageway 92a of nipple 92 via passageway 166p, which, in turn, is in communication with the rate control assembly of the invention.

Following the controlled rotation of the operating shaft 128, which is interconnected with structural member 304, the carriage locking means of the invention can now be manipulated in a manner to release the carriage from base segment 214 in order to permit the stored energy means, or sponge 312 to move the carriage from the starting position shown in FIG. 65 to the extended position shown in FIG. 66.

As the carriage moves toward its extended position fluid will be controllably expelled from reservoir 168, through the flow control means and on to the administration set in the manner previously described.

Figure 67B:
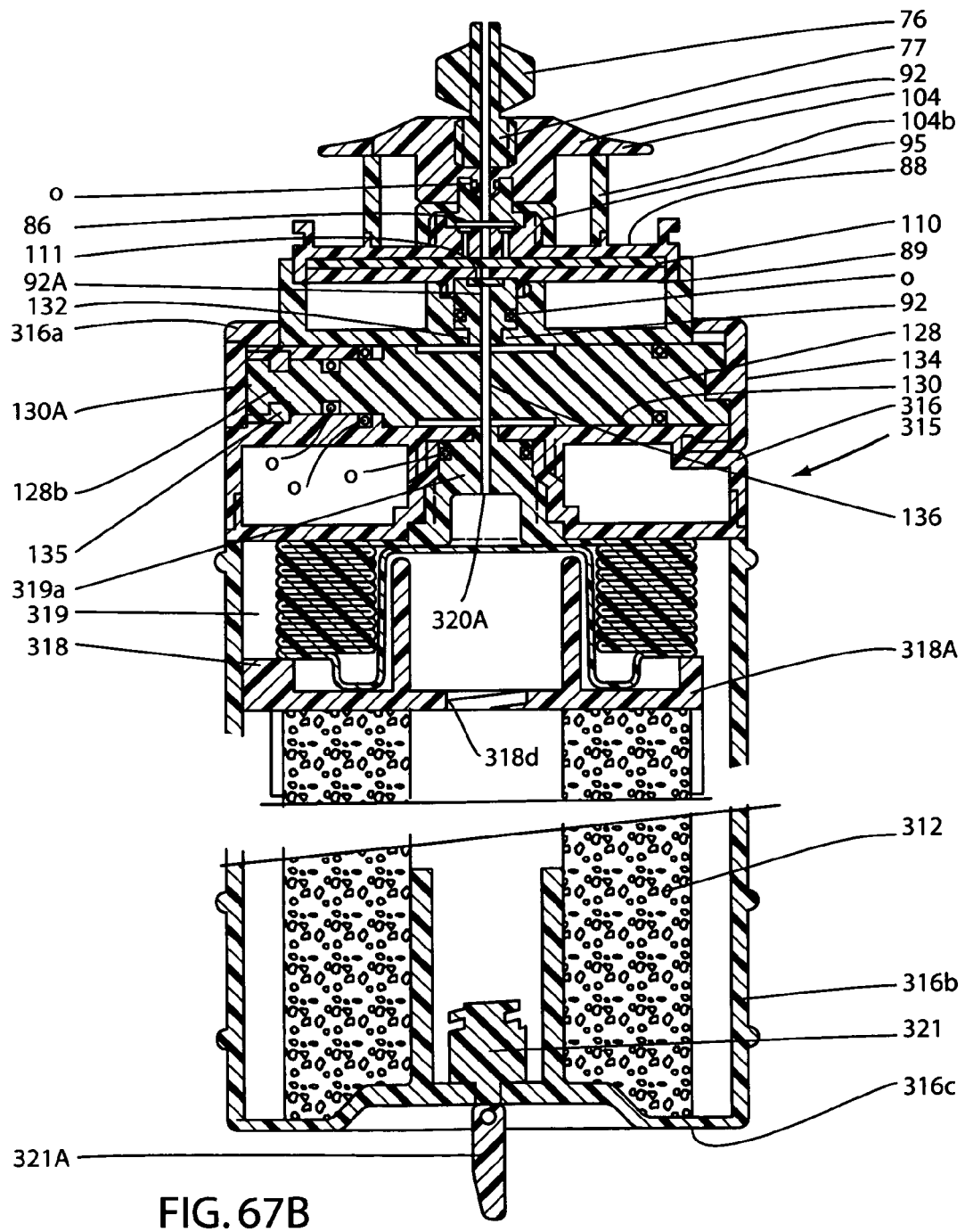
FIG. 67B is a view, similar to FIG. 67A, but showing the configuration of the apparatus after the fluid dispensing step.

Turning now to FIGS. 67A and 67B, yet another form of the dispensing apparatus of the present invention for dispensing medicaments to a patient is there shown and generally designated by the numeral 315. This alternate form of the dispensing apparatus is similar in many respects to the previously described embodiments and like numerals are used in FIGS. 67A and 67B to identify like components. As before, the dispensing apparatus here includes a supporting structure 316 which includes an upper portion 316a and a generally cylindrically shaped skirt portion 316b that is interconnected with the upper portion in the manner best seen in FIG. 67A of the drawings.

Disposed within skirt portion 316b is a carriage assembly 318 which is movable between a first position shown in FIG. 67A and a second position shown in FIG. 67B. Carriage assembly 318 is of similar construction and operation to that previously described and is releasably locked in its first position by locking means somewhat similar to the locking means previously described herein.

The primary difference between this latest form of dispensing apparatus of the invention and that described in connection with FIGS. 65 through 67 resides in the provision of a novel collapsible container 319 which has accordion-wall construction similar to that shown in FIGS. 3 and 6 of the drawings.

Container assembly 319 is carried by carriage assembly 318 in the manner illustrated in FIG. 67A. Collapsible container assembly 319, which includes a nipple assembly 319a, defines a fluid reservoir 320 having an inlet/outlet that is generally identified by the numeral 320a.

To control the flow of fluid from reservoir 320 toward the administration set 76 of the invention and then on to the patient, novel fluid flow control means are provided which are identical in construction and operation to that previously described in connection with FIGS. 1 through 51.

In operating the apparatus of this latest form of the invention, with the apparatus in the configuration shown in FIG. 67A and with the fluid reservoir 320 filled with the medicament or diluent to be dispensed to the patient, the dispensing operation can be commenced by removing the top cover 150, which is snapped over a cover connector 152 that protrudes from the rate control cover 84. With a cover removed, the administration line of the administration set 76 can be unwrapped from the sleeve 104b of the selector knob support 104 about which it has been coiled. Removal of the top cover 150 also exposes the selector knob 92 so that the fluid flow rate can be selected by rotating the selector member to the desired flow rate indicated by the indicia imprinted on the rim of the selector knob support 104. With the desired flow rate appropriately set, the operating shaft 128 is next rotated through the use of the operating handle to open communication between the reservoir outlet 320a, through passageway 166p, passageway 136, and passageway 92a of nipple 92, which, in turn, is in communication with the rate control assembly of the invention.

Following the controlled rotation of the operating shaft 128, the carriage locking means of the invention can now be manipulated in a manner to release the carriage from base segment 316c in order to permit the stored energy means, or sponge 312, to move the carriage from the starting position shown in FIG. 67A to the extended position shown in FIG. 67B.

In this latest form of the invention, the carriage release means comprises a threaded connector boss 321 that is rotatably carried by base segment 316c and is constructed and arranged to threadably engage a threaded aperture 318d formed in the carriage base 318a, with this construction rotation of the threaded boss using pivotal handle 321a, will cause the boss to disengage the base segment permitting the stored energy source to move the carriage toward the position shown in FIG. 67B.

As the carriage moves toward its retracted position, fluid will be controllably expelled from reservoir 320, through the flow control means and on to the administration set in the manner previously described.

Referring next to FIGS. 68, 68A, 68B and 69, still another form of the dispensing apparatus of the present invention for dispensing medicaments to a patient is there shown and generally designated by the numeral 322. This alternate form of dispensing apparatus is similar in some respects to the earlier described embodiments and like numerals are used in FIGS. 68 and 69 to identify like components. Because the flow control means of this latest form of the invention is of different construction and operates in a different way, the dispensing apparatus 322 includes a supporting structure 324, which, is of necessity, somewhat different in construction. More particularly, the supporting structure 324 here comprises a connector assembly 326 and a generally cylindrically shaped outer housing 328 that is interconnected with the connector assembly in the manner best seen in FIG. 68 of the drawings.

Figure 68:
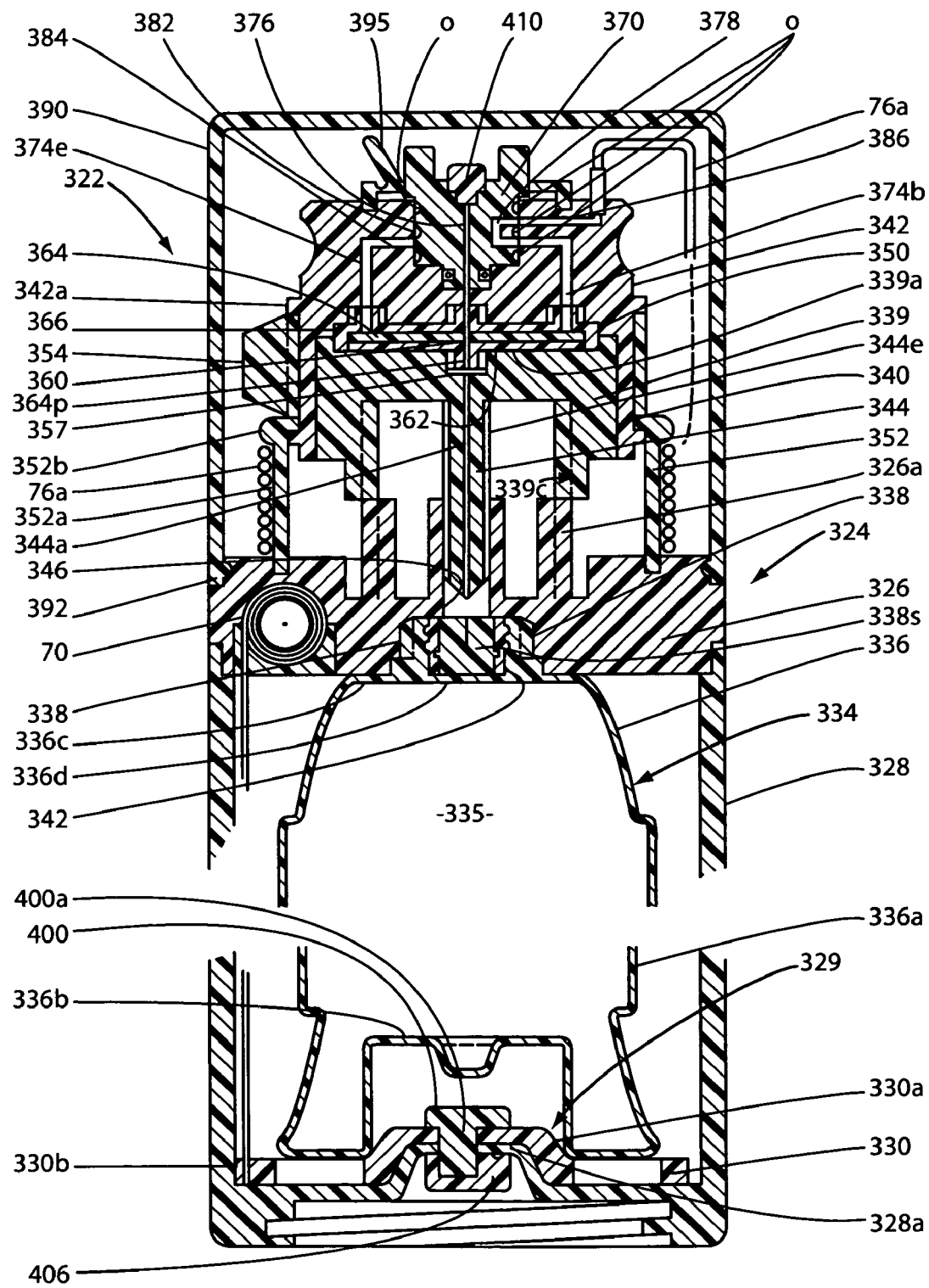
FIG. 68 is a longitudinal, cross-sectional view of still another form of the fluid dispensing apparatus of the invention showing the reservoir in a pre-filled condition.
Figure 69:
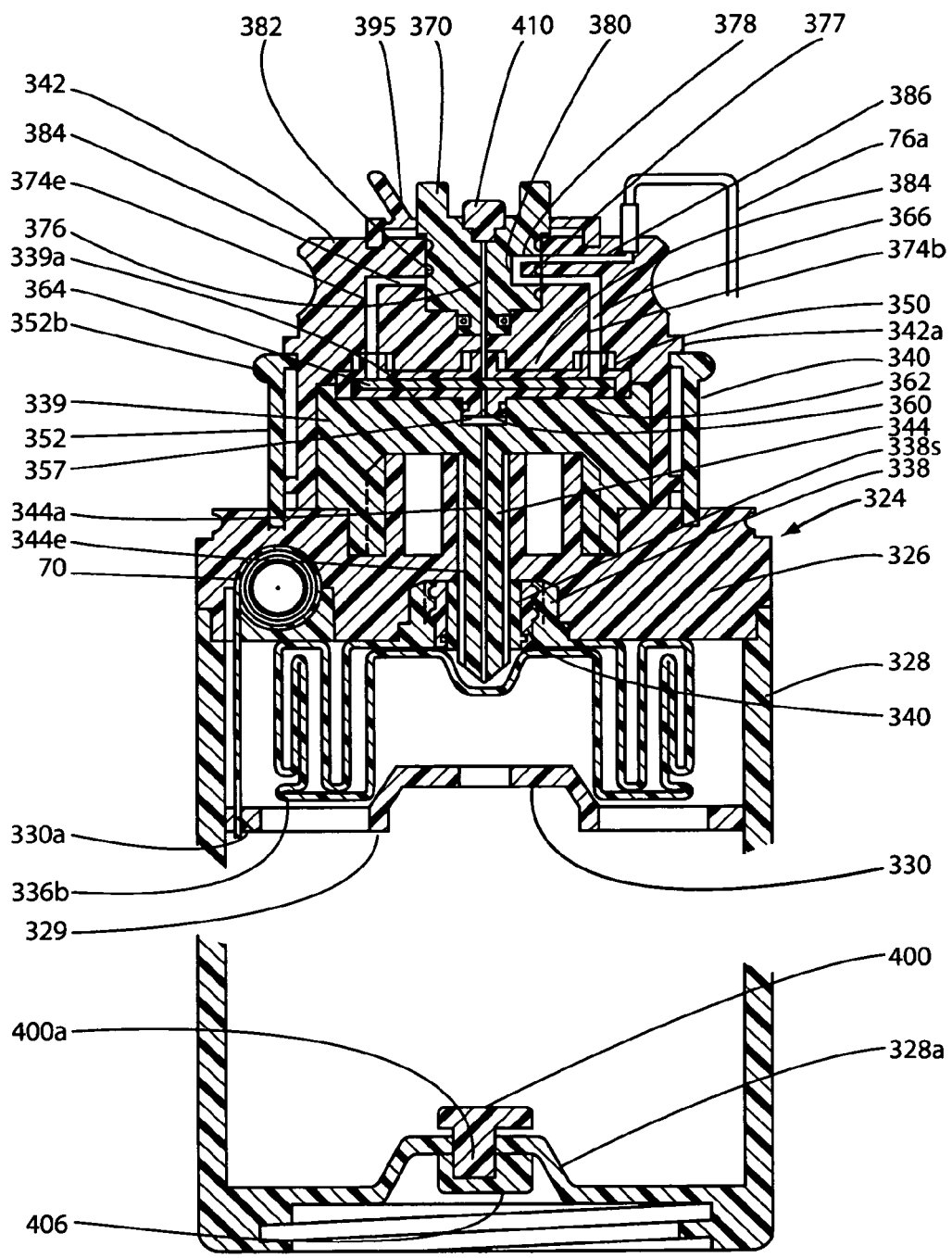
FIG. 69 is a longitudinal, cross-sectional view similar to FIG. 68 but showing the various components of the apparatus as they appear following delivery to the patient of the fluid contained within the apparatus reservoir.

Disposed within outer housing 328 is the carriage assembly, which is movable between a first position shown in FIG. 68 and a second position shown in FIG. 69. Carriage assembly 329 comprises a carriage 330 having a carriage base 330a that has proximate its periphery a connector portion 330b. Carriage assembly 329 is releasably locked to base 328a of outer housing 328 in its first position by a novel locking means the character of which will presently be described.

Carried by carriage assembly 329 is a reservoir defining assembly 334 that defines a fluid reservoir 335. Reservoir defining assembly 334 here includes a collapsible container 336 having a sidewall 336a, an interconnected bottom wall 336b and an interconnected top wall 336c having a thin wall portion 336d to which a sealed reservoir septum assembly 338 is sealably interconnected (see FIG. 68). In a manner presently to be described, fluid reservoir 335 is accessible via a slit septum 338s, which comprises a part of reservoir septum assembly 338. As best seen in FIG. 68, septum 338s is disposed within a generally cylindrically shaped holding ring 342, which in turn is disposed within septum assembly 338.

In the preferred form of this alternate embodiment of the invention, reservoir assembly 334 is formed by the previously described aseptic blow-fill-seal technique to form a hermetically sealed container that contains the fluid to be dispensed.

The primary difference between this latest form of dispensing apparatus of the invention and those previously described herein resides in the provision of a totally different operating means for controlling fluid flow between reservoir 335 and the rate control means of the invention. This important operating means here comprises a septum-penetrating assembly generally designated in FIG. 68 by the numeral 339. Assembly 339, which is disposed within a skirt 340 formed on a selector member housing 342 includes a pointed septum-penetrating member 344 having an elastomeric overcoat 344e, which is received within a guide passageway 346 formed on support member 326. Assembly 339 includes an internally threaded counterbore 339c which threadably mates with externally threaded portion 326a of connector assembly 326. Assembly 339 also includes a cavity 339a, which closely receives a portion of the somewhat differently configured rate control assembly 350, the details of construction of which will presently be described.

In this latest embodiment of the invention, selector member housing 342 along with septum-penetrating assembly 339 is movable within a guide sleeve 352 that extends outwardly from support member 326, from the first position shown in FIG. 68 to the second position shown in FIG. 69. In addition to guiding the travel of the septum-penetrating assembly, guide sleeve 352 defines a cylindrical space 352a about which the administration line 76a of the administration set can be coiled in the manner best seen in FIG. 68.

Figure 69A:
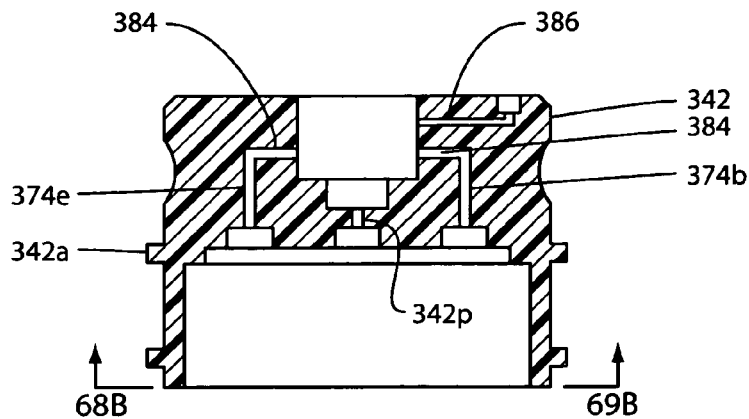
FIG. 69A is an enlarged, cross-sectional view of the selector member housing of the fluid dispensing apparatus.
Figure 69B:
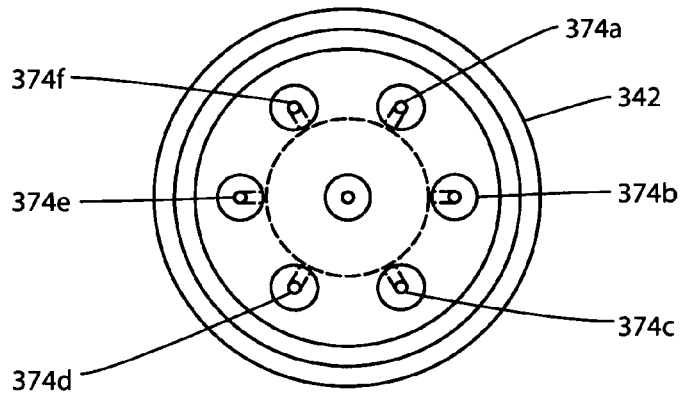
FIG. 69B is a cross-sectional view taken along lines 69B-69B of FIG. 69A.

Selector member housing 342 is retained in its first position by a tear strip 354 that is removably receivable between a circumferentially extending rib 342a formed on housing 342 and the upper extremity 352b of guide sleeve 352. When the tear strip 354 is removed in the manner illustrated in FIG. 68B, a rotational force exerted on selector member housing 342 will move the housing along with the septum-penetrating assembly into the second position shown in FIG. 69 and in so doing will cause the septum-penetrating member 344 to pierce the septum 338s in the manner shown in FIG. 69. Piercing of the septum 338s and thin wall portion 336d opens a fluid communication path from reservoir 335 to the rate control assembly 350 via a central fluid passageway 344a formed in septum-penetrating member 344. As will be described in greater detail hereinafter, from passageway 344a fluid will flow through conventional particulate filter 357, into inlet 360 of rate control cover 362 of the rate control assembly 350, into inlet 364p of rate control plate 364 and then into the various circuitous fluid channels of the rate control plate (see FIG. 69E). The fluid will then flow via the sealably connected rate control cover 366 into the various circumferentially spaced-apart fluid passageways formed in the selector housing 342 (see FIGS. 69A and 69B).

Figure 69C:
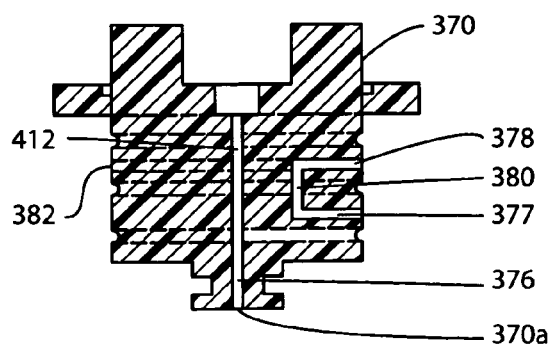
FIG. 69C is an enlarged, cross-sectional view of the selector member of the fluid dispensing apparatus.
Figure 69D:
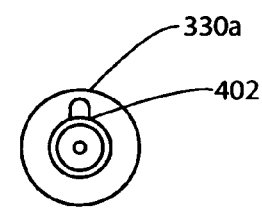
FIG. 69D is a view taken along lines 69D-69D of FIG. 68.
Figure 69E:
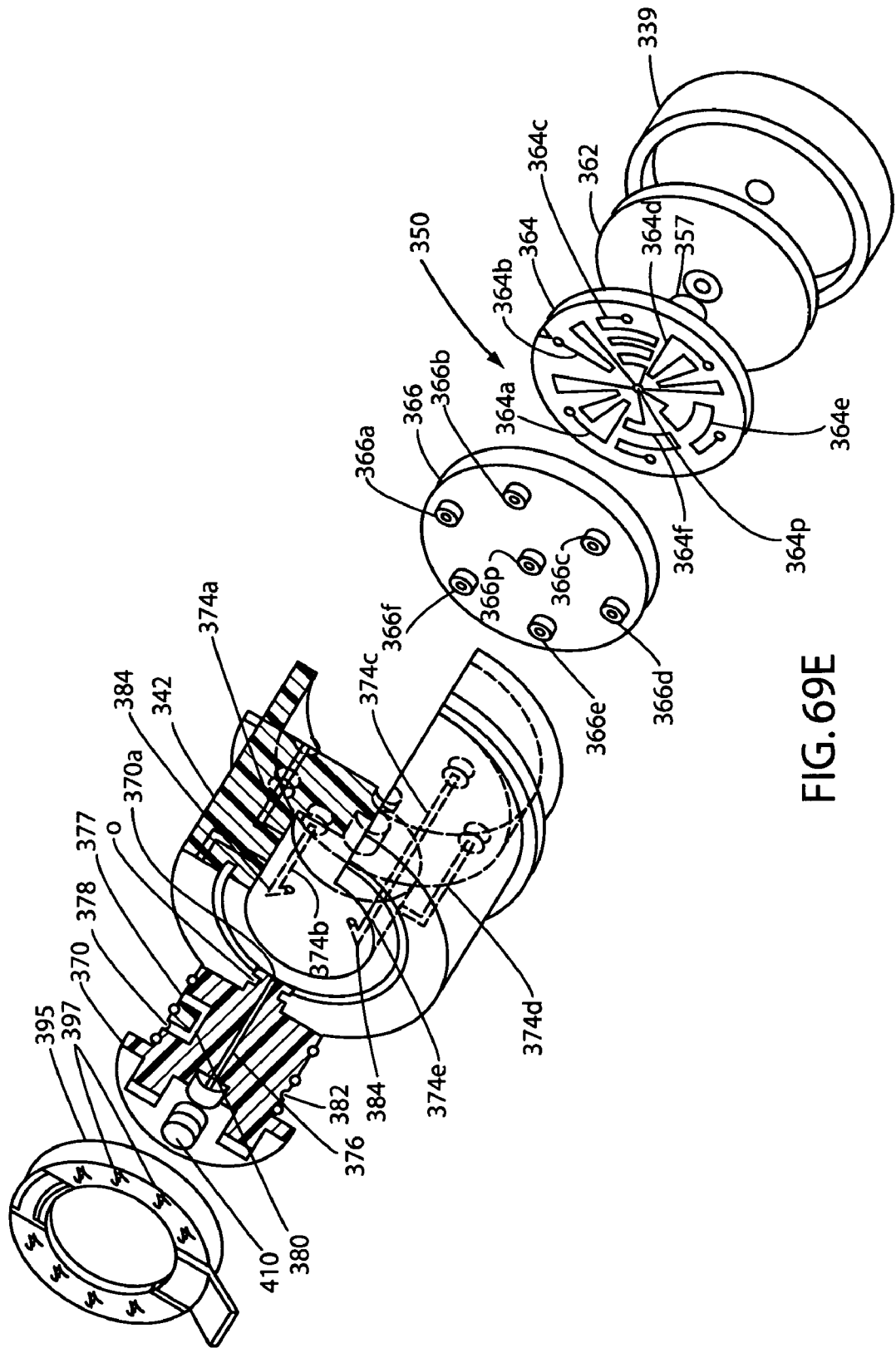
FIG. 69E is an enlarged, generally perspective, exploded view of the rate control portion of the fluid dispensing apparatus shown in FIGS. 68 and 69.

Considering in greater detail the rate control assembly 350 of this latest form of the invention, as shown in FIG. 69E rate control plate 364 is provided with circuitous fluid channels 364a, 364b, 364c, 364d, 364e and 364f, each of which is of a different geometry including channel length, depth, width and geometry. As the fluid flows from reservoir 335 into the inlet 364p of rate control plate 364 via the orifice of the rate control cover 362, each of the circuitous fluid channels will fill with the medicinal fluid to be dispensed to the patient. From the circuitous fluid channels, the fluid will flow into outlet passageways 366a, 366b, 366c, 366d, 366e, 366f and 366p respectively formed in rate control cover 366. From these outlet passageways, the fluid flows into and fills circumferentially spaced-apart fluid passageways 374a, 374b, 374c, 374d, 374e and 374f formed in selector housing 342 (see FIG. 69B).

As best seen by referring to FIGS. 69C and 69E, selector member 370 is provided with an inlet passageway 377 and an outlet passageway 378 that is interconnected with inlet passageway 376 by means of an axially extending stub passageway 380 which, in turn, is connected to a circumferentially extending channel passageway 382 formed in selector member 370 (FIG. 69C). With this construction, by rotating the selector member 370, inlet passageway 377 can be selectively brought into index with one of the radial extensions 384 of the axially extending passageways formed in selector member housing 342 thereby providing fluid communication between outlet passageway 378 and the selected one of the circuitous flow passageways formed in rate control plate 364 via annular channel passageway 382 and the selected axially extending passageway formed in the selector member housing 342. Since outlet passageway 378 is in fluid communication with the administration set 76 of the invention via passageway 386 (FIG. 69A), the rate of fluid flow toward the patient can be precisely controlled by selecting a rate control passageway of appropriate configuration and length that is formed in rate control plate 364.

With the apparatus in the configuration shown in FIG. 68, and with the fluid reservoir 335 filled with the medicament or diluent to be dispensed to the patient, the dispensing operation can be commenced by removing the top cover 390, which is snapped over a cover connector 392 that is provided on connector member 326. With the cover removed, the administration line 76a of the administration set 76 can be unwrapped from the selector member housing about which it has been coiled. Removal of the top cover 390 also exposes the selector member 370, which is secured in position by a selector member retainer component 395, so that the fluid flow rate can be selected by rotating the selector member to the desired flow rate indicated by the indicia 397 imprinted on the selector member retainer component.

In the manner previously described, movement within guide sleeve 352 of the selector member housing 342, along with septum-penetrating assembly 339 from the first position shown in FIG. 68 to the second position shown in FIG. 69 opens fluid communication between reservoir 335 and the rate control assembly 350. This done, the carriage locking means of this latest form of the invention can be manipulated in a manner to release the carriage 330 from base member 328a in order to permit the stored energy means, or springs 70, to move the carriage from the starting position shown in FIG. 68 to the position shown in FIG. 69.

In this regard, as indicated in Figures and 68, 69 and 69D the carriage locking means includes a locking member 400 having a shank portion 400a which extends through a keyhole-shaped opening 402 provided in the carriage base 330a (see FIG. 69D). The carriage locking means also includes a finger-engaging, operating member 406 that is connected to shank portion 400a. Operating member 406 functions to rotate locking member 400 from a transverse locking position to a release position in alignment with keyhole opening 402 formed in carriage base 330a. As the operating member is rotated from a locked position to a release position, the stored energy means, or springs 70 (FIGS. 68 and 69) will move the carriage from a position shown in FIG. 68 into the position shown in FIG. 69 and in so doing will urge the fluid contained within reservoir 335 to flow toward penetrating member 344, into passageway 344a formed in the penetrating member and into the inlet of rate control cover 362 via filter 357 of the rate of control assembly 350. The fluid will then flow into the various circuitous fluid channels formed in the rate control plate and then into the various outlet passageways formed in rate control cover 364. From the rate control cover, the fluid will flow into the various circumferentially spaced-apart fluid passageways formed in the selector housing 342 (see FIGS. 69A and 69B). By rotating the selector member 370, inlet passageway 377 of selector member 370 can be selectively brought into index with one of the radial extensions 384 formed in selector member housing 342 thereby providing fluid communication between outlet passageway 378 and the selected one of the circuitous flow passageways formed in the rate control plate. From outlet passageway 378 the fluid will flow via passageway 386 toward the patient via the administration set 76.

To recover any medicament that may remain in reservoir 335 following the fluid delivery step, a pierceable septum 410, which is carried by selector member 370, can be conveniently pierced using a conventional syringe, or like apparatus (not shown). Piercing of septum 410 opens communication between reservoir 335 and the syringe via central passageway 376, via the rate control assembly 350, via central passageway 364p and via passageway 344a of penetrating member 344 so that any remaining medicament can be readily extracted from reservoir 335.

Turning now to FIGS. 70 and 71, still another alternate form of the dispensing apparatus of the present invention for dispensing medicaments and diluents to a patient is there shown and generally designated by the numeral 420. This alternate form of the dispensing apparatus is similar in many respects to that shown in FIGS. 68 through 69E and like numerals are used in FIGS. 70 and 71 to identify like components. As before, the dispensing apparatus here includes a supporting structure 324 which includes a connector assembly 326 and a generally cylindrically shaped outer housing 328 that is interconnected with the connector assembly in the manner best seen in FIG. 70 of the drawings.

Disposed within wall portion 328 is a carriage assembly 329 which is movable between a first position shown in FIG. 70 and a second position shown in FIG. 71. Carriage assembly 329 is of identical construction and operation to that previously described and is releasably locked in its first position by locking means also identical to the locking means previously described herein.

The primary difference between this latest form of dispensing apparatus of the invention and that previously described resides in the provision of a reservoir defining assembly 422 of a totally different construction. Reservoir defining assembly 422 here comprises a collapsible container assembly 424, which is carried by carriage assembly 329 in the manner illustrated in FIG. 70.

As best seen by referring to FIGS. 70 and 71, collapsible container assembly 424 includes a collapsible, accordion, or bellows-like sidewall 424a, an interconnected bottom wall 424b and an interconnected top wall 424c having a thin wall portion 424t to which a sealed reservoir septum assembly 424d is integrally formed (see FIG. 68). Reservoir septum assembly 424d is substantially identical to the reservoir septum assembly previously described and includes a slit septum 424s, which provides access to the fluid reservoir 425 of collapsible container assembly 424 of this latest form of the invention. As before, septum assembly 424d is preferably sealably interconnected with top wall 424c in accordance with the previously described aseptic blow-fill-seal technique.

As in the earlier described embodiment, selector member housing 342 is retained in its first position by a tear strip 354. When the tear strip is removed, a rotary force exerted on selector member housing 342 will move the internally threaded penetrating assembly 339 into the second position shown in FIG. 71 and in so doing will cause the penetrating member 344 to pierce the septum 424s. Movement within guide sleeve 352 of the selector member housing 342, along with septum-penetrating assembly 339 from the first position shown in FIG. 70 to the second position shown in FIG. 71 opens fluid communication between reservoir 425 and the rate control assembly 350, which is identical in construction and operation to that previously described. This done, the carriage locking means of this latest form of the invention, which is also identical in construction and operation to that previously described, can now be manipulated in a manner to release the carriage 330 from base member 328a.

Once again, in order to controllably move the carriage assembly from its first position to its second position, novel stored energy means are provided. This novel stored energy means, which is operably associated with carriage assembly 330, is here provided in the form of three constant force springs 70 which are of identical construction and operation to those previously described. As the carriage assembly moves toward its deployed position, the collapsible sidewall 424a of the collapsible container assembly 424 will move into the collapsed configuration shown in FIG. 71. As the collapsible container collapses, the medicinal fluid contained within the container reservoir will be substantially controllably expelled therefrom.

From reservoir 425, the fluid will flow through penetrating member 344, through conventional particulate filter 357, through the rate control assembly 350, through the selector member 370 and toward the patient via the administration set 76.

Figure 72:
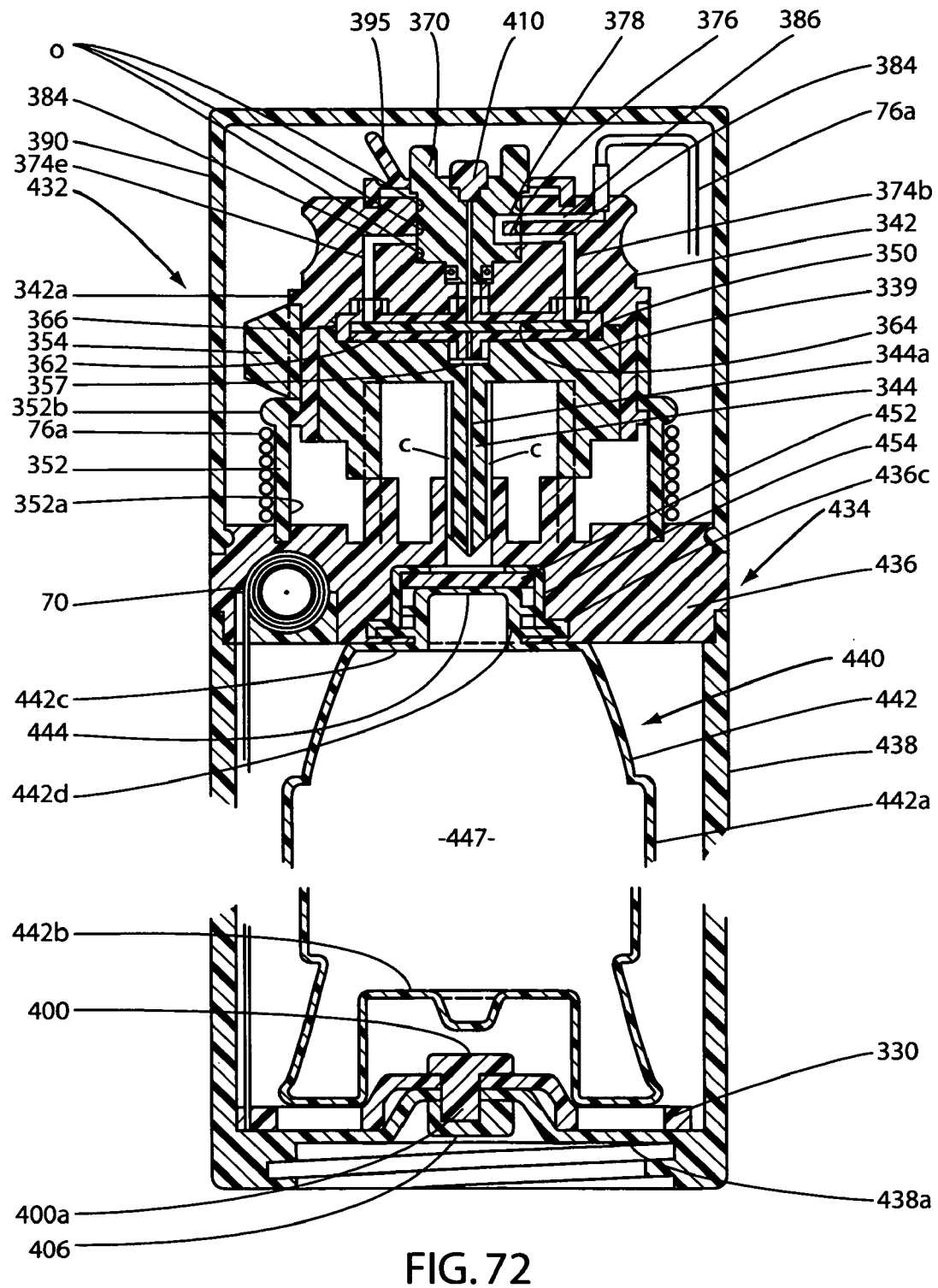
FIG. 72 is a foreshortened, longitudinal, cross-sectional view of yet another alternate form of the fluid dispensing apparatus of the invention showing the reservoir in a filled condition.
Figure 73:
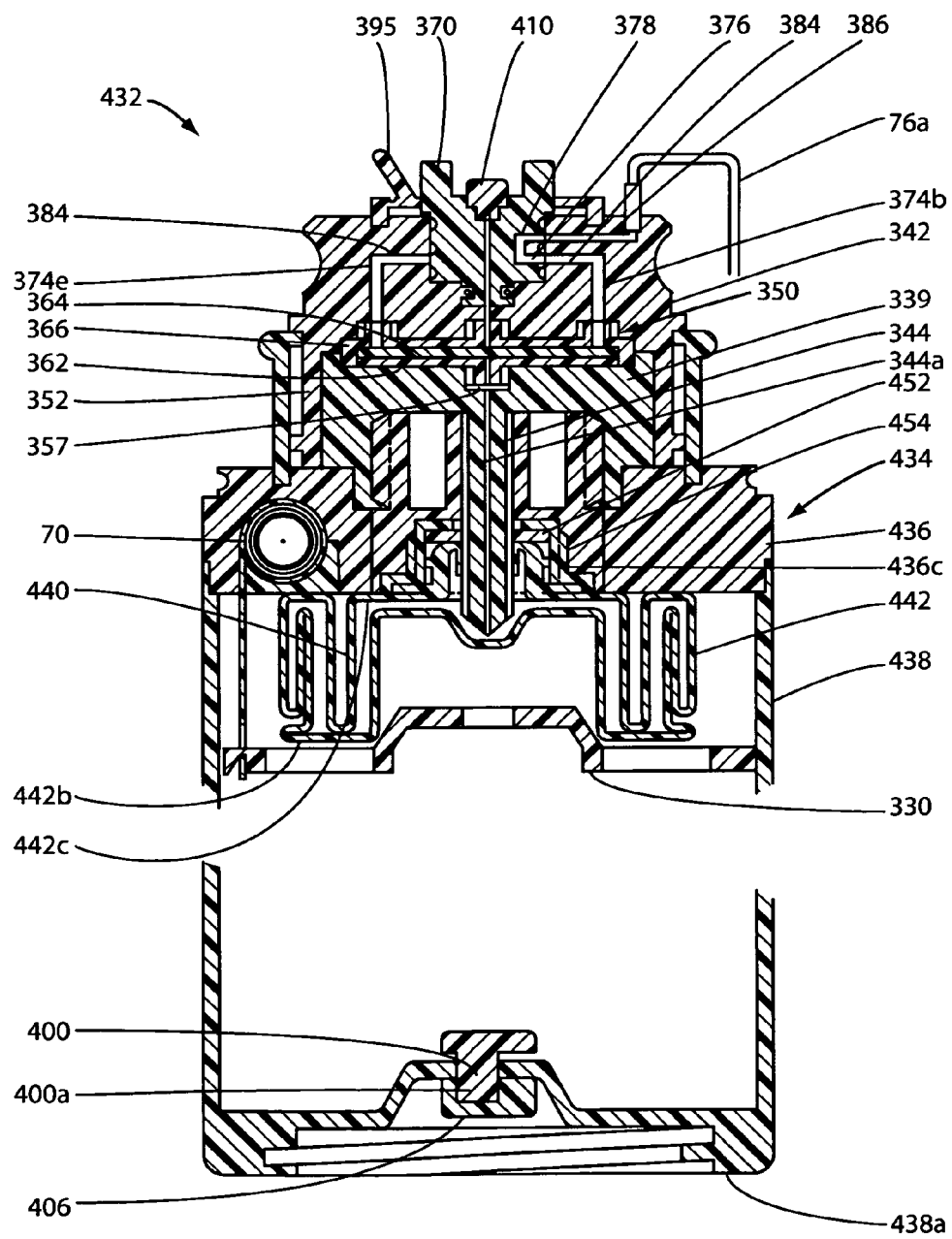
FIG. 73 is a foreshortened, longitudinal, cross-sectional view similar to FIG. 72, but showing the various components of the apparatus as they appear following delivery to the patient of the fluid contained within the apparatus reservoir which is substantially empty.

Turning next to FIGS. 72 through 77, still another form of the dispensing apparatus of the present invention for dispensing medicaments to a patient is there shown and generally designated by the numeral 432. This alternate form of dispensing apparatus is similar in some respects to that shown in FIGS. 70 and 71 and like numerals are used in FIGS. 72 through 77 to identify like components. As best seen in FIGS. 72 and 73 the supporting structure 434 is similar in many respects to the previously described supporting structures and here comprises a connector assembly 436 and a generally cylindrically shaped outer housing 438 that is interconnected with the connector assembly in the manner best seen in FIG. 72 of the drawings.

Disposed within outer housing 438 is the carriage assembly 330, which is of identical construction and operation to that previously described and is releasably locked in its first position by locking means also identical in construction and operation to the locking means previously described herein. Carried by carriage assembly 330 is a reservoir defining assembly 440 which is of a somewhat different construction. This important reservoir defining assembly here includes a collapsible container assembly 442 having a sidewall 442a, an interconnected bottom wall 442b, an interconnected top wall 442c having a thin wall portion 444 and an interconnected neck portion 442d which is sealed at the time of manufacture by the previously discussed blow-fill-seal technique to form a hermetically sealed liquid filled container. Neck portion 442d forms a part of the novel reservoir access means of the invention. Collapsible container assembly 442 defines a fluid reservoir 447 that, in a manner presently to be described, is accessible via a penetrating member 344 that is adapted to pierce closure wall 444 as well as a pierceable septum membrane 452 which is positioned over closure wall 444 by means of a closure cap 454 which is affixed to the neck portion 442d of container assembly 442 (see FIGS. 72 and 73). Penetrating member 344, pierceable membrane 452 and threaded closure cap 454 also form a part of the novel reservoir access means of the invention (FIG. 75).

In the preferred form of this latest alternate embodiment of the invention, closure wall 444 is sealably interconnected with neck portion 442d in accordance with the previously described aseptic blow-fill-seal technique.

The primary difference between this latest form of dispensing apparatus of the invention and those previously described herein resides in the somewhat differently configured container assembly 442. In constructing the container assembly 442, the basic container is formed using the aseptic blow-fill-seal technique earlier described herein and the reservoir portion of the container is sealed by the thin closure wall portion 444. The piercable membrane 452 is then positioned over the closure wall 444 and the cap 454 is positioned over the piercable membrane 452 and secured to neck portion 442d by any suitable means such as adhesive bonding or sonic welding.

This done the container assembly 440 is interconnected with connector member 436 by threading cap 454 into threaded counterbore 436c.

Once again, in order to controllably move the carriage assembly from its first position to its second position, novel stored energy means are provided. This novel stored energy means, which is operably associated with carriage assembly 330, is here provided in the form of three constant force springs 70, which are also identical construction and operation to that previously described.

As in the earlier described embodiments of the invention, when the locking means of the invention is manipulated in a manner to unlock the carriage assembly from base portion 438a of the outer housing 438 to arm the apparatus constant force springs 70 will move from their extended position shown in FIG. 72 to their retracted position shown in FIG. 73 and in so doing will controllably apply a substantially constant force to the carriage to move the carriage assembly from its fully deployed or extended starting position shown in FIG. 72 to its fully retracted position shown in FIG. 73. Following operation of the operating means the carriage assembly can then move toward its retracted position at which time the sidewall 442a of the collapsible container 442 will be urged to move into the collapsed configuration shown in FIGS. 73 and 77. As the collapsible container collapses, the medicinal fluid contained within the container will be substantially expelled in a controlled manner therefrom.

To control the flow of medicinal fluid or diluent from reservoir 447 toward the administration set 76 of the invention and then on to the patient, flow control means are provided. Once again, this novel fluid flow control means, comprises two cooperating components, namely a rate control means for controlling the rate of fluid flow from the collapsible reservoir and an operating means for controlling fluid flow between the collapsible reservoir and the rate control means. Both the operating means and the rate control means of this latest form of the invention are identical in construction and operation to those described in connection with the embodiment of FIGS. 68 and 69.

As in the earlier described embodiment, selector member housing 342 is retained in its first position by a tear strip 354. When the tear strip is removed, a rotary force exerted on selector member housing 342 will controllably move the housing along with the penetrating assembly into the second position shown in FIG. 73 and in so doing will cause the penetrating member 344 to pierce the membrane, shown here as an elastomeric septum 452 (FIGS. 75 and 76) as well as the closure wall 444 in the manner shown in FIG. 73. Piercing of the septum 452 and the closure wall 444 opens a fluid communication path from reservoir 447 to the rate control assembly 350 via a central fluid passageway 344a formed in penetrating member 344. From reservoir 447, the fluid will flow through central fluid passageway 344a of penetrating member 344, through conventional particulate filter 357, through the rate control assembly 350, through the selector member 370 and toward the patient via the administration set 76.

Referring next to FIGS. 78 through 81, yet another form of the dispensing apparatus of the present invention for dispensing medicaments to a patient is there shown and generally designated by the numeral 452. This alternate form of dispensing apparatus is similar in most respects to that shown in FIGS. 73 through 77 and like numerals are used in FIGS. 78 through 81 to identify like components. The major difference between this latest embodiment of the invention and that shown in FIGS. 73 through 77 resides in the differently configured reservoir defining container 454. As shown in FIG. 78 container 454, rather than being in the nature of the collapsible bottle, comprises a reservoir defining unitary container having a continuous bellows-like sidewall 454a that is movable from the expanded, starting configuration shown in FIG. 78 to the collapsed configuration shown in FIG. 79. This important reservoir defining container here includes, in addition to sidewall 454a, an interconnected bottom wall 454b, an interconnected top wall 454c and an interconnected neck portion 454d which is sealed at the time of manufacture by a thin closure wall 455. Neck portion 454d forms a part of the novel reservoir access means of the invention. Collapsible unitary container 454 defines a fluid reservoir 457 that is accessible via a penetrating member 344 that is identical to that previously described. Penetrating member 344 is adapted to pierce closure wall 455 as well as a pierceable membrane 456 which is positioned over closure wall 455 by means of a closure cap 459 which is affixed to the neck portion 454d of container assembly 454 (see also FIGS. 82 and 83).

Figure 79:
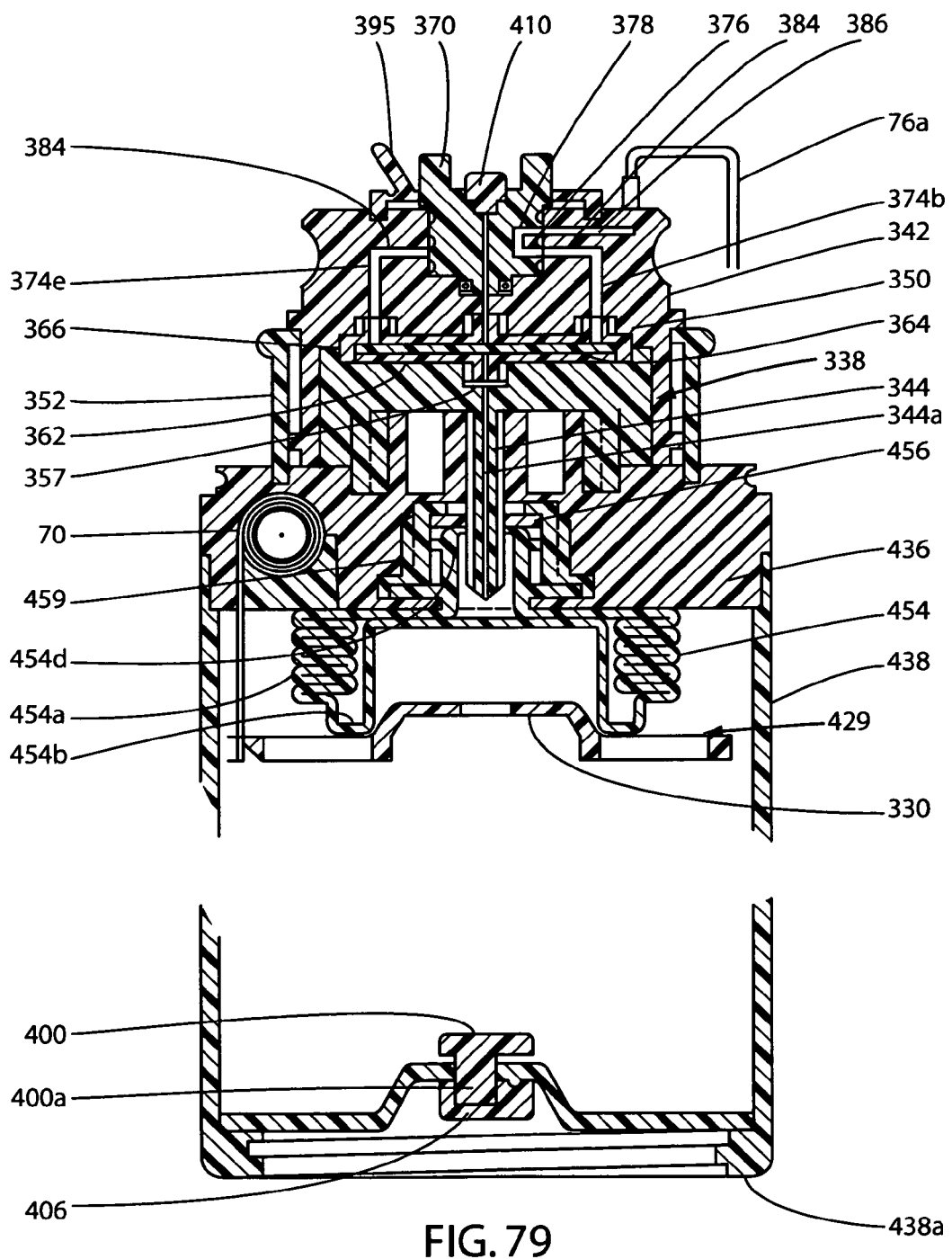
FIG. 79 is a foreshortened longitudinal, cross-sectional view, similar to FIG. 78, but showing the various components of the apparatus as they appear following delivery to the patient of the fluid contained within the apparatus reservoir with the reservoir substantially empty.
Figure 80:
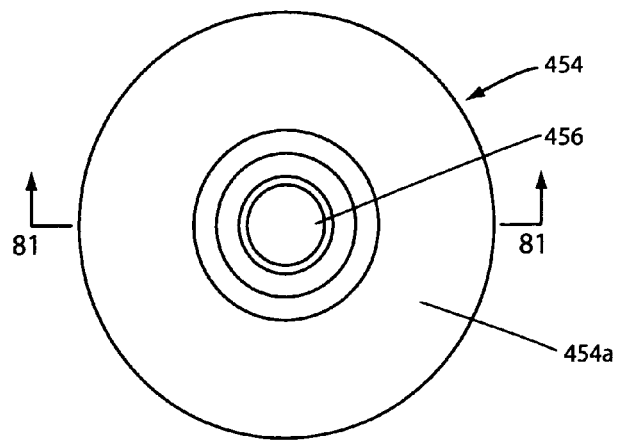
FIG. 80 is a top plan view of the collapsible container of this alternate embodiment of the invention.

As best seen in FIGS. 78 and 79 the supporting structure 434 is substantially identical to the supporting structure of the last described embodiment and here comprises a connector assembly 436 and a generally cylindrically shaped outer housing 438 that is interconnected with the connector assembly in the manner best seen in FIG. 78 of the drawings.

Disposed within outer housing 438 is the carriage assembly 429 which is of identical construction and operation to that previously described and is releasably locked in its first position by locking means also identical in construction and operation to the locking means previously described herein. Carried by carriage assembly is the previously described reservoir defining container 454.

Figure 82:
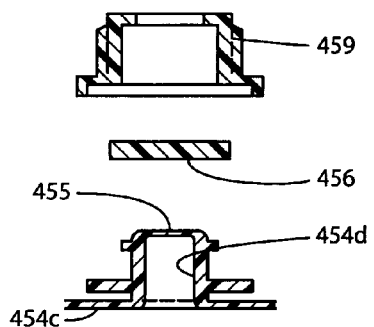
FIG. 82 is an exploded, cross-sectional view of the reservoir access assembly of this latest form of the invention.
Figure 81:
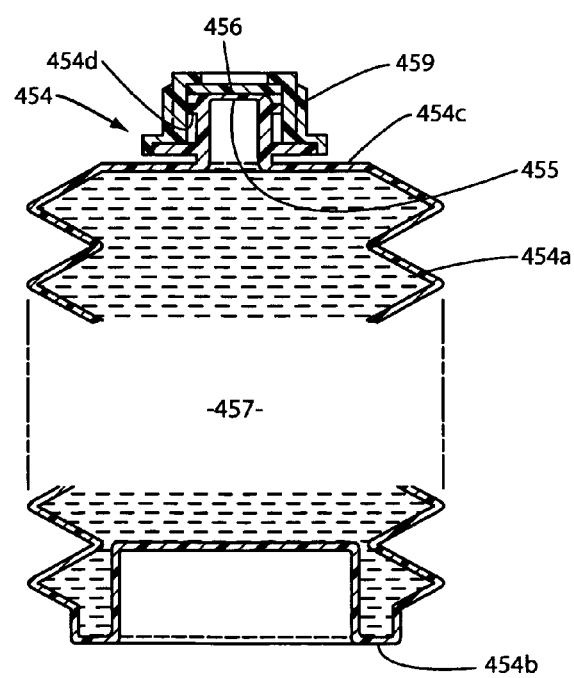
FIG. 81 is a cross-sectional view taken along lines 81-81 of FIG. 80.
Figure 82C:
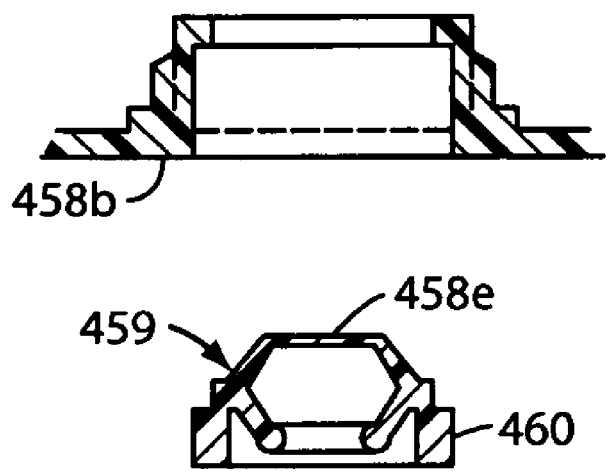
FIG. 82C is a fragmentary, exploded view of the accessing neck assembly of the apparatus shown in FIG. 82A.

As in the last described embodiment of the invention, closure wall 455 is integrally formed with neck portion 454d in accordance with the previously described 454 is formed using the earlier described aseptic blow-fill-seal technique to form a unitary container (FIG. 82).

As before, the basic unitary container and the hermetically sealed reservoir portion of the container is closed by the thin closure wall 455. The piercable septum membrane 456 is then positioned over the closure wall 455 and the cap 459 is positioned over the piercable septum and secured to neck portion 454d by any suitable means such as adhesive bonding or sonic welding. It is to be understood that septum 456 can also be constructed as a slit or partially slit member. It is important to note that closure wall 455 effectively prevents the medicament contained within the fluid reservoir from coming in contact with external contaminants.

Once again, in order to controllably move the carriage assembly from its first position to its second position, novel stored energy means are provided. This novel stored energy means, which is operably associated with carriage assembly 330, is here provided in the form of three constant force springs 70, which are also identical construction and operation to that previously described.

As in the earlier described embodiments of the invention, following operation at the operating means of the invention, when the locking means of the invention is manipulated in a manner to unlock the carriage assembly from base portion 438a of the outer housing 438, springs 70 will move from their extended position shown in FIG. 78 to their retracted position shown in FIG. 79 and in so doing will controllably move the carriage assembly from its starting position shown in FIG. 78 to its fully deployed, reservoir substantially empty position shown in FIG. 79. As the carriage assembly moves toward its deployed position, the sidewall 454a of the collapsible container 454 will move into the collapsed configuration shown in FIG. 79. As the collapsible container collapses, the medicinal fluid contained within the container will be controllably expelled therefrom.

To control the flow of medicinal fluid from reservoir 457 toward the administration set 76 of the invention and then on to the patient, flow control means are provided. Once again, this novel fluid flow control means, comprises two cooperating components, namely a rate control means for controlling the rate of fluid flow from the collapsible reservoir and an operating means for controlling fluid flow between the collapsible reservoir and the rate control means. Both the operating means and the rate control means of this latest form of the invention are identical in construction and operation to those described in connection with the embodiment of FIGS. 68 and 69.

As in the earlier described embodiment, selector member housing 342 is retained in its first position by a tear strip 354. When the tear strip is removed, a rotary force exerted on threaded selector member housing 342 will controllably move the housing along with the penetrating assembly 344 into the second position shown in FIG. 79 and in so doing will cause the penetrating member 344 to pierce the septum 456 as well as the closure wall 455 in the manner shown in FIG. 79. Piercing of the membrane 456 and the closure wall 455 opens a fluid communication path from reservoir 457 to the rate control assembly 350 via a central fluid passageway 344a formed in penetrating member 344. From reservoir 457, the fluid will flow through central fluid passageway 344a of penetrating member 344, through conventional particulate filter 357, through the rate control assembly 350, through the selector member and toward the patient via the administration set 76.

Figure 82D:
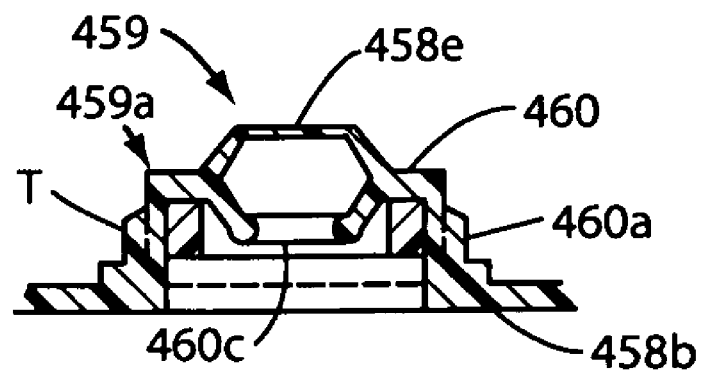
FIG. 82D is a fragmentary view similar to FIG. 82C but showing the neck assembly in an assembled configuration.

Referring next to FIGS. 82A through 82D, yet another form of the dispensing apparatus of the present invention for dispensing medicaments to a patient is there shown. This alternate form of dispensing apparatus is similar in most respects to that shown in FIGS. 78 through 81 and like numerals are used in FIGS. 82A through 82D to identify like components. The major difference between this latest embodiment of the invention and that shown in FIGS. 78 through 81 resides in the somewhat differently configured reservoir defining container 458. More particularly, as shown in FIG. 82A container 458 has a differently configured reservoir accessing neck assembly 458a, which is interconnected with the container top wall 458b. In addition, to top wall 458b the container formed as a unitary structure has a bellows-like sidewall 458c that is movable from the expanded, starting configuration shown in FIG. 82A to the collapsed configuration shown in FIG. 82B and an interconnected bottom wall 458d. Collapsible container 458 defines a fluid reservoir 459 that is accessible via a penetrating member 344 that is identical to that previously described. Penetrating member 344 is adapted to pierce a closure wall 458e that forms an integral part of the sealing portion 460 of the neck assembly. As shown In FIG. 82D, insert component 459 of the neck assembly is interconnected with the neck assembly base portion 460a by an insert molding process or by a subsequent bonding step. With the unique construction thus described, the container of this embodiment need not be sealed at the time of manufacture. Rather, base portion 460a of the neck assembly can be left open and then later sealed by the interconnection therewith of the sealing portion 460.

As best seen in FIG. 82A the supporting structure 434 is substantially identical to the supporting structure of the last described embodiment as is the carriage assembly 429. Carriage assembly 429 is releasably locked in the first position shown in FIG. 82A by locking means which is also identical in construction and operation to the locking means previously described herein. Carried by the carriage assembly is the previously described reservoir defining container 458.

As previously mentioned, a unique feature of this latest embodiment resides in the fact that the basic container 458 can be formed using the earlier described aseptic blow-fill technique, but left unsealed. The container can later be hermetically sealed by mating the sealing portion 460 with the neck base portion 460*a* and then sealably interconnecting the components by any suitable means such as adhesive bonding or sonic welding. However, it is to be understood that, if desired, the sealing portion 460 and the base portion 460*a* can be sealably interconnected during a blow-fill operation.

Once again, in order to controllably move the carriage assembly from its first position to its second position, novel stored energy means are provided. This novel stored energy means, which is operably associated with carriage assembly 330, is here provided in the form of three constant force springs 70, which are also identical in construction and operation to that previously described.

As in the earlier described embodiment, selector member housing 342 is retained in its first position by a tear strip 354. When the tear strip is removed, rotary force exerted on selector member housing 342 will controllably move the housing, along with the penetrating assembly 344 into the second position shown in FIG. 82B and in so doing will cause the penetrating member 344 to pierce the closure wall 458*e* in the manner shown in FIG. 82B. Piercing of the closure wall 458*e* opens a fluid communication path from reservoir 459 to the rate control assembly 350 via a central fluid passageway 344*a* formed in penetrating member 344. From reservoir 459, the fluid will flow through central fluid passageway 344*a* of penetrating member 344, through conventional particulate filter 357, through the rate control assembly 350, through the selector member 370 and toward the patient via the administration set 76. It is to be noted that due to the novel construction of the reservoir accessing means, or neck assembly 458*a*, following penetration of closure wall 458*e*, the elastomeric-coated wall of the penetrating member will sealably engage the inwardly protruding collar 460*c* formed on sealing portion 460 of the neck assembly so as to substantially prevent fluid leakage between the collar and the penetrating member.

As in the earlier described embodiments of the invention, following operation of the operating means of the invention, when the locking means of the invention is manipulated in a manner to unlock the carriage assembly from base portion 438*a* of the outer housing 438, springs 70 will move from their extended position shown in FIG. 82A to their retracted position shown in FIG. 82B and in so doing will controllably move the carriage assembly from its starting position to its fully deployed, reservoir substantially empty position shown in FIG. 82B. As the carriage assembly moves toward its deployed position, the sidewall 458*c* of the collapsible container 458 will move into the collapsed configuration shown in FIG. 82B. As the collapsible container collapses, the medicinal fluid contained within the container will be controllably expelled therefrom.

To control the flow of medicinal fluid from reservoir 459 toward the administration set 76 of the invention and then on to the patient, flow control means are provided. This novel fluid flow control means, is identical in construction and operation to the control means described in connection with FIGS. 78 through 81.

Figure 82E:
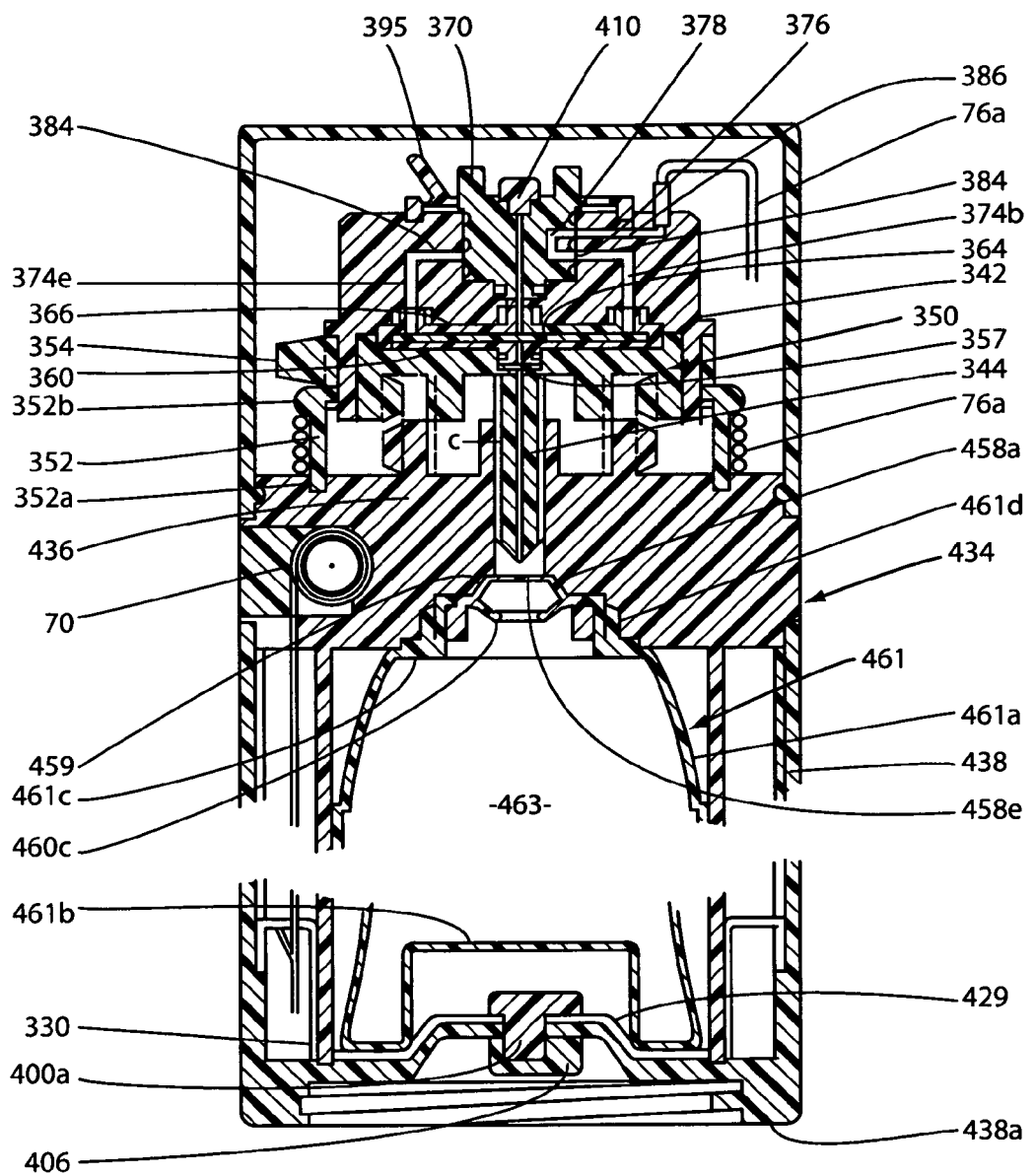
FIG. 82E is a foreshortened, longitudinal, cross-sectional view of still another alternate form of the fluid dispensing apparatus of the invention showing the reservoir in a pre-filled condition.
Figure 82F:
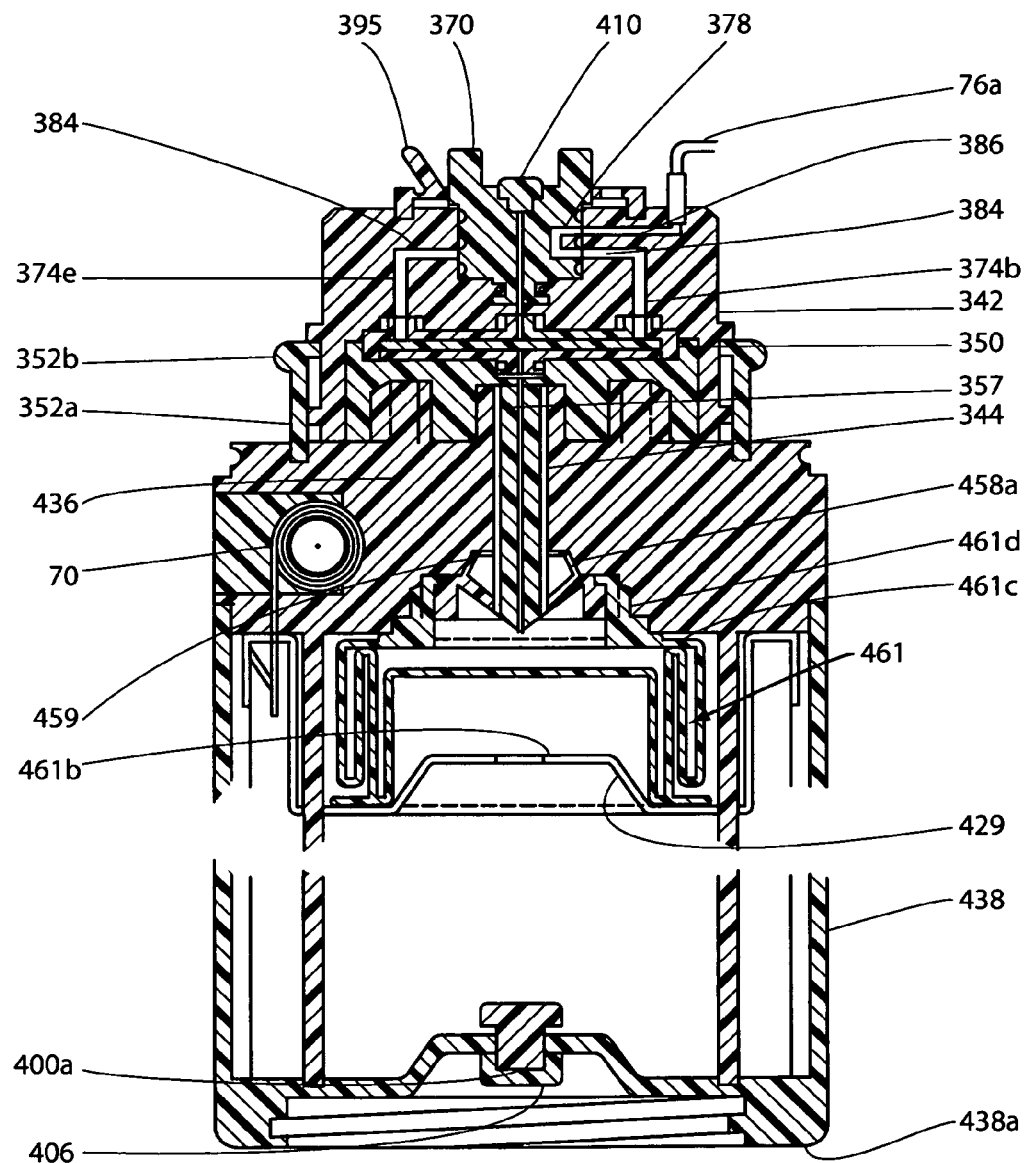
FIG. 82F is a foreshortened, longitudinal, cross-sectional view, similar to FIG. 82E, but showing the various components of the apparatus as they appear following delivery to the patient of the fluid contained within the apparatus reservoir which is substantially empty.

Referring next to FIGS. 82E and 82F, still another form of the dispensing apparatus of the present invention for dispensing medicaments to a patient is there shown. This alternate form of dispensing apparatus is similar in most respects to that shown in FIGS. 82A through 82D and like numerals are used in FIGS. 82E and 82F to identify like components. The major difference between this latest embodiment of the invention and that shown in FIGS. 82A through 82D resides in the somewhat differently configured reservoir defining container 461. As shown in FIG. 82E container 461, rather than being of a bellows-like construction, here comprises a container having a collapsible bottle-like construction as a unitary structure. This reservoir defining, bottle-like container here includes a sidewall 461*a*, an interconnected bottom wall 461*b*, an interconnected top wall 461*c* and an interconnected neck portion 461*d* which is identical to the neck portion 458*a* of the previously described embodiment and is of the construction shown in FIGS. 82C and 82D. Collapsible container 461 defines a fluid reservoir 463 that is accessible via a penetrating member 344 that is identical in construction and operation to that previously described.

As illustrated in FIGS. 82E and 82F the supporting structure 434 is substantially identical to the supporting structure of the last described embodiment as is the carriage assembly 429. Carriage assembly 429 is releasably locked in its first position by locking means also identical in construction and operation to the locking means previously described herein. Carried by carriage assembly is the previously described reservoir defining container 461.

Once again, in order to controllably move the carriage assembly from its first position to its second position, novel stored energy means are provided. This novel stored energy means, which is operably associated with carriage assembly 330, is here provided in the form of three constant force springs 70, which are also identical construction and operation to that previously described.

To control the flow of medicinal fluid from reservoir 463 toward the administration set 76 of the invention and then on to the patient, flow control means are provided. Once again, this novel fluid flow control means is identical in construction and operation to those previously described.

Figure 83:
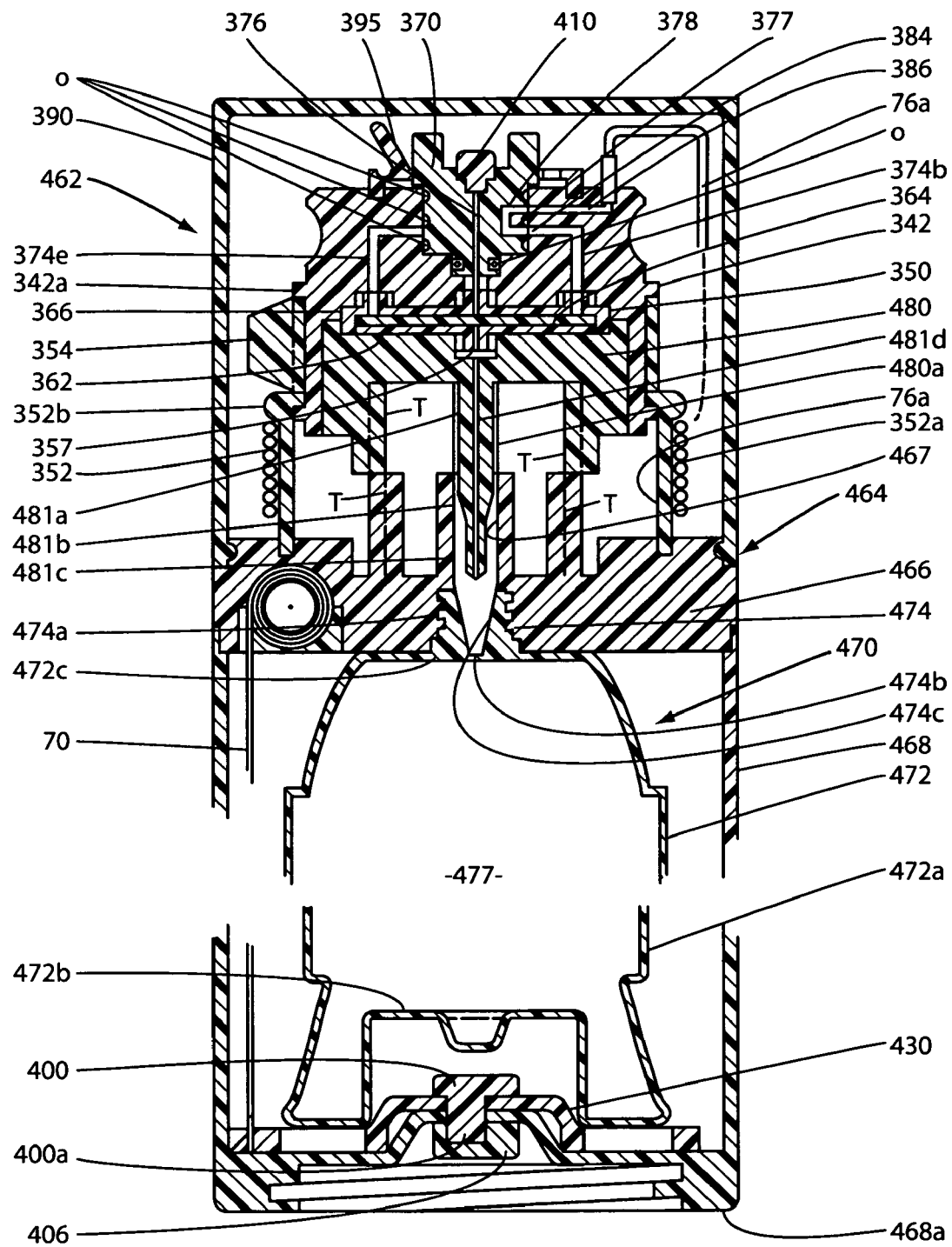
FIG. 83 is a cross-sectional view of still another form of the dispensing apparatus of the invention.
Figure 84:
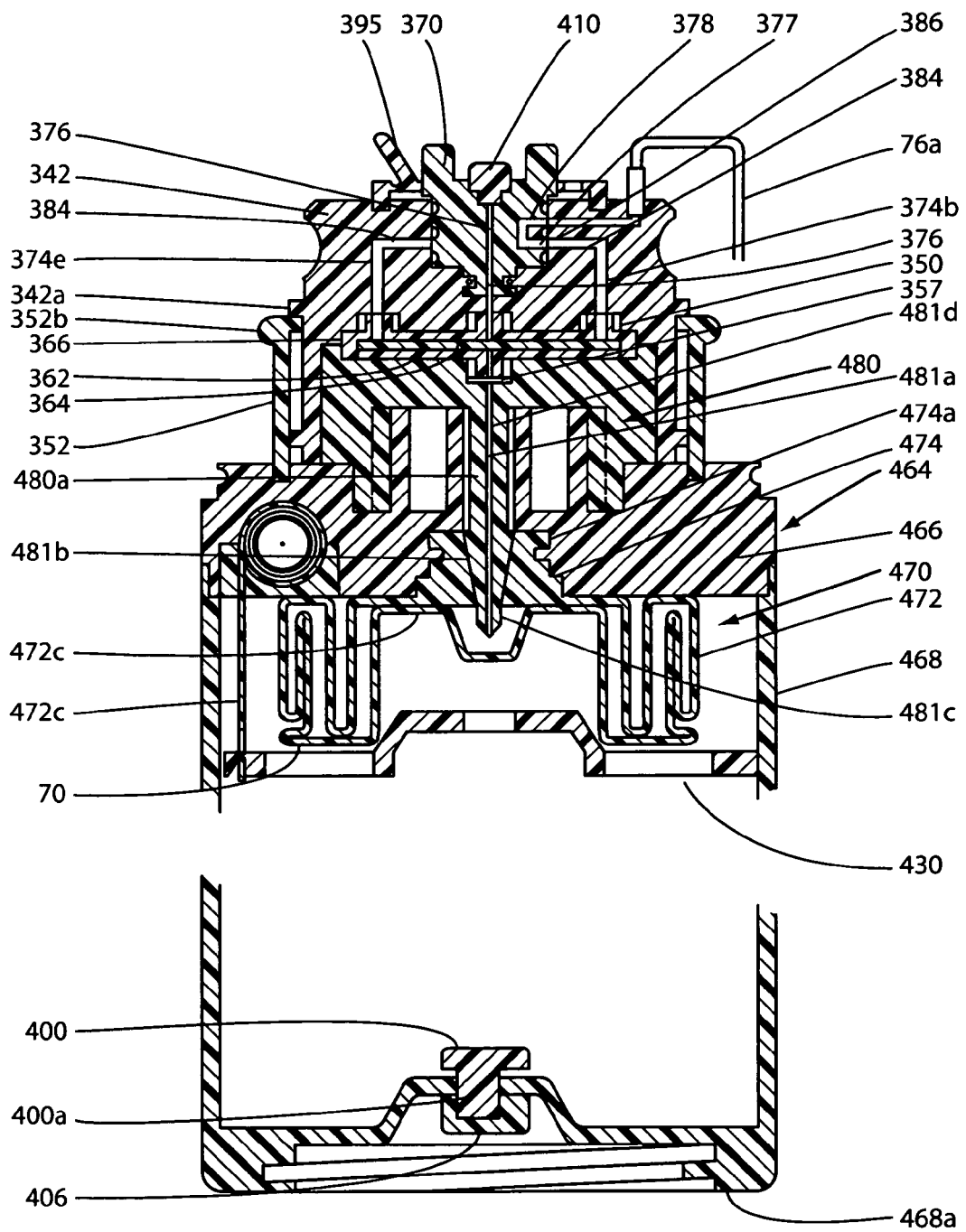
FIG. 84 is a cross-sectional view similar to FIG. 83 but showing the various components of the apparatus as they appear following delivery to the patient of the fluid contained with the fluid reservoir.

Turning next to FIGS. 83 through 88, still another form of the dispensing apparatus of the present invention for dispensing medicaments to a patient is there shown and generally designated by the numeral 462. This alternate form of dispensing apparatus is similar in many respects to that shown in FIGS. 78 through 82 and like numerals are used in FIGS. 83 through 88 to identify like components. As best seen in FIGS. 83 and 84 the supporting structure 464 is similar in many respects to supporting structure 434 and here comprises a connector assembly 466 and a generally cylindrically shaped outer housing 468 that is interconnected with the connector assembly in the manner best seen in FIG. 83 of the drawings.

Disposed within outer housing 468 is the carriage assembly 430, which is of identical construction and operation to that previously described and is releasably locked in its first position by locking means also identical in construction and operation to the locking means previously described herein. Carried by carriage assembly is a reservoir defining assembly 470, which is of a somewhat different construction. This important reservoir defining assembly here includes a unitary collapsible container assembly 472 having a sidewall 472*a*, an interconnected bottom wall 472*b* and an interconnected thin film top wall 472*c*. Connected to top wall 472*c* and extending therefrom is a luer-like connector 474 having external threads 474*a* and an integrally formed sealing wall 474*b*. Connector 474, which is interconnected with top wall 472*c* at the time of manufacture of the collapsible container assembly 472, forms a part of the novel reservoir access means of this latest form of the invention. Collapsible container assembly 472 defines a fluid reservoir 477 that, in a manner presently to be described, is accessible via a slightly differently configured penetrating member 480*a* that penetrates sealing wall 474*b* of top walls 472*c*.

In the preferred form of this latest alternate embodiment of the invention, luer-like connector 474 is sealably interconnected with top wall 472*c* in accordance with the previously described aseptic blow-fill-seal technique. Connector 474 of container 470 is threadably interconnected with connector member 464 and secured in position by locking tabs 68*e* (FIG. 85).

The primary differences between this latest form of dispensing apparatus of the invention and those previously described herein resides in the somewhat differently configured container assembly 470 and the somewhat differently configured penetrating assembly 480. In constructing the container assembly, the basic container is formed using the aseptic blow-fill-seal technique earlier described herein and the reservoir portion of the container is sealed by the interconnected walls of the container.

In order to controllably move the carriage assembly from its first position to its second position, novel stored energy means are provided. This novel stored energy means, which is operably associated with carriage assembly 430, is here provided in the form of three constant force springs 70, which are also identical in construction and operation to that previously described.

As in the earlier described embodiments of the invention, following operation at the operating means of the invention, when the locking means of the invention is manipulated in a manner to unlock the carriage assembly from base portion 468*a* of the outer housing 468, springs 70 will move from their extended position shown in FIG. 83 to their retracted position shown in FIG. 84 and in so doing will controllably move the carriage assembly from its starting position shown in FIG. 83 to its fully deployed or retracted position shown in FIG. 84. As the carriage assembly moves toward its deployed position, the collapsible sidewall 472*a* of the collapsible container 472 will move into the collapsed configuration shown in FIG. 84. As the container collapses and following operation of the operating means, the medicinal fluid contained within the container will be controllably expelled therefrom.

To further control the flow of medicinal fluid from reservoir 477 toward the administration set 76 of the invention and then on to the patient, flow control means are provided. These important flow control means are identical to those previously described in connection with the embodiment of FIGS. 68 and 69 and will not here be further discussed.

As in the last described embodiment, selector member housing 342 is retained in its first position by a tear strip 354 that is removably receivable between a circumferentially extending rib 342*a* formed on housing 342 and the upper extremity 352*b* of guide sleeve 352. When the tear strip 354 is removed and rotary force exerted on selector member housing 342 will move the housing along with the penetrating assembly 480 into the second position shown in FIG. 84 and in so doing will cause the penetrating member 480*a* to penetrate sealing wall 474*b* of top wall 472*c* of the container assembly.

Penetrating member 480*a* is of a slightly different construction that is better suited for penetrating sealing wall 474*b* of the container assembly. More particularly, penetrating member 480*a* has a generally cylindrically shaped body portion 481*a*, an intermediate tapered portion 481*b* and a reduced diameter sharp penetrating extremity 481*c*. To guide the travel of the penetrating member 480*a*, the support member 466 here includes a guide passageway 467, which guides the travel of the penetrating member 480*a* as selector member housing 342, along with penetrating assembly 480 is moved from the first position shown in FIG. 83 to the second position shown in FIG. 84. As the penetrating member 480*a* pierces wall 474*b*, tapered portion 481*b* sealably engages tapered wall 474*c* of luer-like connector 474 thereby forming a substantially fluid seal.

Piercing of wall 474*b* opens a fluid communication path from reservoir 477 to the rate control assembly 350 via a central fluid passageway 481*d* formed in penetrating member 480*a*. From passageway 481*d*, fluid will flow through conventional particulate filter 357, into the inlet of the rate control assembly 350 and into the circumferentially spaced-apart fluid passageways formed in the selector housing 342. In operating the apparatus in the manner previously described herein, by rotating the selector member 370, which is carried by selector member housing 342 passageway 376 can be selectively brought into index with one of the radial extensions 384 of the axially extending passageways formed in selector member 370, thereby providing fluid communication between outlet passageway 378 and the selected one of the circuitous flow passageways formed in rate control plate 364. Since outlet passageway 378 is in fluid communication with the administration set 76 of the invention via passageway 386, the rate of fluid flow toward the patient can be precisely controlled by selecting a rate control passageway of appropriate geometry, width and length that is formed in rate control plate 364 (see FIG. 69E).

Turning next to FIGS. 89 through 94, still another form of the dispensing apparatus of the present invention for dispensing medicaments to a patient is there shown and generally designated by the numeral 492.

This alternate form of dispensing apparatus is similar in many respects to that shown in FIGS. 83 through 88 and like numerals are used in FIGS. 89 through 94 to identify like components.

The major difference between this latest embodiment of the invention and that shown in FIGS. 83 through 88 resides in the differently configured reservoir defining container assembly 494 and the somewhat differently configured penetrating assembly 495. As before, in constructing the container assembly 494, the basic container is formed using the aseptic blow-fill-seal technique earlier described herein and the reservoir portion of the container is sealed by the interconnected walls of the container.

Figure 89:
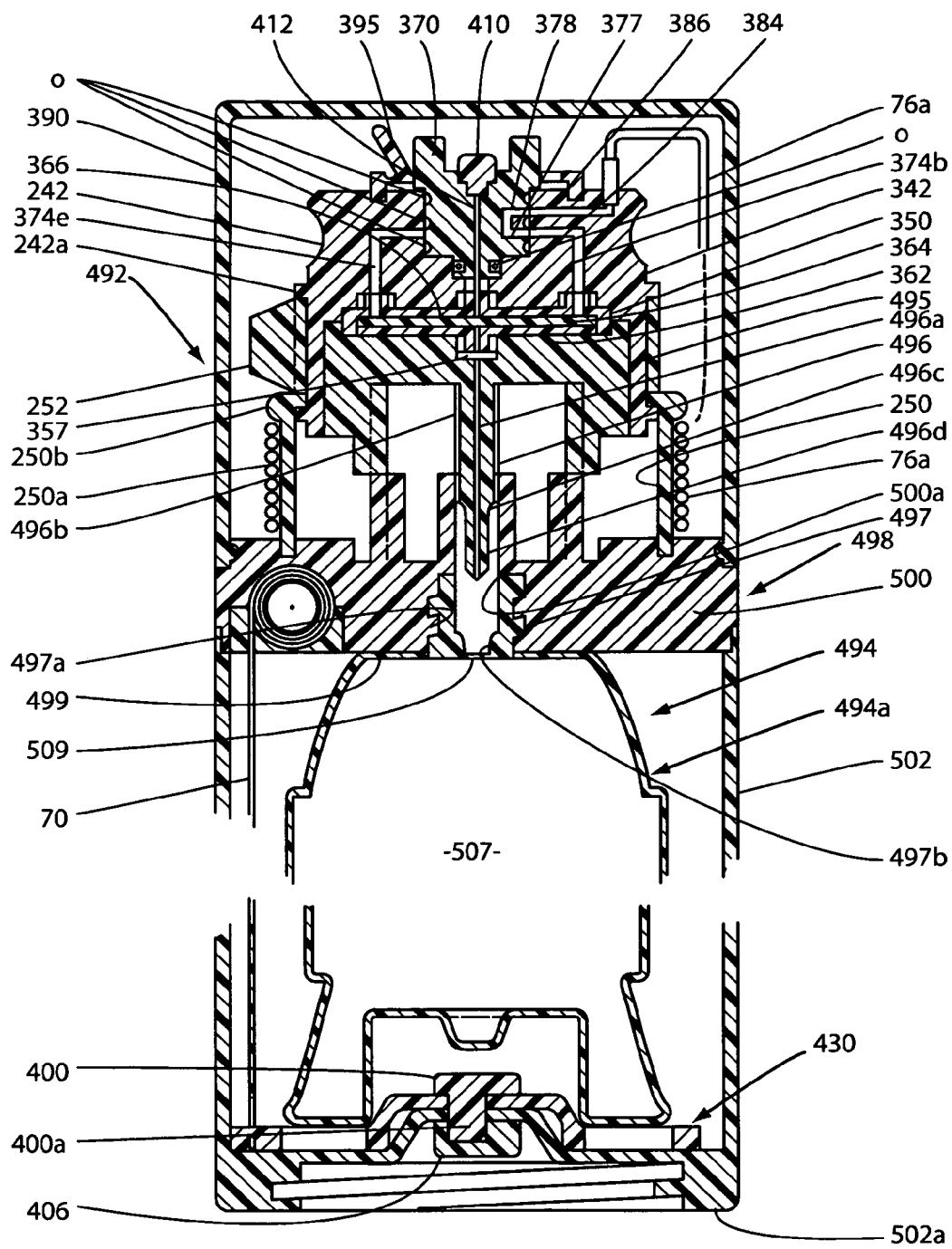
FIG. 89 is a foreshortened, longitudinal, cross-sectional view of still another alternate form of the fluid dispensing apparatus of the invention showing the reservoir in a pre-filled condition.

As best seen in FIGS. 89 and 90 the supporting structure 498 is similar in many respects to supporting structure 464 and here comprises a connector assembly 500 and a generally cylindrically shaped outer housing 502 that is interconnected with the connector assembly in the manner best seen in FIG. 89 of the drawings.

Disposed within outer housing 498 is the carriage assembly 430, which is of identical construction and operation to that previously described and is releasably locked in its first position by locking means also identical in construction and operation to the locking means previously described herein. Carried by the carriage assembly 430 is the previously identified reservoir defining assembly 494.

Once again, in order to controllably move the carriage assembly from its first position to its second position, novel stored energy means are provided. This novel stored energy means, which is operably associated with carriage assembly 430, is here provided in the form of three constant force springs 70, which are also identical construction and operation to that previously described.

As in the earlier described embodiments of the invention, following operation of the operating means at the invention, when the locking means of the invention is manipulated in a manner to unlock the carriage assembly from base portion 502a of the outer housing 502, springs 70 will move from their extended position shown in FIG. 89 to their retracted position shown in FIG. 90 and in so doing will controllably move the carriage assembly from its starting position shown in FIG. 89 to its fully deployed or extended position shown in FIG. 90. As the carriage assembly moves toward its contracted position, container 494a will be urged to move into the collapsed configuration shown in FIGS. 90 and 94. Following operation of the operating means, as the collapsible container collapses, the medicinal fluid contained within the container will be controllably expelled therefrom through fluid passageway 496a formed in the penetrating member 496. As before, penetrating member 496 is receivable within a luer-like connector 497 having internal threads 497a. Connector 497, which forms a part of the novel reservoir access means of this latest form of the invention, is interconnected with top wall 499 of the collapsible container at the time of manufacture of the collapsible container assembly 494.

To further control the flow of medicinal fluid from reservoir 507 of the collapsible container 494a toward the administration set 76 and then on to the patient, flow control means are provided. Once again, this novel fluid flow control means, comprises two cooperating components, namely a rate control means for controlling the rate of fluid flow from the collapsible reservoir and an operating means for controlling fluid flow between the collapsible reservoir and the rate control means. These components are, in this latest embodiment of the invention, substantially identical in construction and operation to those described in connection with Figure drawings 68 through 69A. However, as previously mentioned, the penetrating member 496 is of a slightly different construction that is better suited for penetrating top thin sealing wall 509 of top wall 499 of the container assembly. More particularly, penetrating member 496 has a generally cylindrically shaped body portion 496b which, as before, is coated with an elastomer, such as silicone, an intermediate tapered portion 496c and a reduced diameter penetrating extremity 496d.

Support member 500 includes a guide passageway 500a, which guides the travel of the penetrating member 496. Similarly, member 500 has a sealing wall which sealably engages the reduced diameter penetrating extremity 496d following its penetration of thin sealing wall 509 of the top wall 499 of the container assembly.

In this latest embodiment of the invention, selector member housing 242, along with penetrating assembly 495 is rotatably movable from the first position shown in FIG. 89 to the second position shown in FIG. 90. In addition to guiding the travel of member 242, guide sleeve 250 defines a cylindrical space 250a about which the administration line 76a of the administration set can be coiled in the manner best seen in FIG. 89.

As in the earlier described embodiment, selector member housing 242 is retained in its first position by a tear strip 252 that is removably receivable between a circumferentially extending rib 242a formed on housing 242 and the upper extremity 250b of guide sleeve 250. When the tear strip 252 is removed, a rotational force exerted on selector member housing 242 will move the housing along with the penetrating assembly into the second sealed position shown in FIG. 90 and in so doing will cause the penetrating member 496 to pierce thin sealing container wall 509 in the manner shown in FIG. 90. Piercing of wall 509 opens a fluid communication path from reservoir 507 to the rate control assembly 350 and then into the circumferentially spaced-apart fluid passageways formed in the selector housing 242. In operating the apparatus in the manner previously described herein, by rotating the selector member 370, which is carried by selector member housing 242, the rate of fluid flow toward the patient can be precisely controlled.

Turning next to FIGS. 95 through 99, still another form of the dispensing apparatus of the present invention for dispensing medicaments to a patient is there shown and generally designated by the numeral 512. This alternate form of dispensing apparatus is similar in many respects to that shown in FIGS. 89 through 94 and like numerals are used in FIGS. 95 through 99 to identify like components.

The major difference between this latest embodiment of the invention and that shown in FIGS. 88 through 91 resides in the differently configured reservoir defining container 514. As shown in FIGS. 95 and 98, container 514, rather than being in the nature of the collapsible bottle, comprises a reservoir defining unitary container having a bellows-like sidewall 514a that is movable from the expanded, starting configuration shown in FIG. 95 to the collapsed configuration shown in FIG. 96. This important reservoir defining container here includes, in addition to sidewall 514a, an interconnected bottom wall 514b and an interconnected top wall 514c.

Connected to top wall 514c and extending therefrom is a luer-like connector 497 which is substantially identical to that previously described. Collapsible unitary container 514 defines a fluid reservoir 517 that is accessible via a penetrating member 496 that is identical to the penetrating member previously described in connection with FIGS. 89 and 90 and is adapted to pierce a closure wall 514d in the manner previously described.

Figure 96:
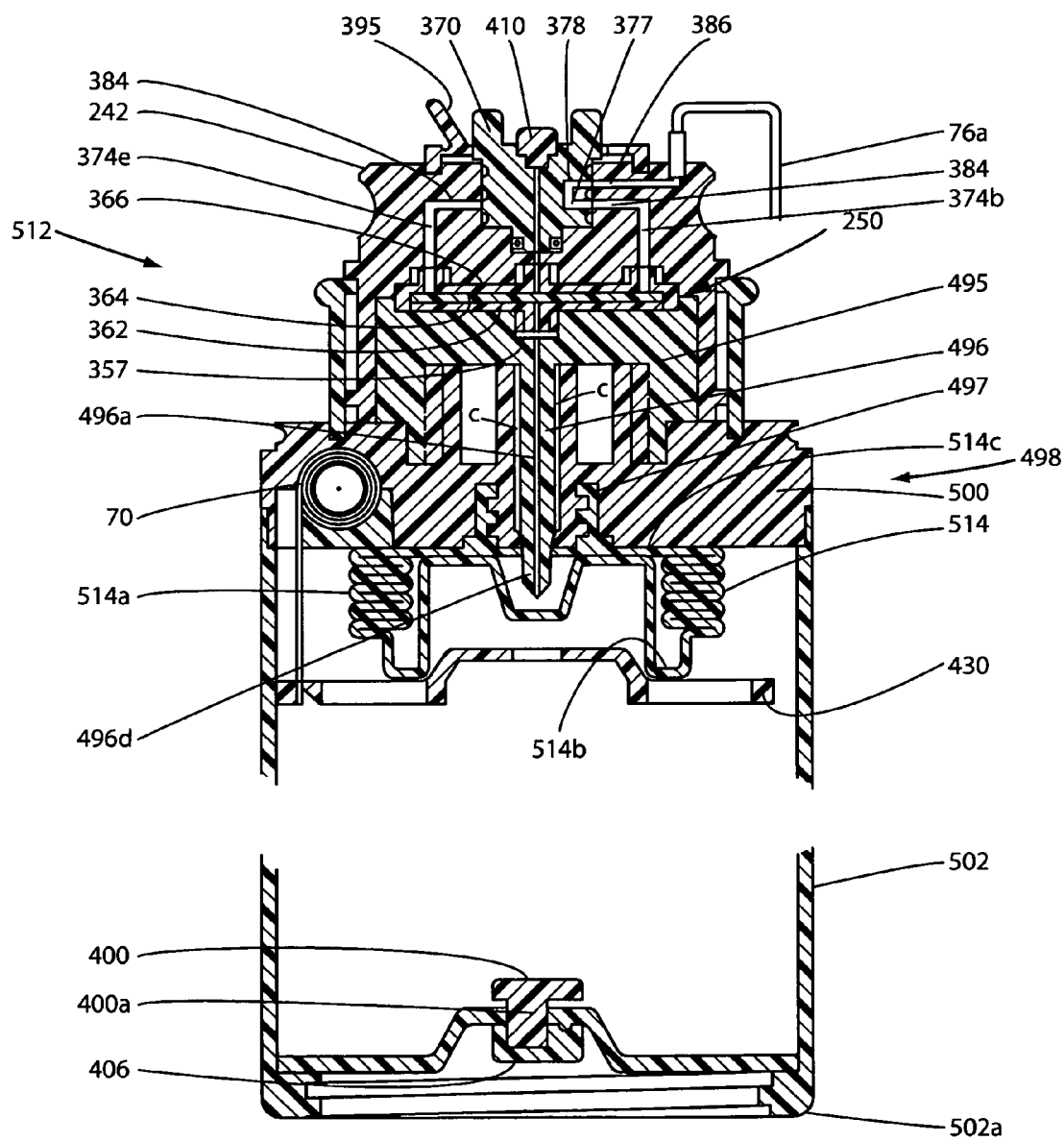
FIG. 96 is a foreshortened, longitudinal, cross-sectional view, similar to FIG. 95, but showing the various components of the apparatus as they appear following delivery to the patient of the fluid contained within the apparatus reservoir with the reservoir substantially empty.

As indicated in FIGS. 95 and 96 the supporting structure 498 is substantially identical to the supporting structure of the last described embodiment. Similarly, the carriage assembly 430, which is carried within cylindrically shaped outer housing 502, is of identical construction and operation to that previously described and is releasably locked in its first position by locking means also identical in construction and operation to the locking means previously described herein. Carried by carriage assembly 430 in the manner illustrated in FIG. 95 is the previously described reservoir defining container assembly 514.

As in the earlier described embodiments of the invention, following the operation of the operating means when the locking means of the invention is manipulated in a manner to unlock the carriage assembly from base portion 502a of the outer housing 502, springs 70 will move from their extended position shown in FIG. 95 to their retracted position shown in FIG. 96 and in so doing will controllably move the carriage assembly from its starting position shown in FIG. 95 to its fully contracted position shown in FIG. 96. As the carriage assembly moves toward its deployed position, the accordion-like, collapsible sidewall 514a of the collapsible container assembly 514 will move into the collapsed configuration shown in FIG. 96. As the container collapses, the medicinal fluid contained within the container will be controllably expelled therefrom.

To further control the flow of medicinal fluid from reservoir 517 toward the administration set 76 of the invention and then on to the patient, flow control means are provided. These important flow control means are identical to those previously described in connection with the embodiment of FIGS. 88 through 91 and will not here be further discussed.

As in the last described embodiment, selector member housing 242 is retained in its first position by a tear strip 252. When the tear strip 252 is removed, a rotational force exerted on selector member housing 242 will move the housing along with the penetrating assembly into the second position shown in FIG. 96 and in so doing will cause the penetrating member 496 to pierce the closure wall 514d and sealably engage sealing wall 497b of member 500.

Piercing of the closure wall 514d opens a fluid communication path from reservoir 517 to the rate control assembly 250. The fluid will then flow into the circumferentially spaced-apart fluid passageways formed in the selector housing 242. In operating the apparatus in the manner previously described herein, by rotating the selector member 370, which is carried by selector member housing 242, the rate of fluid flow toward the patient can be precisely controlled.

Turning next to FIGS. 100 through 105, still another form of the dispensing apparatus of the present invention for dispensing medicaments to a patient is there shown and generally designated by the numeral 522. This alternate form of dispensing apparatus is similar in many respects to that shown in FIGS. 95 through 99 and like numerals are used in FIGS. 100 through 105 to identify like components.

Figure 100:
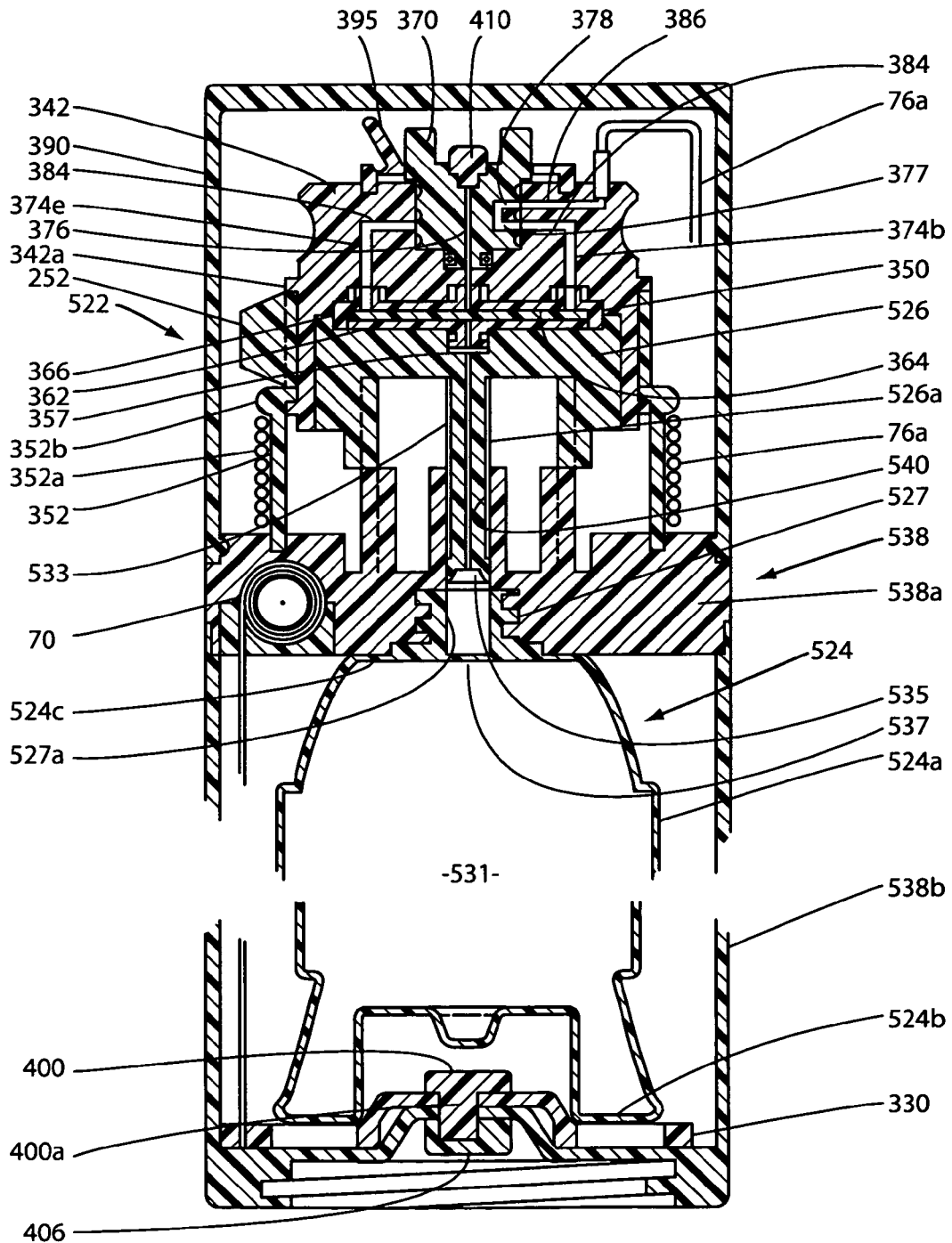
FIG. 100 is a foreshortened, longitudinal, cross-sectional view of yet another alternate form of the fluid dispensing apparatus of the invention showing the reservoir in a pre-filled condition.

The difference between this latest embodiment of the invention and that shown in FIGS. 95 through 99 resides in the slightly differently configured reservoir defining unitary container 524 and the slightly differently configured penetrating assembly 526. As shown in FIG. 100 unitary container 524 is similar in most respects to container 494 of FIG. 89 except that the luer-like connector 527 is provided with a differently configured sealing wall 537 for sealably engaging the slightly differently configured penetrating member 526a of penetrating assembly 526.

Figure 101:
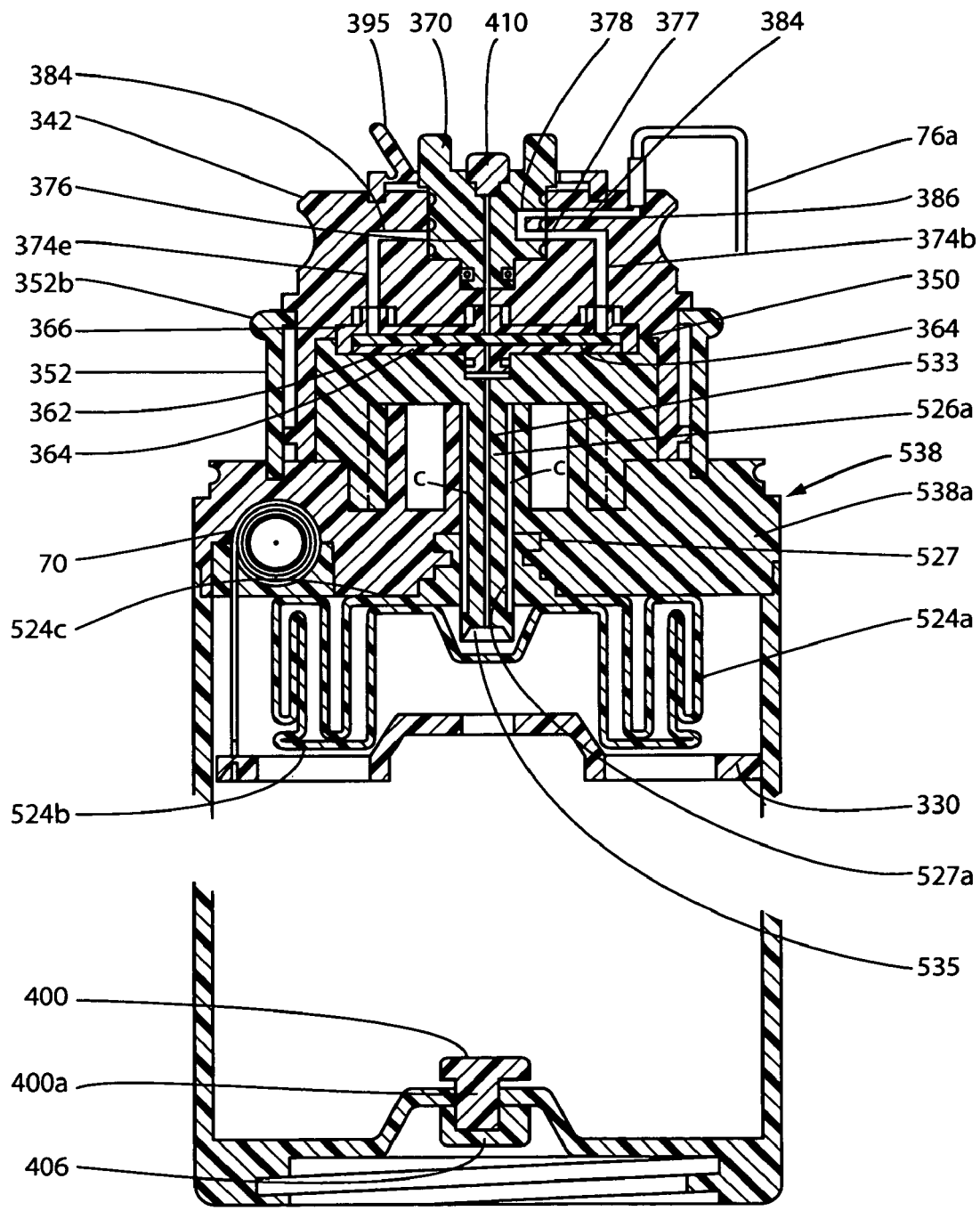
FIG. 101 is a foreshortened, longitudinal, cross-sectional view similar to FIG. 100 but showing the various components of the apparatus as they appear following delivery to the patient of the fluid contained within the apparatus reservoir which is shown substantially empty.
Figure 107:
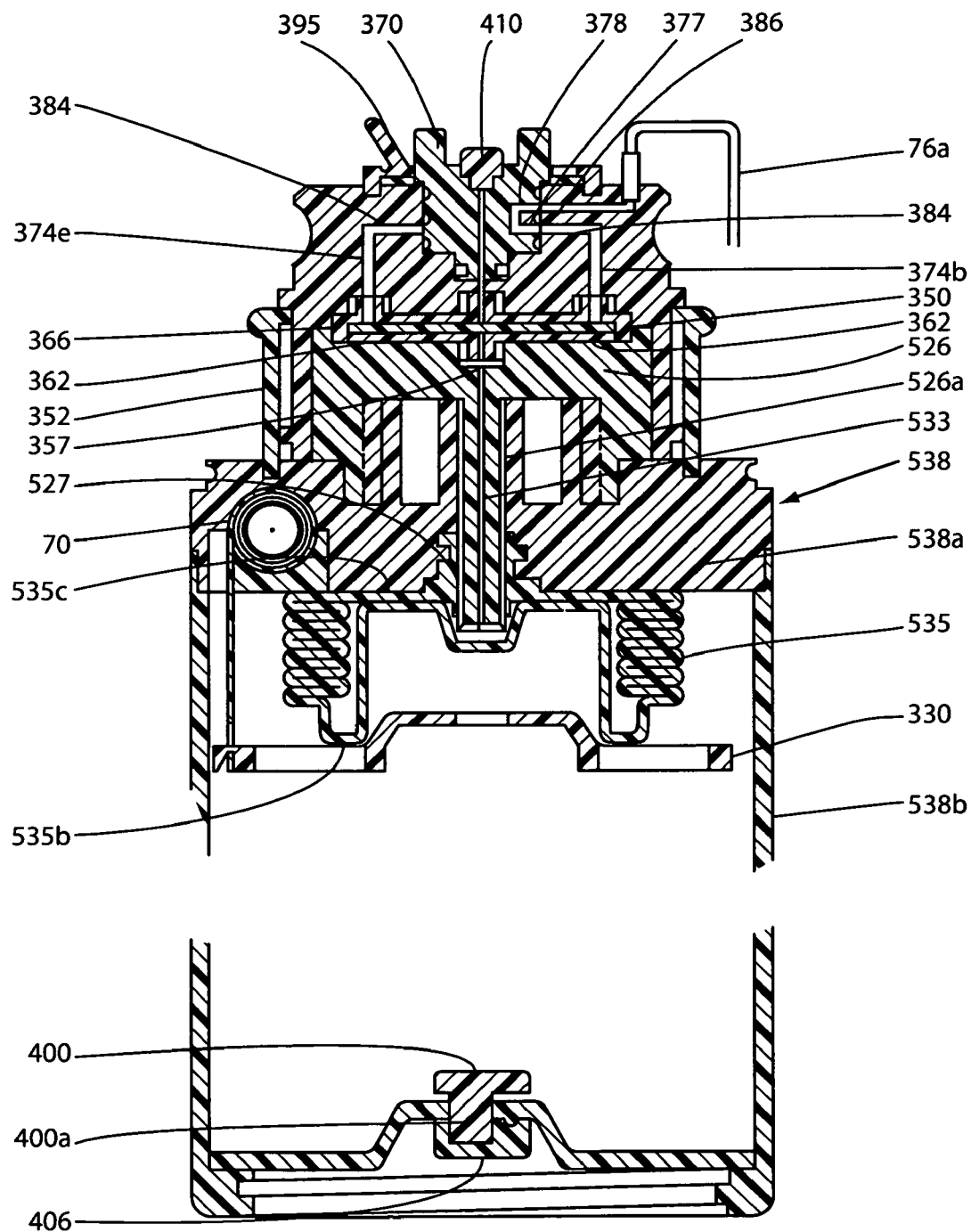

Reservoir defining container 524 has a collapsible sidewall 524a that is movable from the expanded, starting configuration shown in FIG. 100 to the collapsed configuration shown in FIG. 101. This important reservoir defining container here includes, in addition to sidewall 524a, an interconnected bottom wall 524b, an interconnected top wall 524c to which luer-like connector 527 is attached. Luer-like connector 527 here forms a part of the novel reservoir access means of the invention.

Collapsible container assembly 524 defines a fluid reservoir 531 that is accessible via elastomer coated penetrating member 526a. Penetrating member 526a here comprises an elongated body portion 533 that terminates in a substantially punch-like end 535 comprising a cutter means that is adapted to pierce closure wall 537 of luer-like connector 527 in the manner shown in FIGS. 100 and 101. After penetrating member 526a pierces closure wall 537, the elongated body portion 533 of the penetrating member sealably engages sealing wall 527a of luer-like connector 527 in the manner shown in FIG. 101 to form a substantially perfect fluid seal.

As best seen in FIGS. 100 and 101 the supporting structure 538 is similar in many respects to supporting structure 498 and here comprises a connector assembly 538a and a generally cylindrically shaped outer housing 538b that is interconnected with the connector assembly in the manner best seen in FIG. 100 of the drawings. Connector assembly 538a includes a guide passageway 540 that guides the travel of penetrating member 526a.

Except for the differently configured collapsible container 524 and the differently configured penetrating member 526a, the apparatus of this latest form of the invention, including the carriage assembly 330, the locking means, the stored energy source and a flow control means operate in the same manner to accomplish the same result as the apparatus discussed in connection with FIGS. 95 through 99.

Turning next to FIGS. 106 through 110, still another form of the dispensing apparatus of the present invention for dispensing medicaments to a patient is there shown and generally designated by the numeral 532.

This alternate form of dispensing apparatus is similar in many respects to that shown in FIGS. 100 through 105 and like numerals are used in FIGS. 106 through 110 to identify like components.

The difference between this latest embodiment of the invention and that shown in FIGS. 100 through 105 resides only in the differently configured reservoir defining container unitary assembly 534. As shown in FIG. 106, container 535 of reservoir defining container assembly 534, rather than being in the nature of the collapsible bottle, comprises a reservoir defining container having a bellows-like sidewall 535a that is movable from the expanded, starting configuration shown in FIG. 106 to the collapsed configuration shown in FIG. 107. This important reservoir defining container here includes, in addition to sidewall 535a, an interconnected bottom wall 535b and an interconnected top wall 535c.

Connected to top wall 535c and extending therefrom is luer-like connector 527, which is identical to that shown in FIG. 100. Collapsible container assembly 534 defines a fluid reservoir 537 that is accessible via penetrating member 526a that is identical to the penetrating member previously described in connection with FIGS. 100 and 101 and is adapted to pierce an integrally formed thin film closure wall 539 in the manner previously described.

Except for the differently configured collapsible unitary container 535a, the apparatus of this latest form of the invention, including the carriage assembly 330, the locking means, the stored energy source and a flow control means operate in the same manner to accomplish the same result as the apparatus discussed in connection with FIGS. 100 through 105.

Referring next to FIGS. 111 through 116, still another form of the dispensing apparatus of the present invention for dispensing medicaments to a patient is there shown and generally designated by the numeral 542. This alternate form of dispensing apparatus is similar in some respects to the earlier described embodiments shown in FIGS. 72 through 77 and like numerals are used in FIGS. 111 through 116 to identify like components.

The primary difference between this latest form of dispensing apparatus and that previously described in connection with FIGS. 72 through 77 resides in the provision of a novel stored energy source, which is of a totally different construction. More particularly, rather than being constant force springs, the novel stored energy means of this latest form of the invention comprises a compressible, expandable sponge-like configuration, which is generally designated in the drawings by the numeral 544. This unique stored energy source, which functions to move carriage 546 from the first compressed position shown in FIG. 111 to the second expanded position shown in FIG. 112 can take several forms. By way of non-limiting example, stored energy source 544 can comprise a microporous, mesoporous, macroporous, ordered structure and can be constructed from Polypropylene (PP), Ultra High Molecular Weight Polyethylene (UHMWPE), High Density Polyethylene (HDPE), Polyvinylidene Fluoride (PVDF), Ethyle-vinyl Acetate (EVA), Styrene Acrylonitrile (SAN), Polytetrafluroethylene (PTFE) and porous cellulose acetate. A suitable source of these materials is NUSIL Technologies of Carpinteria, Calif. However, practice has shown that any porous plastic material including an open cell, porous sponge material is suitable for use in constructing the stored energy source. The stored energy source can also comprise a metallized foam as described in greater detail in connection with the embodiments of FIGS. 65 through 67.

Figure 111:
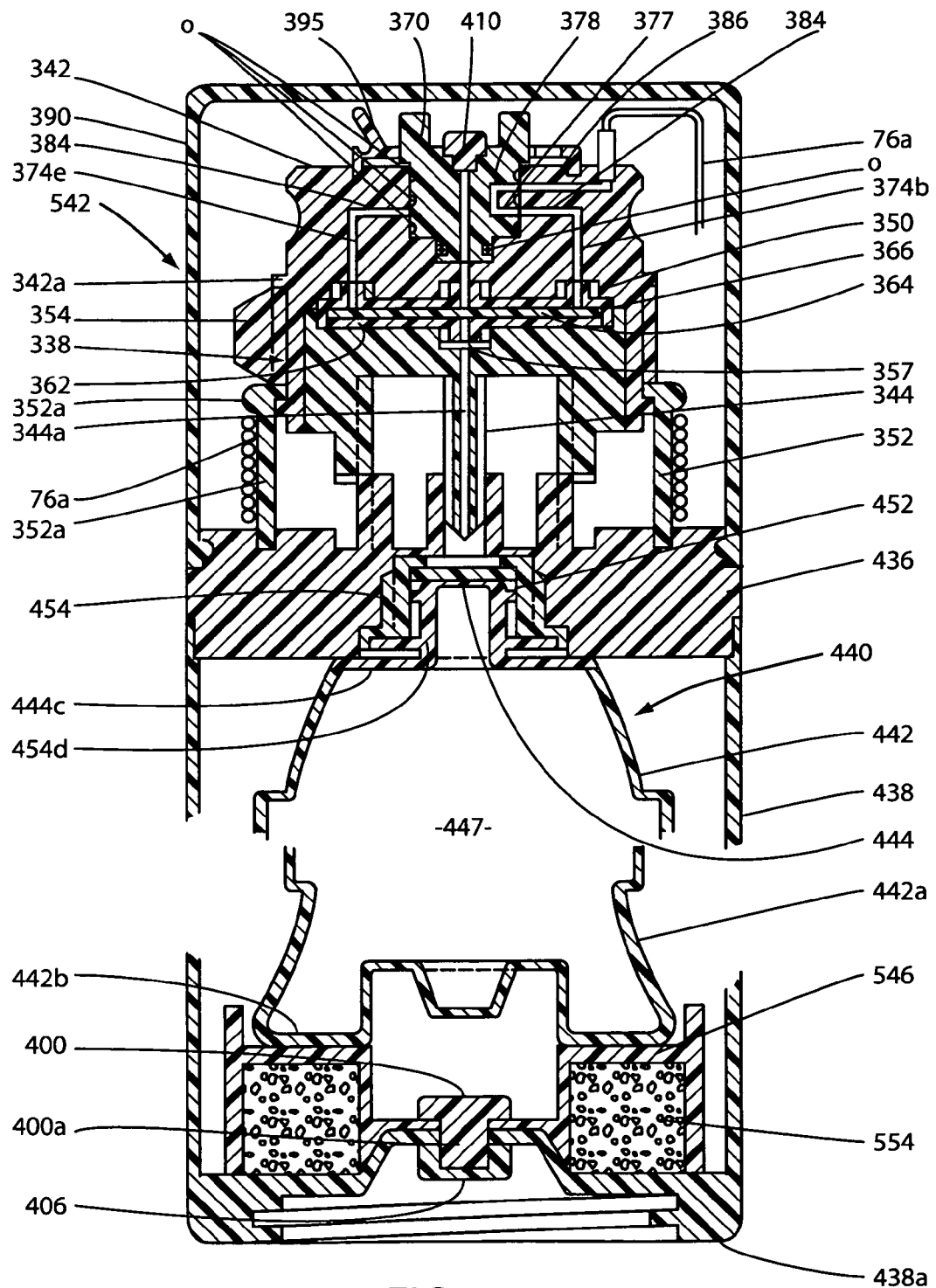

As in the embodiment of the invention shown in FIG. 72, the reservoir defining assembly 440 here comprises a collapsible container assembly 442, which is of identical construction that previously described and is carried by carriage assembly 546 in the manner illustrated in FIG. 111. Container assembly 442 can be interconnected with the connector member either by threads, or as shown here, by a snap-fit assembly.

As before, the carriage assembly 546 is releasably secured to base portion 438*a* of the outer housing 438 by a novel locking means. Following operation of the operating means when the locking means of the invention is manipulated in a manner to unlock the carriage assembly 546 from the base portion 438*a*, sponge 544 will expand from the first compressed position shown in FIG. 111 to the second expanded position shown in FIG. 112 and in so doing will controllably move the carriage assembly from its starting position shown in FIG. 111 to its fully deployed or extended position shown in FIG. 112. As the carriage assembly moves toward its deployed position, the sidewall 442*a* of the collapsible container 442 will move into the collapsed configuration shown in FIG. 112. As the collapsible container collapses, the medicinal fluid contained within the container reservoir 447 will be controllably urged outwardly thereof.

To control the flow of medicinal fluid from reservoir 447 toward the administration set 76 of the invention and then on to the patient, flow control means are provided. Once again, this novel fluid flow control means, comprises two cooperating components, namely a rate control means for controlling the rate of fluid flow from the collapsible reservoir and an operating means for controlling fluid flow between the collapsible reservoir and the rate control means. Both the operating means and the rate control means of this latest form of the invention are identical in construction and operation to those described in connection with the embodiment of FIGS. 72 through 77.

As in the earlier described embodiment, the selector member housing 342 is retained in its first position by a tear strip 354. When the tear strip is removed, a rotational force exerted on selector member housing 342 will move the housing along with the penetrating assembly 338 into the second position shown in FIG. 112 and in so doing will cause the penetrating member 344 to pierce the septal membrane 452 as well as the thin sealing closure wall 444 in the manner shown in FIG. 112. Piercing of the membrane 452 and the thin sealing closure wall 444 opens a fluid communication path from reservoir 447 to the rate control assembly 350 via a central fluid passageway 344*a* formed in penetrating member 344. From reservoir 447, the fluid will flow through central fluid passageway 344*a* of penetrating member 344, through conventional particulate filter 357, through the rate control assembly 350, through the selector member 370 and toward the patient via the administration set 76.

Referring next to FIGS. 117 through 121, yet another form of the dispensing apparatus of the present invention for dispensing medicaments to a patient is there shown and generally designated by the numeral 552. This alternate form of dispensing apparatus is similar in most respects to that shown in FIGS. 111 through 116 and like numerals are used in FIGS. 117 through 121 to identify like components. The major difference between this latest embodiment of the invention and that shown in FIGS. 111 through 116 resides in the differently configured reservoir defining container 554. As shown in FIGS. 117 and 120, unitary container 554, rather than being in the nature of the collapsible bottle, comprises a reservoir defining container having a bellows-like sidewall 554*a* that is movable from the expanded, starting configuration shown in FIG. 117 to the collapsed configuration shown in FIG. 118. This important reservoir defining container here includes, in addition to sidewall 554*a*, an interconnected bottom wall 554*b*, an interconnected top wall 554*c* and an interconnected neck portion 554*d*, which is sealed following filling at the time of manufacture by a thin closure wall 555. Neck portion 554*d* forms a part of the novel reservoir access means of the invention. Collapsible container 554 defines a fluid reservoir 557 that is accessible via a penetrating member 344 that is identical to that previously described. Elastomer-coated penetrating member 344 is adapted to pierce closure wall 555 as well as a pierceable membrane 452, which is positioned over closure wall 555 by means of a closure cap 454, which is affixed to the neck portion 554*d* of container assembly 554 (see also FIGS. 120 and 121). As clearly seen in FIG. 120 of the drawings, container 554 has a base having a width and a bottom wall 554*b* that includes a cup shaped portion that extends into fluid reservoir 557 by a distance greater than one-sixth the width of the container base.

As best seen in FIGS. 117 and 118 the supporting structure is substantially identical to the supporting structure of the last described embodiment and here comprises a connector assembly 436 and a generally cylindrically shaped outer housing 438 that is interconnected with the connector assembly in the manner best seen in FIG. 117 of the drawings.

Disposed within outer housing 438 is the carriage assembly 546, which is of identical construction and operation to that previously described and is releasably locked in its first position by locking means also identical in construction and operation to the locking means previously described herein. Carried by the carriage assembly is the previously described reservoir defining container 554.

As in the last described embodiment of the invention, thin sealing closure wall 555 is sealably interconnected with neck portion 554*d* and top wall 554*c* in accordance with the previously described aseptic blow-fill-seal technique previously discussed.

As before, the basic unitary container 554 is formed using the earlier described aseptic blow-fill-seal technique and after filling the reservoir portion of the container is sealed by the thin closure wall 555. The piercable membrane 452 is then positioned over the closure wall 555 and the cap 454 is positioned over the piercable membrane and secured to neck portion 554*d* by any suitable means such as adhesive bonding or sonic welding. The container along with neck portion 554*d* is then interconnected with connector member 436 and retained in position by the previously described snap-fit tabs.

Once again, in order to controllably move the carriage assembly from its first position to its second position, novel stored energy means are provided. This novel stored energy means, which is operably associated with carriage assembly 546, is here provided in the form of a compressible, expandable sponge-like configuration 544, which is identical in construction and operation to that previously described.

As in the earlier described embodiments of the invention following operation of the operating means, when the locking means of the invention is manipulated in a manner to unlock the carriage assembly from base portion 438*a* of the outer housing 438, sponge 544 will expand and in so doing will controllably move the carriage assembly from its starting position shown in FIG. 117 to its fully deployed or extended position shown in FIG. 118. As the carriage assembly moves toward its deployed position, the sidewall 554*a* of the collapsible container 554 will be urged to move toward the collapsed configuration shown in FIG. 118. As the collapsible container collapses, the medicinal fluid contained within the container will be controllably expelled therefrom.

To control the flow of medicinal fluid from reservoir 557 toward the administration set 76 of the invention and then on to the patient, flow control means are provided. Once again, this novel fluid flow control means, comprises two cooperating components, namely a rate control means for controlling the rate of fluid flow from the collapsible reservoir and an operating means for controlling fluid flow between the collapsible reservoir and the rate control means. Both the operating means and the rate control means of this latest form of the invention are identical in construction and operation to those described in connection with the embodiment of FIGS. 111 and 112.

As in the earlier described embodiment, selector member housing 342 is retained in its first position by a tear strip 354. When the tear strip is removed, a rotational force exerted on selector member housing 342 will move the housing along with the penetrating assembly into the second position shown in FIG. 118 and in so doing will cause the penetrating member 344 to pierce the membrane 452 as well as the closure wall 555 in the manner shown in FIG. 118. Piercing of the membrane 452 and the closure wall 555 opens a fluid communication path from reservoir 557 to the rate control assembly 350 via a central fluid passageway 344a formed in penetrating member 344. From reservoir 557, the fluid will flow through central fluid passageway 344a of penetrating member 344, through conventional particulate filter 357, through the rate control assembly 350, through the selector member 370 and toward the patient via the administration set 76.

Turning next to FIGS. 122 through 126, still another form of the dispensing apparatus of the present invention for dispensing medicaments to a patient is there shown and generally designated by the numeral 562. This alternate form of dispensing apparatus is similar in many respects to that shown in FIGS. 83 through 88 and like numerals are used in FIGS. 122 through 126 to identify like components. As best seen in FIGS. 122 and 123 the supporting structure 564 is similar in many respects to supporting structure 436 of FIGS. 111 and 112 and here comprises a connector assembly 566 and a generally cylindrically shaped outer housing 568 that is interconnected with the connector assembly in the manner best seen in FIG. 122 of the drawings.

Disposed within outer housing 568 is the carriage assembly 546, which is of identical construction and operation to that described in connection with the preceding embodiment and is releasably locked in its first position by locking means also identical in construction and operation to the locking means previously described herein. Carried by carriage assembly 546 is a reservoir defining assembly 570, which is of a somewhat different construction. This important reservoir defining assembly here includes a bottle-like collapsible, unitary container assembly 572 having a sidewall 572a, an interconnected bottom wall 572b and an interconnected top wall 572c. Connected to top wall 572c and extending therefrom is a luer-like connector 574 having external threads 574a and a thin film sealing wall 574b. Connector 574, which is interconnected with top wall 572c at the time of manufacture of the collapsible container assembly, forms a part of the novel reservoir access means of this latest form of the invention. Collapsible container assembly 570 defines a fluid reservoir 577 that is accessible via a penetrating member 344 that is identical to that previously described and is adapted to pierce top wall 574b and sealably engage a sealing wall 574c formed on connector 574.

In the preferred form of this latest alternate embodiment of the invention, following filling of the container the luer-like connector 574 is sealably interconnected with top wall 572c in accordance with the previously described aseptic blow-fill-seal technique.

In order to controllably move the carriage assembly from its first position to its second position, novel stored energy means are provided. This novel stored energy means, which is operably associated with carriage assembly 546, is here provided in the form of a compressible, expandable sponge-like configuration 544, which is identical in construction and operation to that previously described.

As in the earlier described embodiments of the invention, following operation of the operating means when the locking means of the invention is manipulated in a manner to unlock the carriage assembly from base portion 568a of the outer housing 568, sponge 544 will expand from its extended position shown in FIG. 122 to the position shown in FIG. 123 and in so doing will controllably move the carriage assembly from its starting position shown in FIG. 122 to its fully deployed or extended position shown in FIG. 123. As the carriage assembly moves toward its deployed position, the collapsible sidewall 572a of the collapsible container 572 will move into the collapsed configuration shown in FIG. 123. As the container collapses, the medicinal fluid contained within the container will be controllably expelled therefrom.

To further control the flow of medicinal fluid from reservoir 577 toward the administration set 76 of the invention and then on to the patient, flow control means are provided. These important flow control means are identical to those previously described in connection with the previously described embodiments and will not here be further discussed.

As in the last described embodiment, selector member housing 342 is retained in its first position by a tear strip 354. When the tear strip 354 is removed, a rotational force exerted on selector member housing 342 will move the housing along with the penetrating assembly 344 into the second position shown in FIG. 123 and in so doing will cause the penetrating member 344 to penetrate top wall 574b of the container assembly.

Piercing of wall 574b opens a fluid communication path from reservoir 577 to the rate control assembly 350 via a central fluid passageway 344a formed in penetrating member 344. From passageway 344a, fluid will flow through conventional particulate filter 357, into the inlet of the rate control assembly 350 and into the circumferentially spaced-apart fluid passageways formed in the selector housing 342. In operating the apparatus in the manner previously described herein, by rotating the selector member 370, which is carried by selector member housing 342, the rate of fluid flow toward the patient can be precisely controlled by selecting the rate control passageway of appropriate geometry, width and length that is formed in rate control plate 364.

Turning next to FIGS. 127 through 130, yet another form of the dispensing apparatus of the present invention for dispensing medicaments to a patient is there shown and generally designated by the numeral 572. This alternate form of dispensing apparatus is similar in many respects to that shown in FIGS. 122 through 126 and like numerals are used in FIGS. 127 through 130 to identify like components. As best seen in FIGS. 127 and 128 the supporting structure 564 is similar in many respects to supporting structure 436 of FIGS. 111 and 112 and here comprises a connector assembly 566 and a generally cylindrically shaped outer housing 568 that is interconnected with the connector assembly in the manner best seen in FIG. 127 of the drawings.

Disposed within outer housing 568 is the carriage assembly 546, which is of identical construction and operation to that described in connection with the preceding embodiment and is releasably locked in its first position by locking means also identical in construction and operation to the locking means previously described herein. Carried by carriage assembly 546 is a reservoir defining assembly 574, which is of a somewhat different construction. This important reservoir defining assembly here comprises a unitary collapsible container assembly 576 having an accordion-like sidewall 576a, an interconnected bottom wall 576b and an interconnected top wall 576c. Connected to top wall 572c and extending therefrom is a luer-like connector 578 having external threads 578a and a sealing wall 578b. Connector 578, which is interconnected with top wall 576c at the time of manufacture of the collapsible container assembly, forms a part of the novel reservoir access means of this latest form of the invention. Collapsible container assembly 576 defines a fluid reservoir 579 that is accessible via a penetrating member 344 that is identical to that previously described and is adapted to pierce top wall 578b and sealably engage sealing wall 578c formed on connector 578.

In the preferred form of this latest alternate embodiment of the invention, following filling of the container the luer-like connector 578 is sealably interconnected with top wall 576c in accordance with the previously described aseptic blow-fill-seal technique.

In order to controllably move the carriage assembly from its first position to its second position, novel stored energy means are provided. This novel stored energy means, which is operably associated with carriage assembly 546, is here provided in the form of a compressible, expandable sponge-like configuration 544, which is identical in construction and operation to that previously described.

As in the earlier described embodiments of the invention, following operation of the operating means when the locking means of the invention is manipulated in a manner to unlock the carriage assembly from base portion 568a of the outer housing 568, sponge 544 will expand from its compressed position shown in FIG. 127 to the expanded position shown in FIG. 128 and in so doing will controllably move the carriage assembly from its starting position shown in FIG. 127 to its fully deployed or extended position shown in FIG. 128. As the carriage assembly moves toward its deployed position, the collapsible sidewall 576a of the collapsible container 576 will move into the collapsed configuration shown in FIG. 128. As the container collapses, the medicinal fluid contained within the container will be controllably expelled therefrom.

To further control the flow of medicinal fluid from reservoir 579 toward the administration set 76 of the invention and then on to the patient, flow control means are provided. These important flow control means are identical to those previously described in connection with the previously described embodiments and will not here be further discussed.

As in the last described embodiment, selector member housing 342 is retained in its first position by a tear strip 354. When the tear strip 354 is removed, a rotational force exerted on selector member housing 342 will move the housing along with the penetrating assembly 344 into the second position shown in FIG. 128 and in so doing will cause the penetrating member 344 to penetrate top wall 578b of the container assembly.

Piercing of wall 578b opens a fluid communication path from reservoir 579 to the rate control assembly 350 via a central fluid passageway 344a formed in penetrating member 344. From passageway 344a, fluid will flow through conventional particulate filter 357, into the inlet of the rate of control assembly 350 and into the circumferentially spaced-apart fluid passageways formed in the selector housing 342. In operating the apparatus in the manner previously described herein, by rotating the selector member 370, which is carried by selector member housing 342, the rate of fluid flow toward the patient can be precisely controlled by selecting the rate control passageway of appropriate geometry and length that is formed in rate control plate 364.

Having now described the invention in detail in accordance with the requirements of the patent statutes, those skilled in this art will have no difficulty in making changes and modifications in the individual parts or their relative assembly in order to meet specific requirements or conditions. Such changes and modifications may be made without departing from the scope and spirit of the invention, as set forth in the following claims.

We claim:

1. A dispensing device for dispensing medicaments to a patient comprising:
   (a) a supporting structure;
   (b) a pre-filled collapsible container having a continuous wall formed of a single material carried by said supporting structure, said collapsible container comprising an hermetically sealed reservoir having an outlet port and including sealing means for sealing said outlet port, said sealing means comprising a shearable nipple having a severable end portion;
   (c) stored energy means carried by said supporting structure and operably associated with said collapsible reservoir for collapsing said collapsible reservoir to expel fluid therefrom;
   (d) an administration set, including an administration line interconnected with said outlet of said collapsible reservoir; and
   (e) fluid flow control means carried by said supporting structure for controlling fluid flow from said collapsible reservoir toward said administration set, said fluid flow control means comprising an operating shaft having a cavity and including a knife mounted within said cavity for severing said severable end portion of said shearable nipple.

2. The dispensing device as defined in claim 1 in which said pre-filled collapsible fluid reservoir is aseptically filled and sealed at time of manufacture.

3. The dispensing device as defined in claim 1 in which flow control means comprises rate control means for controlling the rate of fluid flow from said collapsible reservoir toward said administration set.

4. The dispensing device as defined in claim 1 in which said stored energy means comprises a spring operably interconnected with said collapsible reservoir.

5. The dispensing device as defined in claim 1 in which said flow control means comprises rate control means for controlling the rate of fluid flow from said collapsible reservoir toward said administration set.

6. The dispensing device as defined in claim 5 in which said rate control means includes selector means for selecting the rate of fluid flow between said collapsible reservoir and said administration set.

7. The dispensing device as defined in claim 6 in which said selector means comprises a selector housing carried by said supporting structure and a selector member rotatably carried by said selector housing.

* * * * *